United States Patent
Richter

(10) Patent No.: US 10,183,970 B2
(45) Date of Patent: Jan. 22, 2019

(54) CYTOTOXIC TUBULYSIN COMPOUNDS FOR CONJUGATION

(71) Applicant: Tube Pharmaceuticals GmbH, Wiener Neudorf (AT)

(72) Inventor: Wolfgang Richter, Munich (DE)

(73) Assignee: Tube Pharmaceuticals GmbH, Wiener Neudorf (AT)

( * ) Notice: Subject to any disclaimer, the term of this patent is extended or adjusted under 35 U.S.C. 154(b) by 0 days.

(21) Appl. No.: 15/114,710

(22) PCT Filed: Jan. 28, 2015

(86) PCT No.: PCT/EP2015/000161
§ 371 (c)(1),
(2) Date: Jul. 27, 2016

(87) PCT Pub. No.: WO2015/113760
PCT Pub. Date: Aug. 6, 2015

(65) Prior Publication Data
US 2016/0340386 A1 Nov. 24, 2016

(30) Foreign Application Priority Data
Jan. 28, 2014 (EP) .................................... 14000291

(51) Int. Cl.
| | |
|---|---|
| C07K 5/062 | (2006.01) |
| C07K 5/078 | (2006.01) |
| C07D 417/12 | (2006.01) |
| C07D 417/14 | (2006.01) |
| C07D 277/56 | (2006.01) |
| C07K 5/02 | (2006.01) |
| A61K 38/00 | (2006.01) |

(52) U.S. Cl.
CPC ........ *C07K 5/06139* (2013.01); *C07D 277/56* (2013.01); *C07D 417/12* (2013.01); *C07D 417/14* (2013.01); *C07K 5/021* (2013.01); *C07K 5/06034* (2013.01); *C07K 5/06043* (2013.01); *C07K 5/06052* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,056,942 B2 * | 6/2006 | Hildesheim | C07D 209/88 514/411 |
| 2011/0027274 A1 | 2/2011 | Cheng et al. | |
| 2013/0116195 A1 | 5/2013 | Leamon et al. | |

FOREIGN PATENT DOCUMENTS

| | | |
|---|---|---|
| WO | 2004005326 A2 | 1/2004 |
| WO | 2004046170 A2 | 6/2004 |
| WO | 2005112919 A2 | 12/2005 |
| WO | 2012019123 A1 | 2/2012 |
| WO | 2012171020 A1 | 12/2012 |
| WO | 2013085925 A1 | 6/2013 |
| WO | 2013149185 A1 | 10/2013 |
| WO | 2013173391 A1 | 11/2013 |
| WO | 2014/009774 A1 | 1/2014 |
| WO | 2014008375 A1 | 1/2014 |
| WO | 2014040752 A1 | 3/2014 |
| WO | 2014078484 A1 | 5/2014 |
| WO | 2014197871 A2 | 12/2014 |

OTHER PUBLICATIONS

Jeffrey et al. ('Design, synthesis, and in vitro evaluation of dipeptide-based antibody minor groove binder conjugates' J Med Chem v48 2005 pp. 1344-1358) (Year: 2005).*
Vippagunta et al. ('Crystalline solids' Advanced Drug Delivery Reviews v48 2001 pp. 3-26) (Year: 2001).*
Dosio, et al. "Immunotoxins and Anticancer Drug Conjugate Assemblies: The Role of the Linkage between Components" Toxins 2011, vol. 3, pp. 848-883.
M. Sesay, "Monoclonal Antibody Conjugation via Chemical Modification" BioPharm International, Dec. 1, 2003, pp. 32-39.
Pasut, et al. "State of the art in PEGylation: The great versatility achieved after forty years of research" Journal of Controlled Release, vol. 161, 2012, pp. 461-472.
Baskin et al., "Copper-Free Click Chemistry for Dynamic in Vivo Imaging" PNAS, Oct. 23, 2007, vol. 104, No. 43, pp. 16793-16797.
Sletten et al., "From Mechanism to Mouse: A Tale of Two Bioorthogonal Reactions" Accounts of Chemical Research, pp. 666-676, 2011, vol. 44, No. 9.
Schultz et al., "Synthesis of a DOTA-Biotin Conjugate for Radionuclide Chelation via Cu-Free Click Chemistry" Organic Letters, 2010, vol. 12, No. 10, pp. 2398-2401.
Schoenebeck, et al., "Reactivity and Regioselectivity in 1, 3-Dipolar Cycloadditions of Azides to Strained Alkynes and Alkenes: A Computational Study" Journal of the American Chemical Society, vol. 131, No. 23, 2009, pp. 8121-8133.
Popp et al., "Making and Breaking Peptide Bonds: Protein Engineering Using Sortase" Angewandte Chemie International Edition, 2011, vol. 50, pp. 5024-5032.
Shankar, et al., "Synthesis and Cytotoxicity Evaluation of Diastereoisomers and N-terminal Analogues of Tubulysin-U", Tetrahedron Letters, vol. 54, 2013, pp. 6137-6141.
Wang, et al., "Stereoselective Total Synthesis of Tubulysin V" Chinese Journal of Chemistry, 2013, vol. 31, pp. 40-48.

* cited by examiner

*Primary Examiner* — Karlheinz R. Skowronek
*Assistant Examiner* — Ronald T Niebauer
(74) *Attorney, Agent, or Firm* — Mintz Levin Cohn Ferris Glovsky and Popeo, P.C.; Peter F. Corless

(57) ABSTRACT

The present invention provides one or more compounds of formula (I) for conjugation to small molecules, polymers, peptides, proteins, antibodies, antibody fragments etc.

(I)

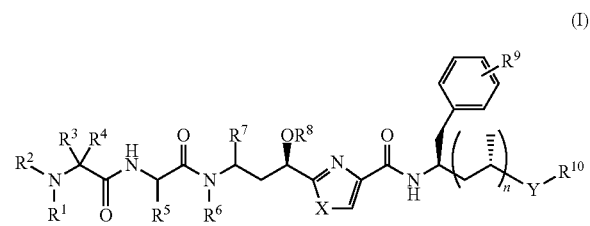

9 Claims, 1 Drawing Sheet

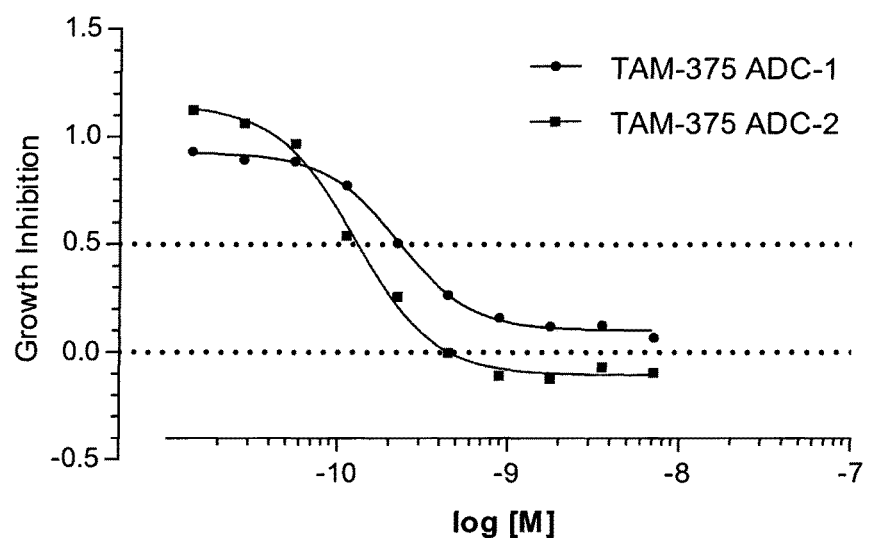

CYTOTOXIC TUBULYSIN COMPOUNDS FOR CONJUGATION

This application is a National Phase application filed under 35 U.S.C. § 371 of PCT International Application No. PCT/EP2015/000161 with an International Filing Date of Jan. 28, 2015, which claims under 35 U.S.C. 119(a) the benefit of European Application No. 14000291.6 filed Jan. 28, 2014, the entire contents of which are incorporated herein by reference.

The present invention refers to cytotoxic molecules which have been modified with spacer moieties in such a way that a variety of different linker types used in the conjugation of payloads to small molecules, polymers, peptides, proteins, antibodies, antibody fragments etc. can be adopted and thereby, many different conjugation methods can be applied.

Toxin classes used for conjugations which are derived from natural products such as doxorubicins and derivatives thereof, dolastatins and derivatives thereof, maytansins and derivatives thereof, calicheamycins and derivatives thereof, amanitins and derivatives thereof, are usually very difficult to conjugate because of lack of functional groups or if a functional group is used the biological activity is lost (F. Dosio et al. *Toxins* 2011, 3, 848-883 and citations therein). In contrast, in the tubulysins and their synthetic analogs, the Cytolysins two natural functional groups are present, a carboxylic and a hydroxyl group; a third functional group can be used by removing a methyl group at the tertiary amino group at the N-terminus.

It is an objective of the present invention to provide novel cytotoxic molecules having spacer systems at different positions which can be used either directly for conjugation by using different conjugation technologies such as chemical conjugation methods known in the art (*BioPharm International* 32-39, December 2003) or enzymatic conjugations using transglutaminases, sortases or other enzymes or which can be used in combination with commonly described linker systems known in the art.

The present invention provides one or more compounds of formula (I):

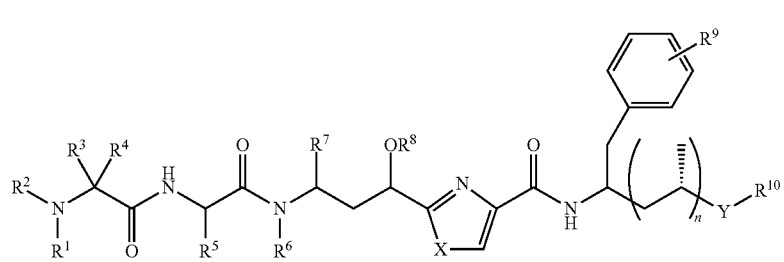

wherein
n is 0 or 1;
X is O or S;
Y is a CO group or a $CH_2$ group or a bond;
$R^2$ and $R^3$ are independently H or an alkyl, cycloalkyl, heteroalkyl or heterocycloalkyl group, all of which may optionally be substituted, or $R^2$ and $R^3$ together are a group of formula $(CH_2)_m$ wherein m is 2, 3, 4 or 5;
$R^4$ is H, an alkyl, cycloalkyl, heteroalkyl or heterocycloalkyl group, all of which may optionally be substituted;
$R^5$ is H, an alkyl, cycloalkyl, heteroalkyl or heterocycloalkyl group, all of which may optionally be substituted;
$R^6$ is H, an alkyl, alkenyl, alkynyl, heteroalkyl, aralkyl or heteroaralkyl group, all of which may optionally be substituted;
$R^7$ is H, an alkyl, alkenyl, alkynyl, heteroalkyl, aralkyl or heteroaralkyl group, all of which may optionally be substituted;
$R^8$ is H, an alkyl, heteroalkyl (e.g. —CO-alkyl) group, aralkyl or heteroaralkyl group, all of which may optionally be substituted;
and either
$R^1$ is H, a heteroalkyl group or a group of formula —$X^1$-$L^1$-$A^1$ or —$X^1$—$CH_2$—$CH_2$—S—S-Py, wherein Py is a 2-pyridyl group; and $R^9$ is H, OH, SH, CN, $NH_2$, $NO_2$, halogen, or an alkyl, heteroalkyl (such as e.g. alkyloxy, alkylamino, dialkylamino or O—CO-alkyl), aryl (such as e.g. phenyl), heteroaryl, aryloxy or heteroaryloxy group, all of which may optionally be substituted; and
$R^{10}$ is OH, $NH_2$, $NHNH_2$, O—$NH_2$, or a heteroalkyl (such as e.g. alkyloxy, alkylamino, dialkylamino, O-alkylamino, O-dialkylamino or O—CO-alkyl), heteroaryl, aryloxy, aralkyloxy, heteroaralkyloxy or heteroaryloxy group, all of which may optionally be substituted;
or
$R^1$ is H, an alkyl group or a heteroalkyl group, all of which may optionally be substituted; and
$R^9$ is H, OH, SH, CN, $NH_2$, $NO_2$, halogen, or an alkyl, heteroalkyl (such as e.g. alkyloxy, alkylamino, dialkylamino or O—CO-alkyl), aryl (such as e.g. phenyl), heteroaryl, aryloxy or heteroaryloxy group, all of which may optionally be substituted; and
$R_{10}$ is a group of formula —$X^2$-$L^2$-$A^2$ or —$X^2$—$CH_2$—$CH_2$—S—S-Py, wherein Py is a 2-pyridyl group or, if Y is a bond, a heteroaryl group;
or
$R^1$ is H, an alkyl group or a heteroalkyl group, all of which may optionally be substituted; and
$R^9$ is a group of formula —$X^3$-$L^3$-$A^3$ or —$X^3$—$CH_2$—$CH_2$—S—S-Py, wherein Py is a 2-pyridyl group; and
$R^{10}$ is OH, $NH_2$, $NHNH_2$, O—$NH_2$, or a heteroalkyl (such as e.g. alkyloxy, alkylamino, dialkylamino, O-alkylamino, O-dialkylamino or O—CO-alkyl), heteroaryl, aryloxy, aralkyloxy, heteroaralkyloxy or heteroaryloxy group, all of which may optionally be substituted;
$X^1$ is a bond or —CO—O—, —CO—, —NH— or —NHCO—O—;
$X^2$ is —NH—NH—CO—O—, —NH—NH—CO—S—, —NH—NH—CO—NH—, —NH—CO—, —NH—NH—, —O—, —O—NH—, —S— or —NH—;
$X^3$ is —O—, —S—, —NH—, —O—NH—, —O—CO—NH—, —O—CO—, —NH—CO—, —NH—CO—O—, —NH—CO—NH—, —NHNHCO—O—, —NHN-HCO—S— or —NHNHCO—NH—;
$L^1$ is a linear, optionally substituted alkylene group containing from 1 to 20 (preferably from 1 to 12; especially preferably from 1 to 7) carbon atoms in the chain or a linear, optionally substituted heteroalkylene group containing from 1 to 50 (e.g. 1 to 20; preferably from 1 to 12; especially preferably from 1 to 7) carbon atoms in the chain and from 1 to 20 (e.g. 1 to 15; preferably from 1 to 10; especially preferably from 1 to 5) oxygen, sulfur and/or nitrogen atoms (preferably oxygen and/or nitrogen atoms), wherein this alkylene or heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene or heteroarylene group(s);

$L^2$ is a linear, optionally substituted alkylene group containing from 1 to 20 (preferably from 1 to 12; especially preferably from 1 to 7) carbon atoms in the chain or a linear, optionally substituted heteroalkylene group containing from 1 to 50 (e.g. 1 to 20; preferably from 1 to 12; especially preferably from 1 to 7) carbon atoms in the chain and from 1 to 20 (e.g. 1 to 15; preferably from 1 to 10; especially preferably from 1 to 5) oxygen, sulfur and/or nitrogen atoms (preferably oxygen and/or nitrogen atoms), wherein this alkylene or heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene or heteroarylene group(s);

$L^3$ is a linear, optionally substituted alkylene group containing from 1 to 20 (preferably from 1 to 12; especially preferably from 1 to 7) carbon atoms in the chain or a linear, optionally substituted heteroalkylene group containing from 1 to 50 (e.g. 1 to 20; preferably from 1 to 12; especially preferably from 1 to 7) carbon atoms in the chain and from 1 to 20 (e.g. 1 to 15; preferably from 1 to 10; especially preferably from 1 to 5) oxygen, sulfur and/or nitrogen atoms (preferably oxygen and/or nitrogen atoms), wherein this alkylene or heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene or heteroarylene group(s);

$A^1$ is OH, SH, $NH_2$, $N_3$ or NH—$C_{1-6}$alkyl, a group of formula —NH—CO—$CH_2$—NH—(CO—$CH_2$—NH—)$_w$CO—$CH_2$—$NH_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group or an optionally substituted aryl group or an optionally substituted aralkyl group, wherein w is an integer of from 1 to 5; and $A^2$ is OH, SH, $NH_2$, $N_3$ or NH—$C_{1-6}$alkyl, a group of formula —NH—CO—$CH_2$—NH—(CO—$CH_2$—NH—)$_w$CO—$CH_2$—$NH_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group or an optionally substituted aryl group or an optionally substituted aralkyl group, wherein w is an integer of from 1 to 5;

$A^3$ is OH, SH, $NH_2$, $N_3$ or NH—$C_{1-6}$alkyl, a group of formula —NH—CO—$CH_2$—NH—(CO—$CH_2$—NH—)$_w$CO—$CH_2$—$NH_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group or an optionally substituted aryl group or an optionally substituted aralkyl group, wherein w is an integer of from 1 to 5;

or a pharmacologically acceptable salt, solvate or hydrate thereof.

The expression alkyl refers to a saturated, straight-chain or branched hydrocarbon group that contains preferably from 1 to carbon atoms, more preferably from 1 to 12 carbon atoms, especially from 1 to 6 (e.g. 1, 2, 3 or 4) carbon atoms, for example methyl (Me), ethyl, propyl, isopropyl, isobutyl, n-butyl, sek-butyl, tert-butyl, n-pentyl, 2,2-dimethylpropyl, 2-methylbutyl, n-hexyl, 2,2-dimethylbutyl or 2,3-dimethylbutyl.

The expressions alkenyl and alkynyl refer to at least partially unsaturated, straight-chain or branched hydrocarbon groups that contain preferably from 2 to 20 carbon atoms, more preferably from 2 to 12 carbon atoms, especially from 2 to 6 (e.g. 2, 3 or 4) carbon atoms, for example an ethenyl, allyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms (e.g. 1, 2 or 3 hydrogen atoms) have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2, 3, 4 or 5) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl (alkyl-CO—), acylalkyl, alkoxycarbonyl, acyloxy, acyloxyalkyl, carboxyalkylamide or alkoxycarbonyloxy. Furthermore, the term heteroalkyl refers to groups in which one or more hydrogen atoms have been replaced by a halogen atom (preferably F or Cl).

Preferably, a heteroalkyl group contains from 1 to 12 carbon atoms and from 1 to 4 heteroatoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) heteroatoms selected from oxygen, nitrogen and sulphur (especially oxygen and nitrogen).

The term $C_1$-$C_8$ heteroalkyl refers to a heteroalkyl group containing from 1 to 8 carbon atoms and 1, 2 or 3 heteroatoms selected from O, S and/or N (especially O and/or N). The term $C_1$-$C_6$ heteroalkyl refers to a heteroalkyl group containing from 1 to 6 carbon atoms and 1, 2 or 3 heteroatoms selected from 0, S and/or N (especially O and/or N). Furthermore, the term heteroalkyl refers to groups in which one or more hydrogen atoms have been replaced by a halogen atom (preferably F or Cl).

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, —$R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ is a hydrogen atom, a $C_1$-$C_6$ alkyl, a $C_2$-$C_6$ alkenyl or a $C_2$-$C_6$ alkynyl group; $R^b$ is a hydrogen atom, a $C_1$-$C_6$ alkyl, a $C_2$-$C_6$ alkenyl or a $C_2$-$C_6$ alkynyl group; $R^c$ is a hydrogen atom, a $C_1$-$C_6$ alkyl, a $C_2$-$C_6$ alkenyl or a $C_2$-$C_6$ alkynyl group; $R^d$ is a hydrogen atom, a $C_1$-$C_6$ alkyl, a $C_2$-$C_6$ alkenyl or a $C_2$-$C_6$ alkynyl group and $Y^a$ is a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by halogen (e.g. fluorine or chlorine) atoms.

Specific examples of heteroalkyl groups are methoxy, trifluoromethoxy, ethoxy, n-propyloxy, isopropyloxy, tert-butyloxy, methoxymethyl, ethoxymethyl, —$CH_2CH_2OH$, —$CH_2OH$, —$CH_2CH_2SH$, —$CH_2SH$, —$CH_2CH_2SSCH_2CH_2NH_2$, —$CH_2CH_2SSCH_2CH_2COOH$, methoxyethyl, methylamino, ethylamino, dimethylamino, diethyl-amino, isopropylethylamino, methylamino methyl, ethylamino methyl, diisopropylamino ethyl, enol ether, dimethylamino methyl, dimethylamino ethyl, acetyl, propionyl, butyryloxy, acetyloxy, methoxycarbonyl, ethoxycarbonyl, N-ethyl-N-methylcarbamoyl or N-methylcarbamoyl. Further examples of heteroalkyl groups are nitrile, isonitrile, cyanate, thio-cyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentyl-cyclohexyl, fluorocyclohexyl or cyclohex-2-enyl group.

The expression heterocycloalkyl refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, $NH_2$, =NH, $N_3$ or $NO_2$ groups.

Examples are a piperidyl, prolinyl, imidazolidinyl, piperazinyl, morpholinyl, urotropinyl, pyrrolidinyl, tetra-hydrothiophenyl, tetrahydropyranyl, tetrahydrofuryl or 2-pyrazolinyl group and also lactames, lactones, cyclic imides and cyclic anhydrides.

The expression alkylcycloalkyl refers to a group that contains both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more (preferably 1, 2 or 3) carbon atoms, each independently, have been replaced by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkyl-heterocycloalkenyl, the cyclic groups being saturated or mono-, di- or tri-unsaturated.

The expression aryl or Ar refers to an aromatic group that contains one or more rings containing from 6 to 14 ring carbon atoms, preferably from 6 to 10 (especially 6) ring carbon atoms. The expression aryl (or Ar, respectively) refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to a group containing both aryl and also alkyl, alkenyl, alkynyl and/or cycloalkyl groups in accordance with the above definitions, such as, for example, an arylalkyl, arylalkenyl, arylalkynyl, arylcycloalkyl, aryl-cycloalkenyl, alkylarylcycloalkyl and alkylarylcycloalkenyl group. Specific examples of aralkyls are toluene, xylene, mesitylene, styrene, benzyl chloride, o-fluorotoluene, 1H-indene, tetraline, dihydronaphthalene, indanone, phenyl-cyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms, each independently, have been replaced by an oxygen, nitrogen, silicon, selenium, phosphorus, boron or sulfur atom (preferably oxygen, sulfur or nitrogen), that is to say to a group containing both aryl and/or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroaryl-heteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The term "optionally substituted" especially relates to groups that are optionally substituted by fluorine, chlorine, bromine or iodine atoms or by OH, =O, SH, =S, $NH_2$, =NH, $N_3$ or $NO_2$ groups. This term further preferably relates to groups, which can be exclusively or additionally substituted with unsubstituted $C_1$-$C_6$ alkyl, $C_2$-$C_6$ alkenyl, $C_2$-$C_6$ alkinyl or $C_1$-$C_6$ heteroalkyl groups, or with an aryl group containing 6 or 10 ring atoms or a heteroaryl group containing 5 or 6 to 9 or 10 ring atoms.

The term halogen preferably refers to F, Cl, Br or I.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Protecting groups are known to a person skilled in the art and e.g. described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999. Common amino protecting groups are e.g. t-butyloxycarbonyl (Boc), t-butyldimethylsilyl (TBS), benzyl-oxycarbonyl (Cbz, Z), benzyl (Bn), benzoyl (Bz), fluorenylmethyloxycarbonyl (Fmoc), allyloxycarbonyl (Alloc), triethylsilyl (TES), trichlorethyloxycarbonyl (Troc), acetyl or trifluoracetyl.

Compounds of formula (I), (II), (III) and (IV) may comprise several chiral centers depending on their substitution pattern. The present invention relates to all defined enantio- and diastereoisomers as well as their mixtures in all ratios.

Moreover, the present invention relates to all, cis/trans isomers of compounds of general formula (I), (II), (III) and (IV) as well as their mixtures. Moreover, the present invention relates to all tautomeric forms of compounds of the general formula (I), (II), (III) and (IV). Preferably, compounds of formula (I), (II), (III) and (IV) have the same stereochemistry as naturally occurring tubulysin A.

Preferably, $R^2$ is H or a $C_{1-6}$ alkyl group.

Further preferably, $R^3$ is H or a $C_{1-6}$ alkyl group.

Especially preferably, $R^2$ and $R^3$ together are a group of formula $(CH_2)_m$ wherein m is 3 or 4. Especially preferably, m is 4.

Further preferably, $R^4$ is hydrogen.

Moreover preferably, $R^5$ is a $C_{1-6}$ alkyl group. Especially preferably, $R^5$ is an iso-butyl group.

Further preferably, $R^7$ is a $C_{1-6}$ alkyl group. Especially preferably, $R^7$ is an iso-propyl group.

Moreover preferably, n is 1.

Further preferably, Y is a CO group or a $CH_2$ group (especially a CO group).

Further preferred are compounds of formula (II):

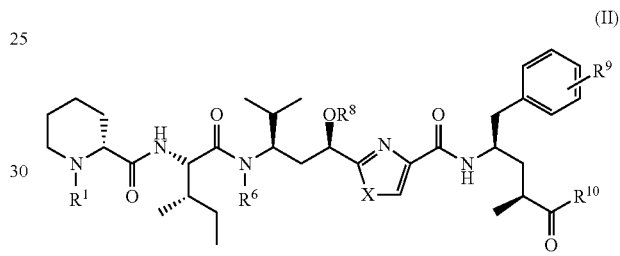

(II)

wherein $R^1$, $R^6$, $R^8$, $R^9$, $R^{10}$ and X are as defined above for compounds of formula (I), or a pharmacologically acceptable salt, solvate or hydrate thereof.

Preferred embodiments of compounds of formula (I) and/or (II):

Preferably, $R^6$ is a $C_{1-6}$ alkyl group or a $C_{1-8}$ heteroalkyl group.

Moreover preferably, $R^6$ is a $C_{1-6}$ alkyl group, a group of formula —$CH_2CH_2OH$ or a group of formula $CH_2OR^{61}$ or $CH_2OCOR^{62}$, wherein $R^{61}$ is $C_{1-6}$ alkyl and $R^{62}$ is $C_{1-6}$ alkyl, $C_2$-$C_6$ alkenyl, phenyl, or $CH_2$-Phenyl.

Especially preferably, $R^6$ is a $C_{1-6}$ alkyl group, a group of formula —$CH_2$—O—$C_{1-6}$alkyl or a group of formula —$CH_2$—O—CO—$C_{1-6}$alkyl or a group of formula —$CH_2CH_2OH$.

Most preferably, $R^6$ is a $C_1$-$C_6$ alkyl group (especially a group of formula —$CH_2CH_2CH_3$).

Moreover preferably, $R^8$ is H, acetyl (—CO—$CH_3$), —$CH_2OCH_3$ or a $C_{1-6}$ alkyl group.

Especially preferably, $R^8$ is a $C_{1-6}$ alkyl group (especially a group of formula —$CH_2CH_2CH_3$).

Further preferably, X is S.

Further preferably, if $R^1$ is not a group of formula —$X^1$-$L^1$-$A^1$ or —$X^1$—$CH_2$—$CH_2$—S—S-Py, $R^1$ is hydrogen, a methyl group or a group of formula —CO—$CH_2$—NH—$CH_3$; especially preferably hydrogen or a methyl group; most preferably, a methyl group.

According to a further preferred embodiment, $R^1$ is a heteroalkyl group (especially a group of formula —CO—$CH_2$—NH—$CH_3$).

Moreover preferably, if $R^9$ is not a group of Formula $-X^3-L^3-A^3$ or $-X^3-CH_2-CH_2-S-S-Py$, $R^9$ is H, OH, SH, F, CN, $NH_2$, Ph, Me, OMe, $CF_3$, OAc, NHMe or $NMe_2$; especially H, OH or F.

Moreover preferably, if $R^{10}$ is not a group of Formula $-X^2-L^2-A^2$ or $-X^2-CH_2-CH_2-S-S-Py$, $R^{10}$ is OH, a group of formula $O-C_{1-6}alkyl$, $O-CH_2$-phenyl or a tetrazolyl group (especially a 5-tetrazolyl group).

Further preferably, if $R^{10}$ is not a group of Formula $-X^2-L^2-A^2$ or $-X^2-CH_2-CH_2-S-S-Py$ and if n is 0 or 1 and if Y is CO or $CH_2$, $R^{10}$ is OH, a group of formula $O-C_{3-6}alkyl$ or $O-CH_2$-phenyl (especially OH).

Moreover preferably, if $R^{10}$ is not a group of Formula $-X^2-L^2-A^2$ or $X^2-CH_2-CH_2-S-S-Py$ and if n is 0 and if Y is a bond, $R^{10}$ is a tetrazolyl group (especially a 5-tetrazolyl group).

Further preferably, $X^1$ is $-CO-$ or $-CO-O-$ (especially $-CO-O-$).

Moreover preferably, $X^2$ is $-NH-NH-CO-O-$, $-NH-NH-$, $-NH-$, or $-NH-CO-$ (especially $-NH-NH-CO-O-$, $-NH-NH-$ or $-NH-$). Most preferably, $X^2$ is $-NH-NH-CO-O-$.

Further preferably, $X^3$ is $-O-$, $-NH-$, $-NH-CO-$ or $-O-CO-NH-$ (especially $-O-$ or $-NH-$).

Moreover preferably, $L^1$ is a linear, optionally substituted heteroalkylene group containing from 1 to 30 (e.g. 1 to 20; preferably from 1 to 12; especially preferably from 1 to 7) carbon atoms in the chain and from 1 to 15 (preferably from 1 to 10; especially preferably from 1 to 5) oxygen and/or nitrogen atoms, wherein this heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene group(s).

Further preferably, $L^2$ is a linear, optionally substituted heteroalkylene group containing from 1 to 30 (e.g. 1 to 20; preferably from 1 to 12; especially preferably from 1 to 7) carbon atoms in the chain and from 1 to 15 (preferably from 1 to 10; especially preferably from 1 to 5) oxygen and/or nitrogen atoms, wherein this heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene group(s).

Moreover preferably, $L^3$ is a linear, optionally substituted heteroalkylene group containing from 1 to 30 (e.g. 1 to 20; preferably from 1 to 12; especially preferably from 1 to 7) carbon atoms in the chain and from 1 to 15 (preferably from 1 to 10; especially preferably from 1 to 5) oxygen and/or nitrogen atoms, wherein this heteroalkylene group may preferably optionally be substituted by one or more alkyl group(s), heteroalkyl group(s), =O, OH, or $NH_2$ group(s), and wherein this linear alkylene or heteroalkylene group may contain in its chain one or more (especially one or two) arylene group(s).

Further preferably, $L^1$ is $-(CH_2)_r-$, $-(CO-CH_2-NH)_v-CO-CH_2-$ or $-(CH_2CH_2O)_g-CH_2CH_2-$, wherein r is an integer of from 1 to 10, v is an integer of from 1 to 10 and wherein g is an integer of from 0 to 12.

Moreover preferably, $L^2$ is $-(CH_2)_s-$, $-(CO-CH_2-NH)_x-CO-CH_2-$ or $-(CH_2CH_2O)_p-CH_2CH_2-$, wherein s is an integer of from 1 to 10, x is an integer of from 1 to 10 and wherein p is an integer of from 0 to 12.

Further preferably $L^3$ is $-(CH_2)_o-$, $-(CO-CH_2-NH)_y-CO-CH_2-$ or $-(CH_2CH_2O)_q-CH_2CH_2-$, wherein o is an integer of from 1 to 10, y is an integer of from 1 to 10 and q is an integer of from 0 to 12.

Moreover preferably, $L^1$, $L^2$ or $L^3$ are a group of formula:

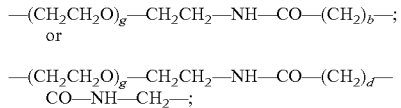

wherein b is an integer of from 1 to 10, d is an integer of from 1 to 10 and wherein g is an integer of from 0 to 12.

Further preferably, $L^1$, $L^2$ or $L^3$ are a group of the following formula:

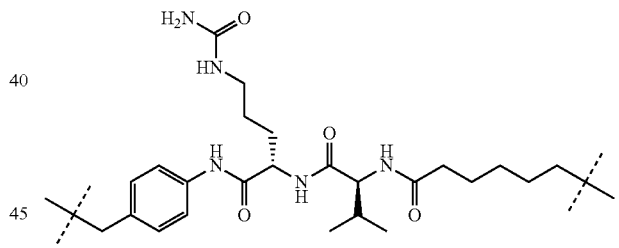

wherein preferably $A^1$, $A^2$ or $A^3$ are bound to the right side of this group.

Moreover preferably, $L^1$, $L^2$ or $L^3$ are a group of the following formula:

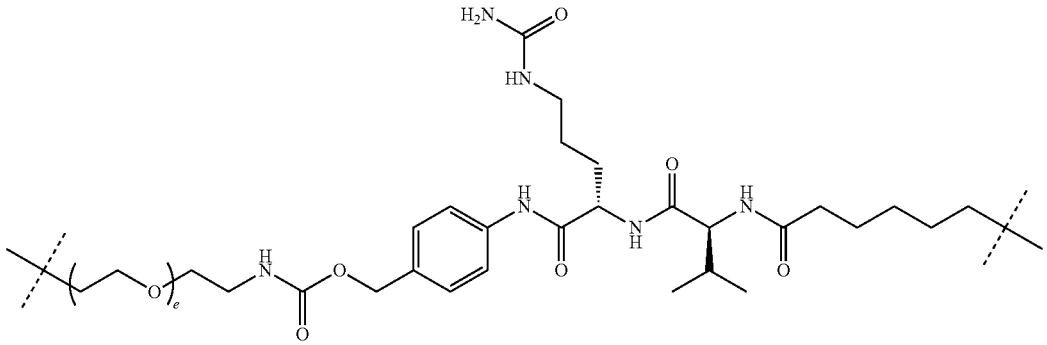

wherein e is an integer of from 0 to 10 (preferably 1 to 5) and wherein preferably $A^1$, $A^2$ or $A^3$ are bound to the right side of this group.

Moreover preferably, $L^1$, $L^2$ or $L^3$ comprise a group of the following formula:

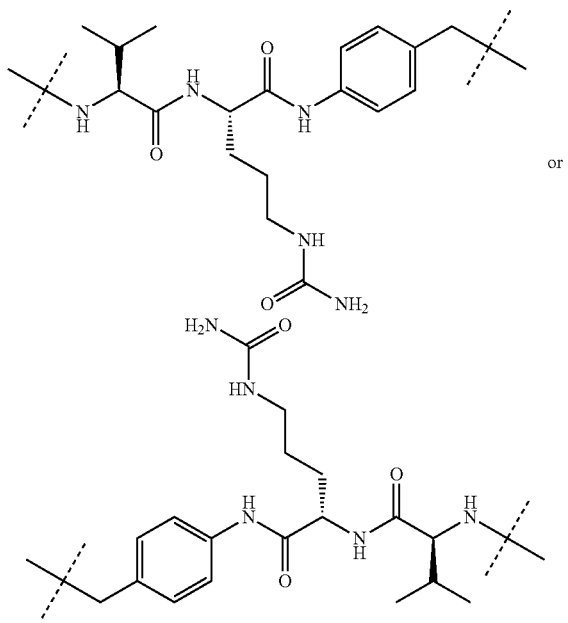

or

Preferably, $A^1$ is $NH_2$, $N_3$ or $NH—C_{1-6}$alkyl, a group of formula —NH—CO—CH$_2$—NH—(CO—CH$_2$—NH—)$_w$CO—CH$_2$—NH$_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group, wherein w is an integer of from 1 to 5.

Further preferably, $A^2$ is $NH_2$, $N_3$ or $NH—C_{1-6}$alkyl, a group of formula —NH—CO—CH$_2$—NH—(CO—CH$_2$—NH—)$_w$CO—CH$_2$—NH$_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group, wherein w is an integer of from 1 to 5.

Moreover preferably, $A^3$ is $NH_2$, $N_3$ or $NH—C_{1-6}$alkyl, a group of formula —NH—CO—CH$_2$—NH—(CO—CH$_2$—NH—)$_w$CO—CH$_2$—NH$_2$, or a $C_2$-$C_6$ alkynyl group or an optionally substituted heteroaryl group or an optionally substituted heterocycloalkyl group or an optionally substituted heteroalkylcycloalkyl group or an optionally substituted heteroaralkyl group, wherein w is an integer of from 1 to 5.

Moreover preferably, $A^1$ is —NH$_2$, —N$_3$, —NHMe or —C≡CH or a maleimidyl group or a group of the following formula:

Further preferably, $A^2$ is —NH$_2$, —N$_3$, —NHMe or —C≡CH or a maleimidyl group or a group of the following formula:

Moreover preferably, $A^3$ is —NH$_2$, —N$_3$, —NHMe or —C≡CH or a maleimidyl group or a group of the following formula:

Especially preferably, group $R^1$ is selected from the following groups:

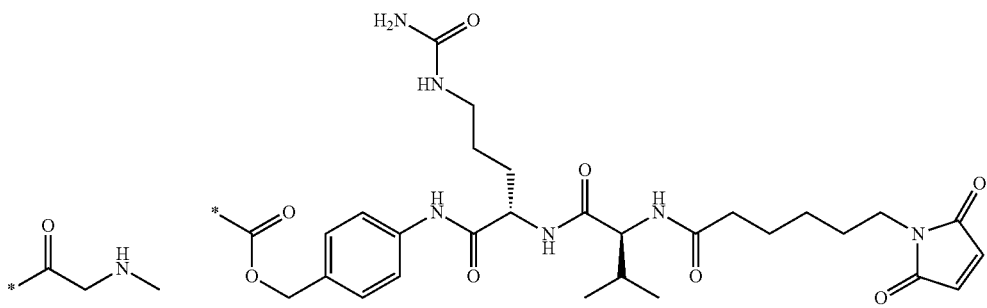

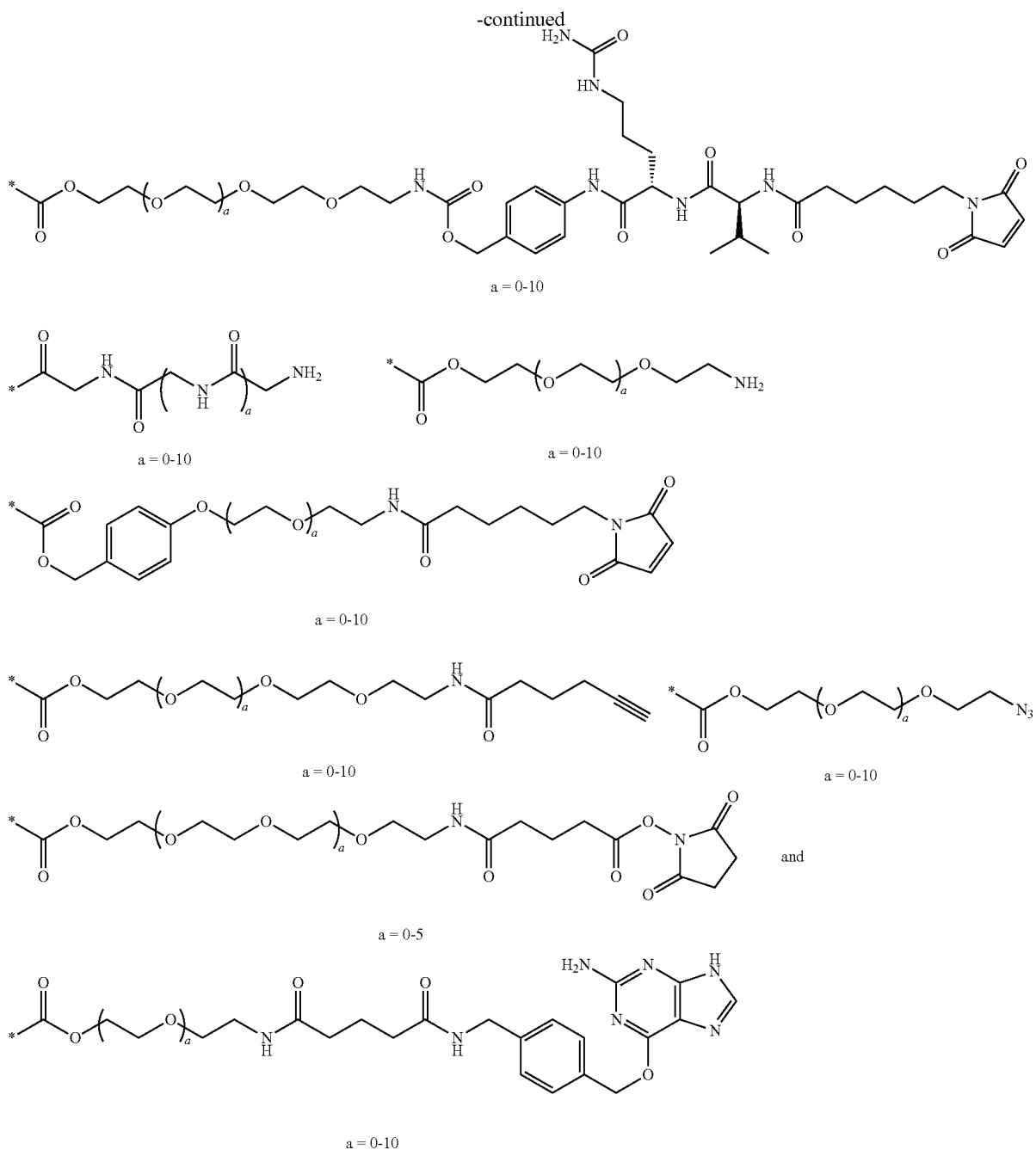
wherein * denotes the point of attachment to the compound of formula (I), (II), (III) or (IV).
Moreover especially preferably, group $R^{10}$ is selected from the following groups:
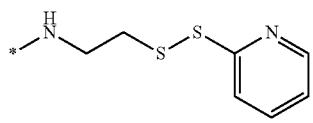 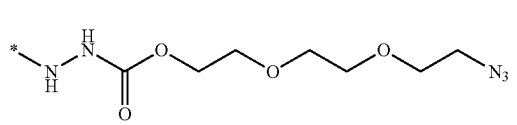
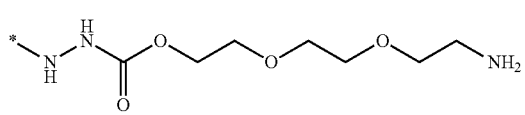 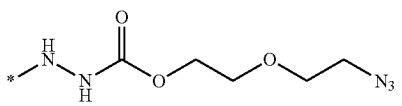

-continued
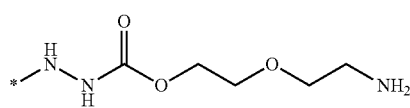
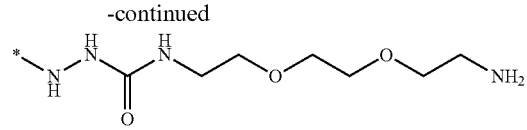
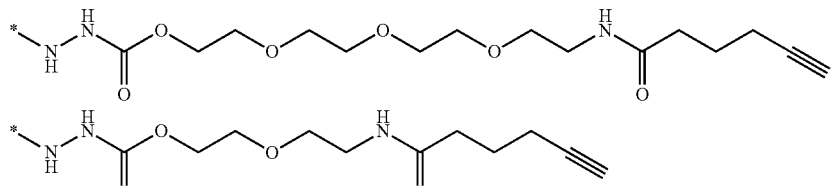
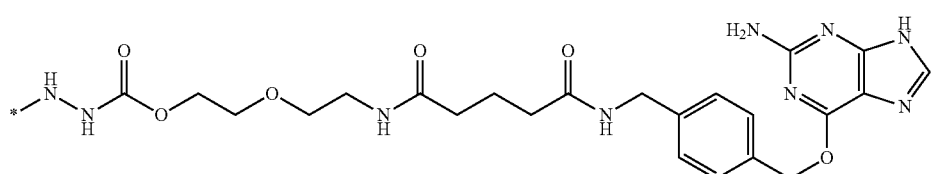
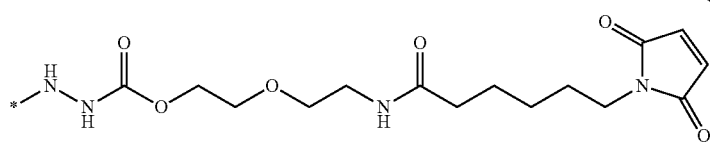
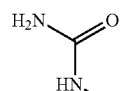
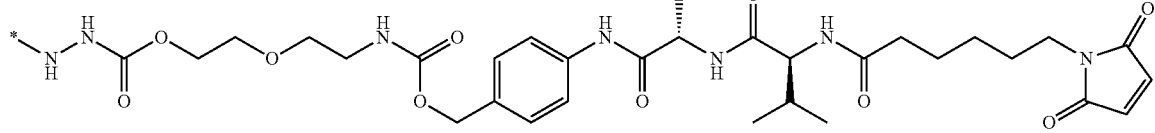
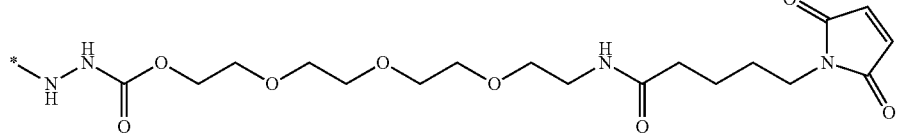
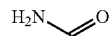
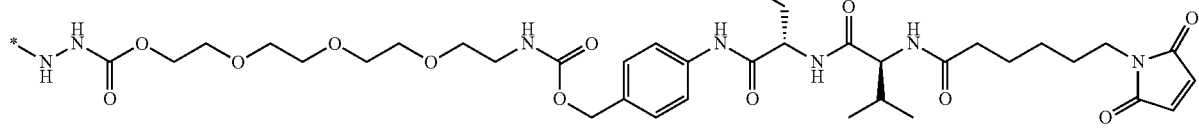
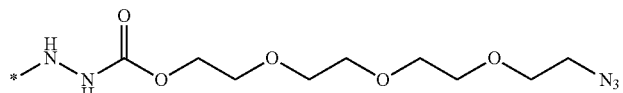
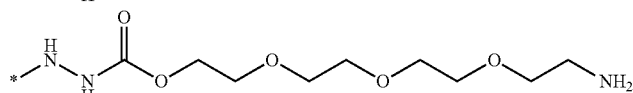
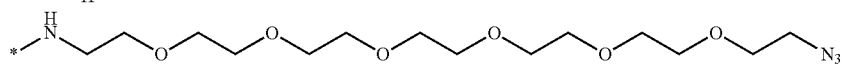

-continued
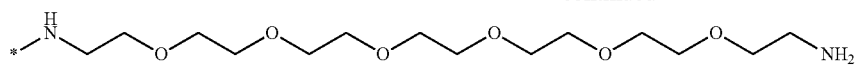
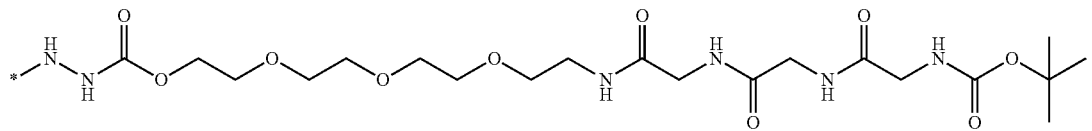
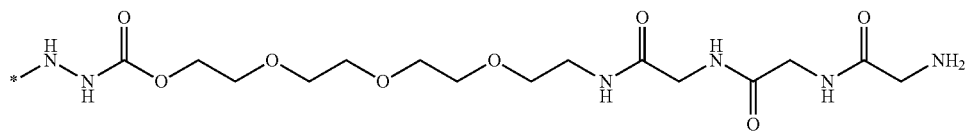
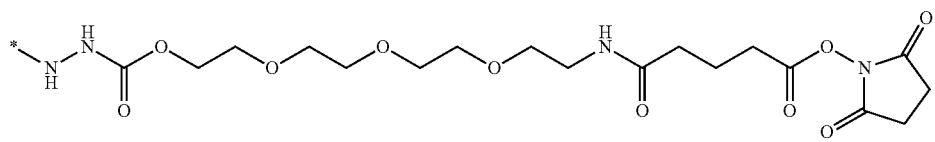
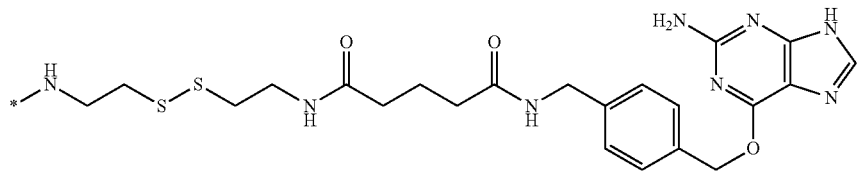
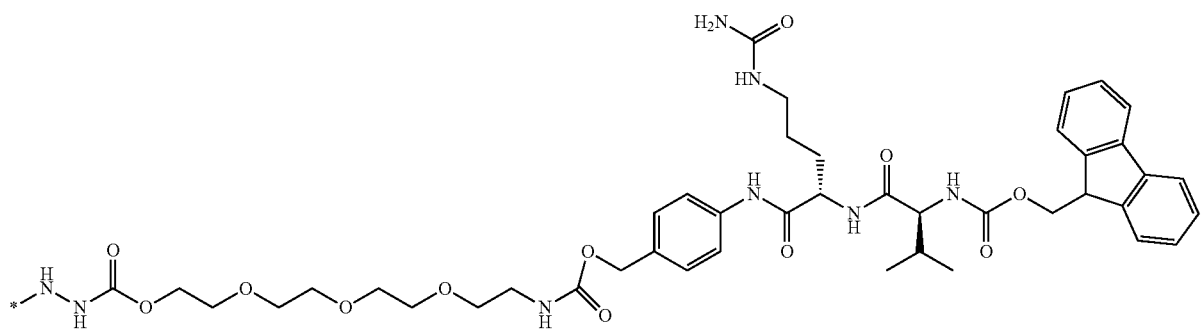
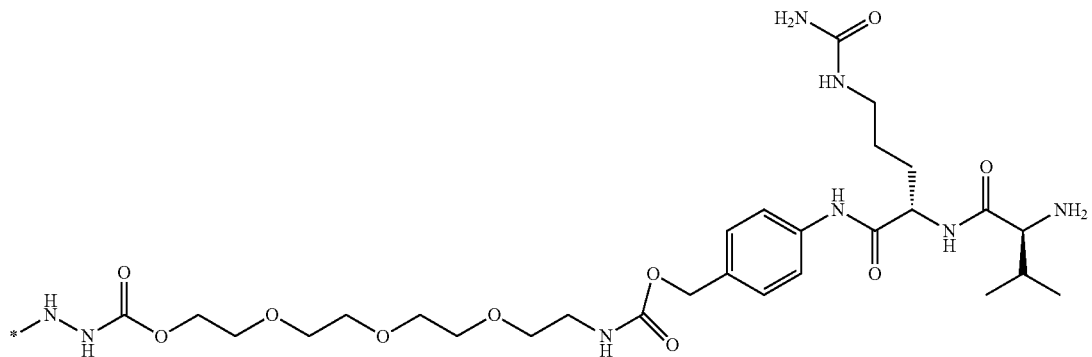

-continued
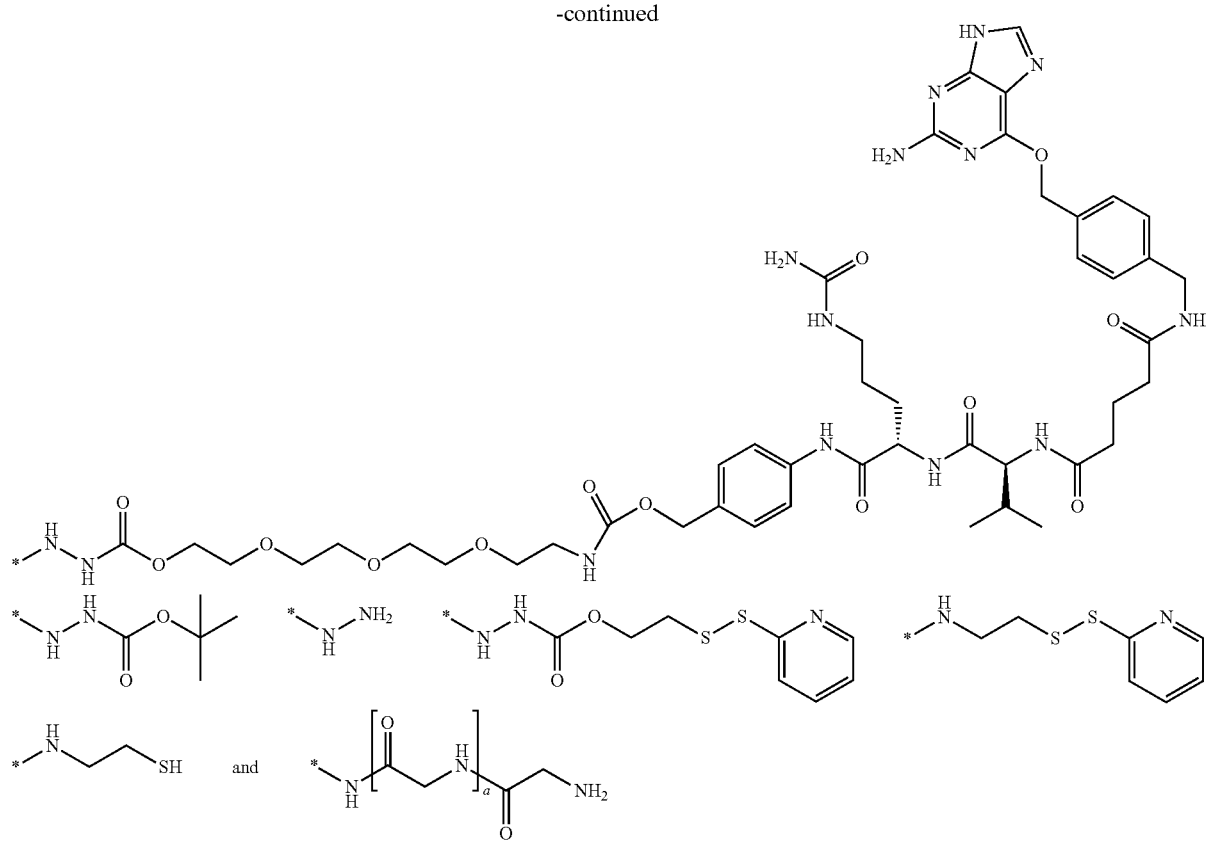
(wherein a is 0 to 7)
wherein * denotes the point of attachment to the compound of formula (I), (II) or (IV).
Moreover especially preferably, group $R^9$ is selected from the following groups:
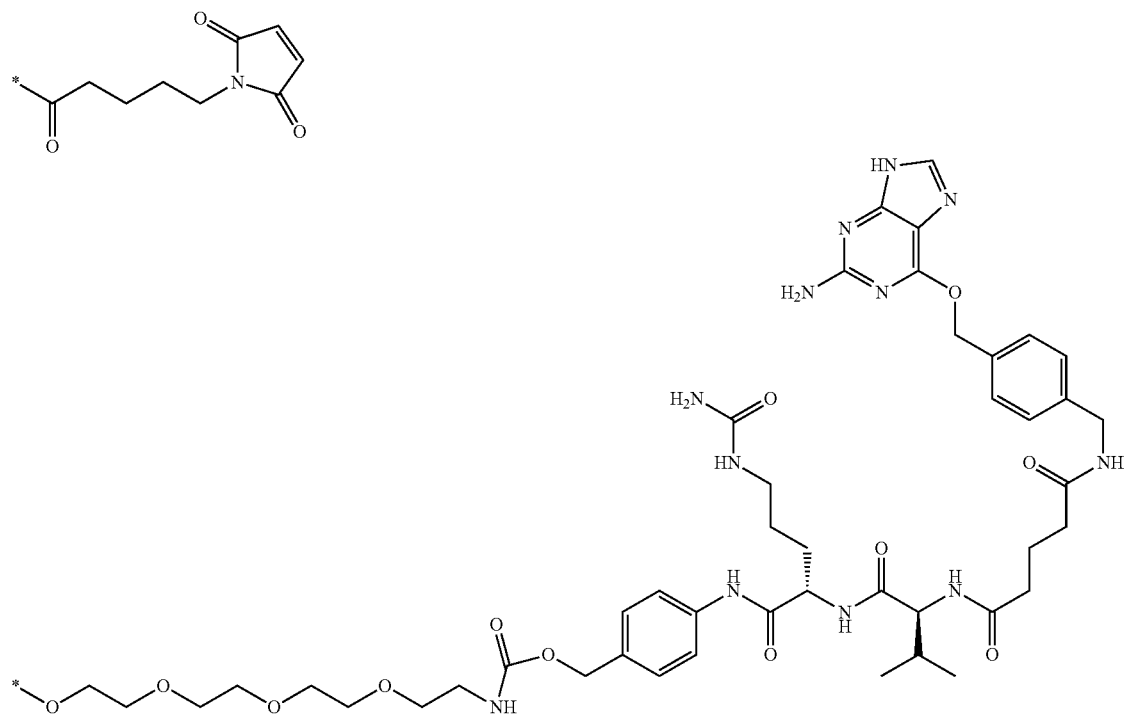

-continued

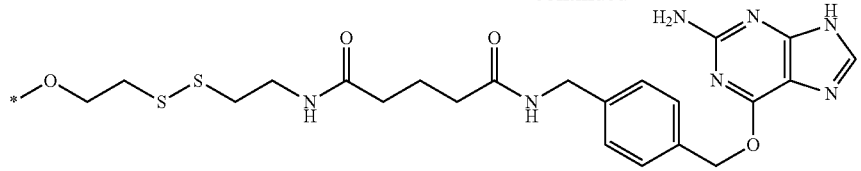

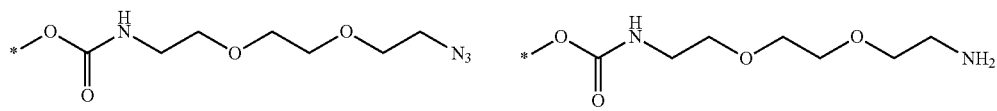

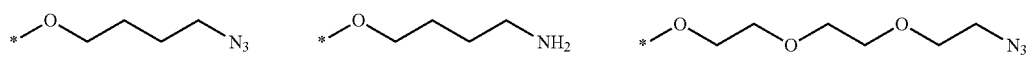

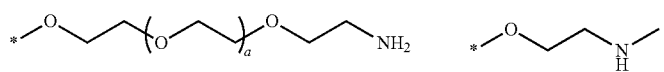

a = 0-10

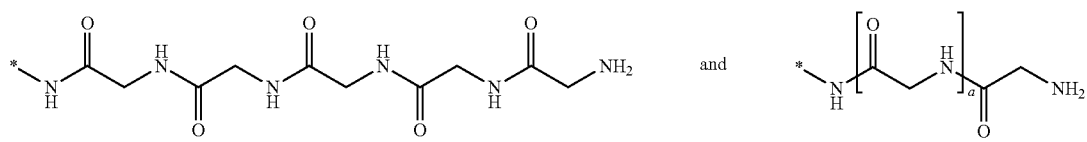

and (wherein a is 0 to 7)
wherein * denotes the point of attachment to the compound of formula (I), (II), (III) or (IV).

Moreover preferred are compounds of formula (III):

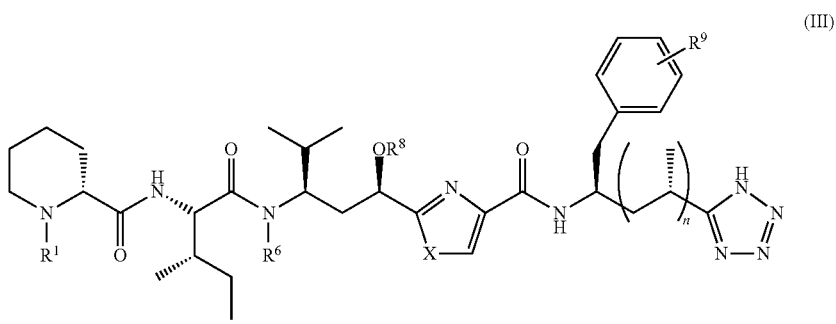

(III)

wherein n, X, $R^1$, $R^6$, $R^8$ and $R^9$ are as defined above for compounds of formula (I) and (II), or a pharmacologically acceptable salt, solvate or hydrate thereof.

Especially preferred are compounds of formula (III), wherein
$R^1$ is hydrogen, a methyl group or a heteroalkyl group (especially a methyl group);
$R^6$ is a $C_{1-6}$ alkyl group or a group of formula $CH_2OR^{61}$ or $CH_2OCOR^{62}$, wherein $R^{61}$ is $C_{1-6}$ alkyl and $R^{62}$ is $C_{1-6}$ alkyl, $C_2-C_6$ alkenyl, phenyl, or $CH_2$-Phenyl;
$R^8$ is H, an acetyl, a —$CH_2OCH_3$ or a $C_{1-6}$ alkyl group;
$R^9$ is H, OH, SH, F, CN, $NH_2$, Ph, Me, OMe, $CF_3$, OAc, NHMe or $NMe_2$;
n is 0 or 1; and
X is S.

Moreover preferred are compounds of formula (IV):

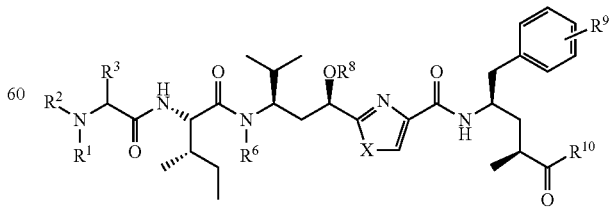

(IV)

wherein X, $R^1$, $R^6$, $R^8$, $R^9$ and $R^{10}$ are as defined above for compounds of formula (I) and (II), $R^2$ is a $C_{1-6}$ alkyl group and R³ is a C₁₋₆ alkyl group or a pharmacologically acceptable salt, solvate or hydrate thereof.

Especially preferred are compounds of formula (IV) wherein R² is a methyl group and R³ is a group of formula —CH(CH₃)CH₂CH₃.

Moreover especially preferred are compounds of formula (I), (II), (III) and (IV), wherein X is S, R⁶ is a C₁₋₆ alkyl group (especially a n-propyl group) and R⁸ is a C₁₋₆ alkyl group (especially a n-propyl group).

Especially preferred compounds of formula (I), (II), (III) and/or (IV) are:

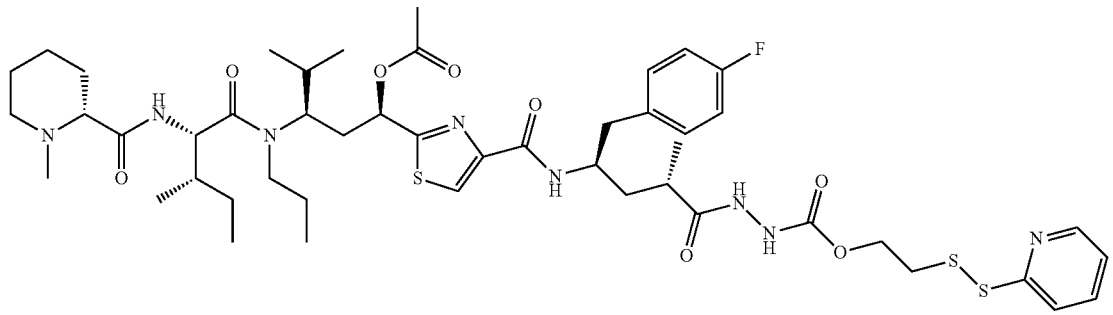

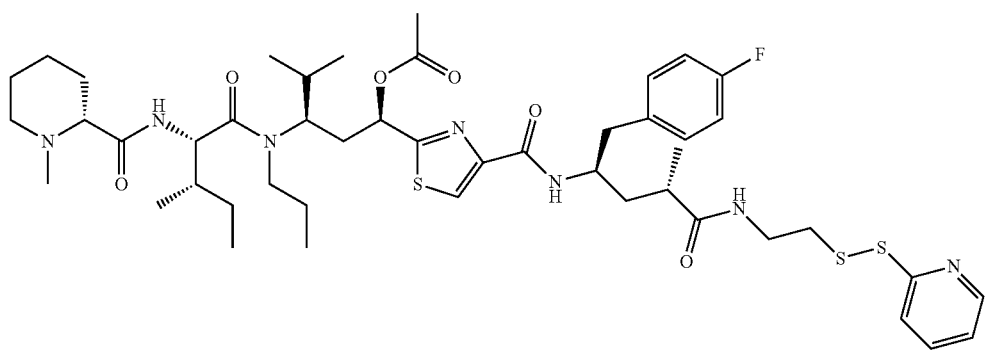

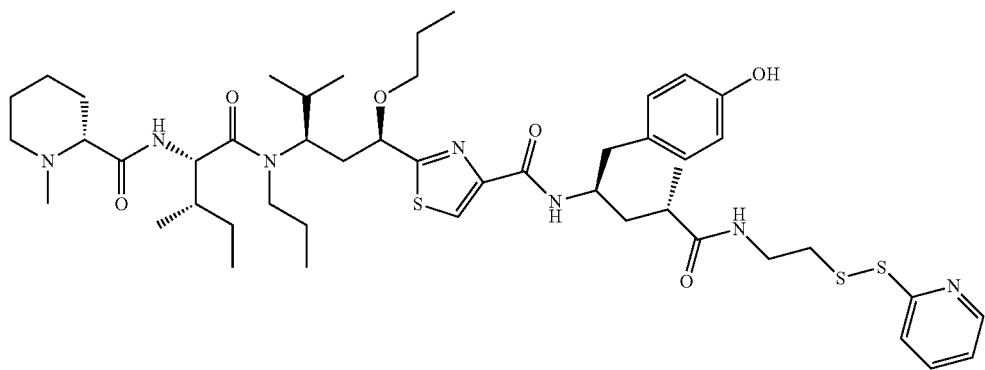

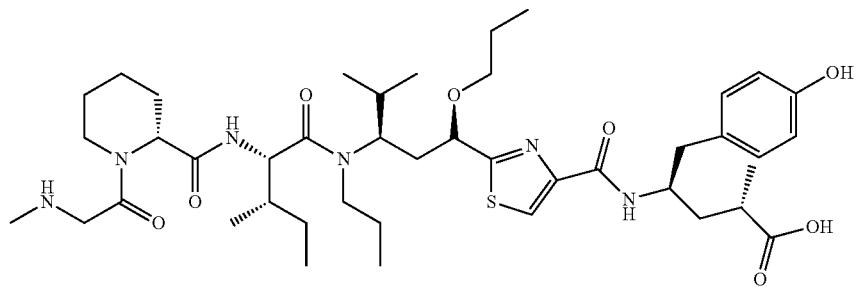

-continued
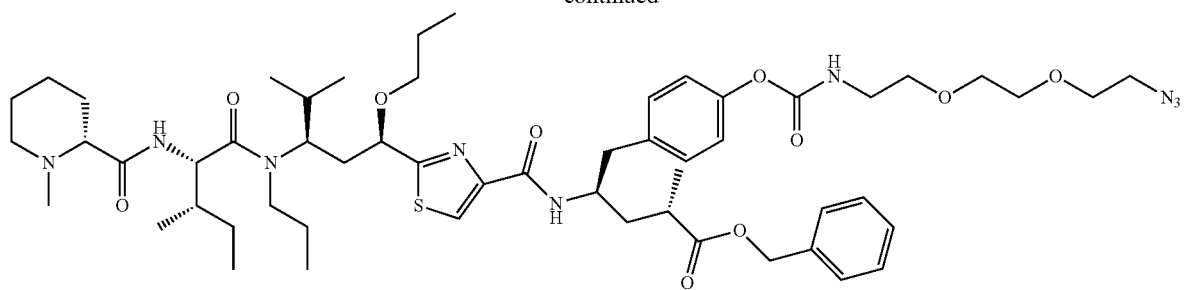
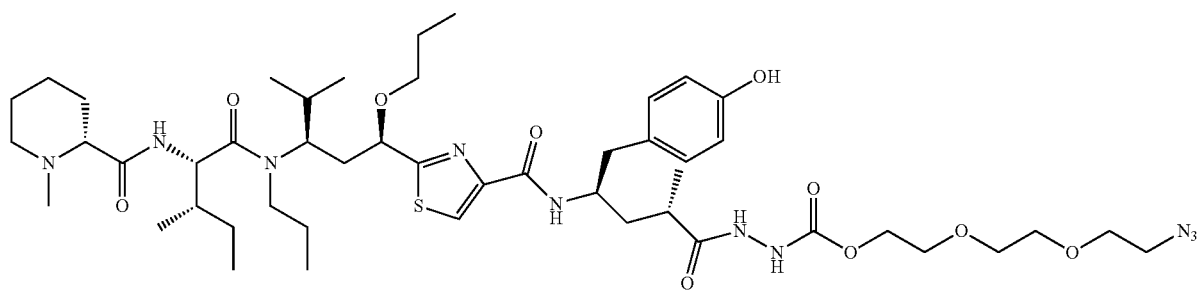
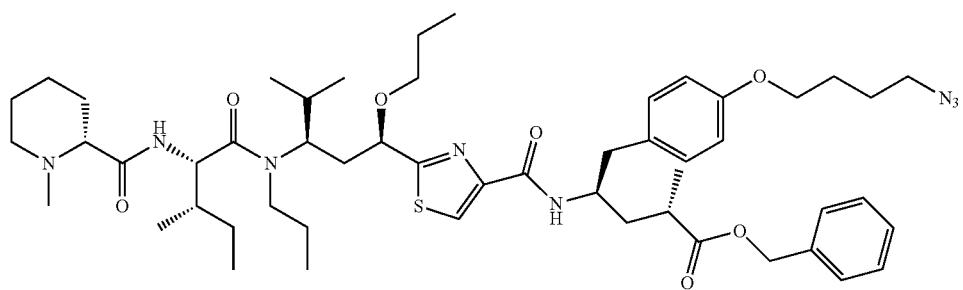
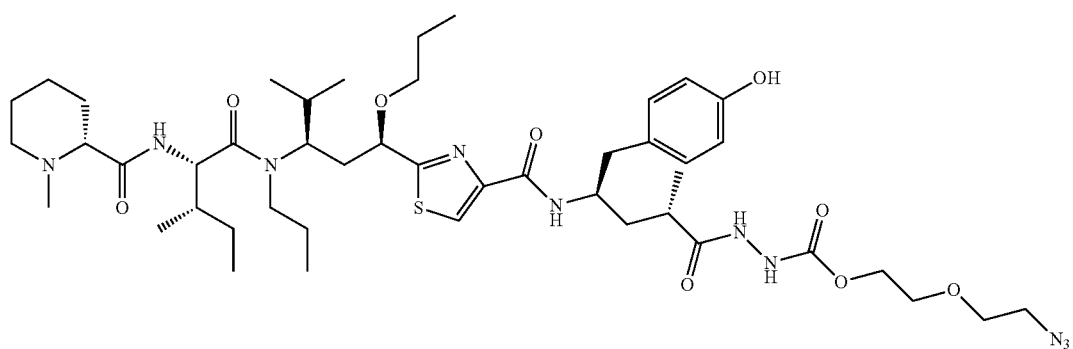
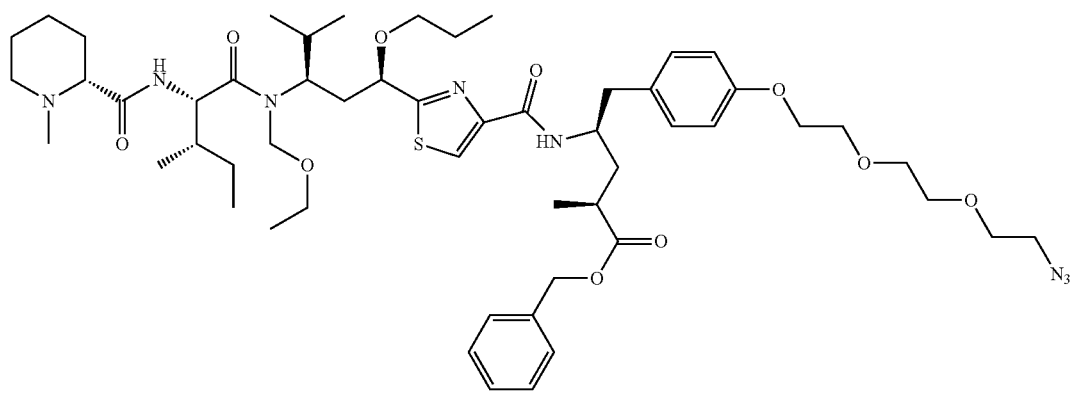

-continued
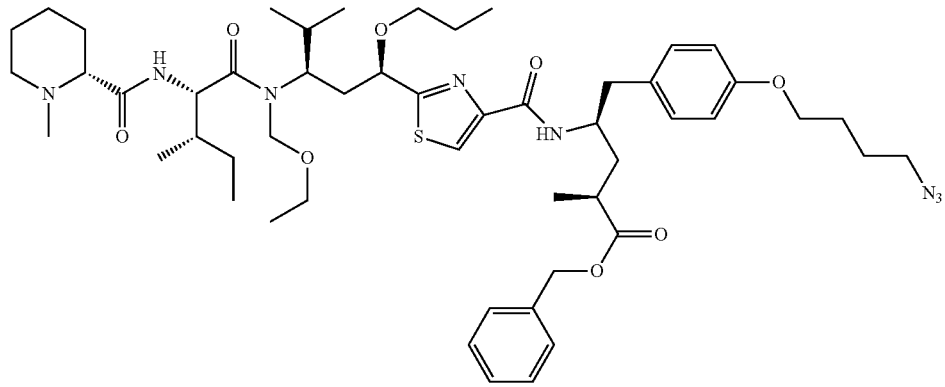
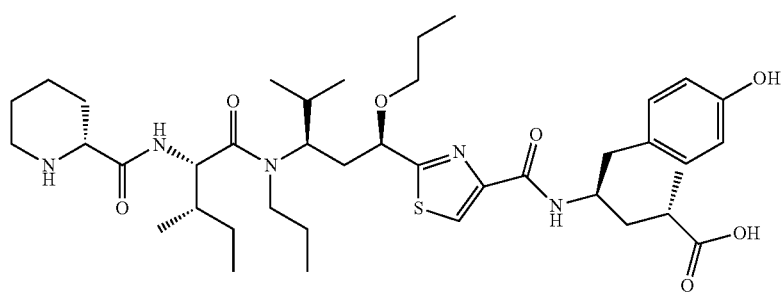
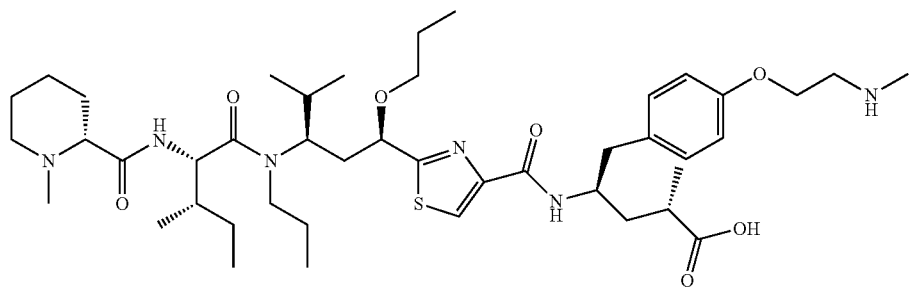
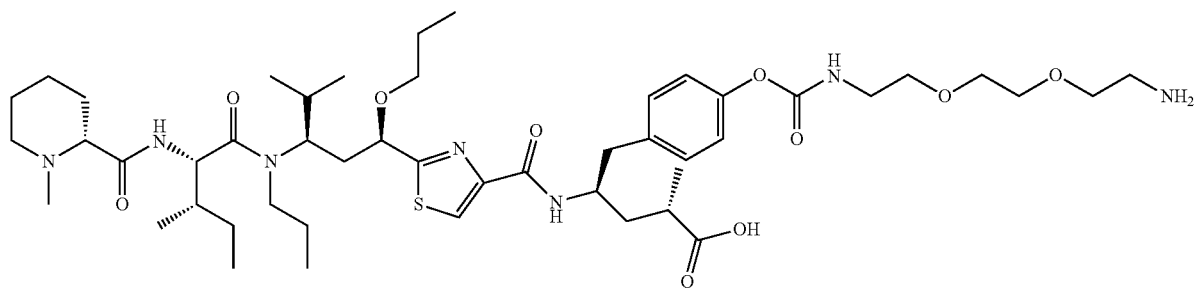
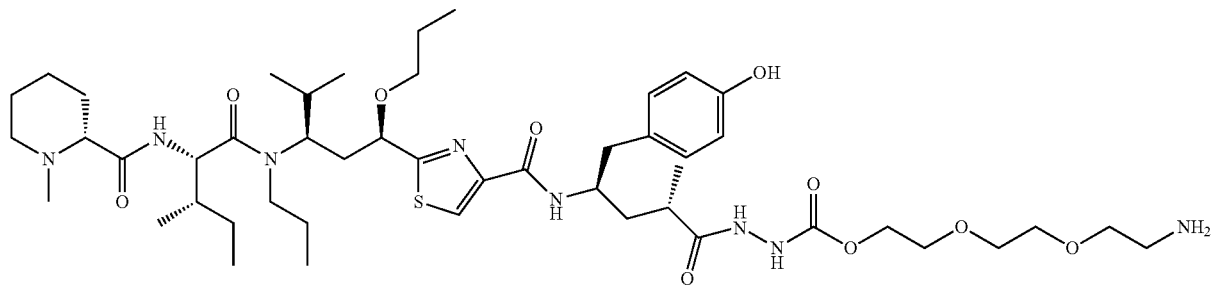

-continued
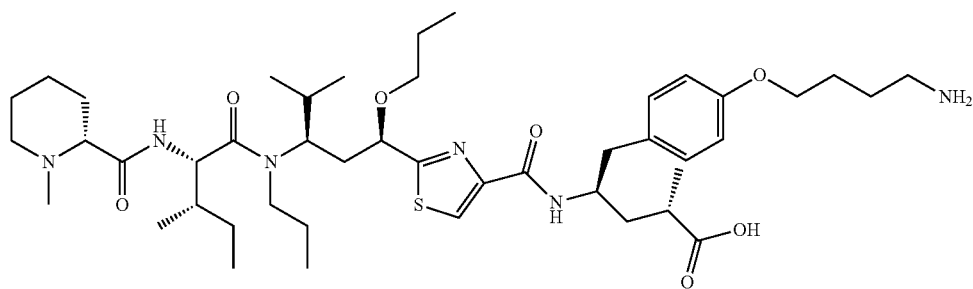
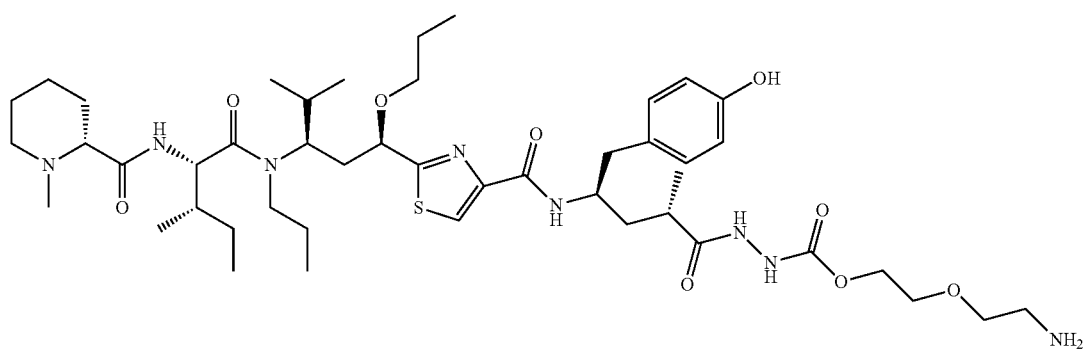
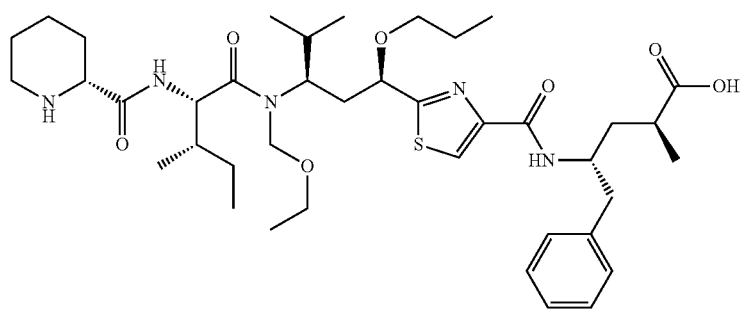
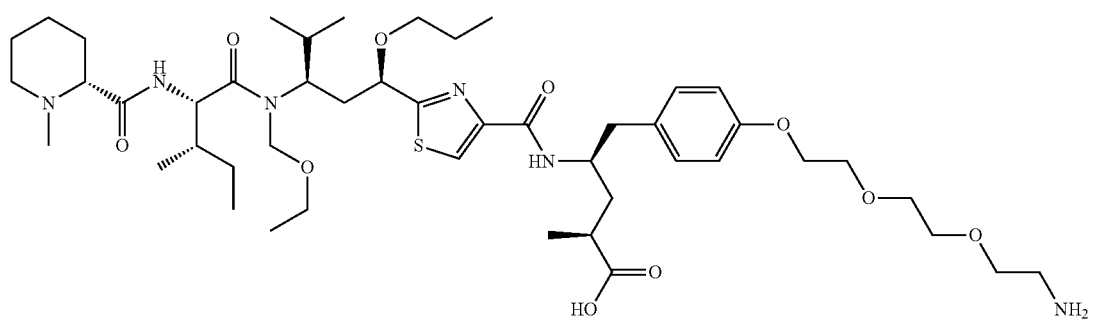
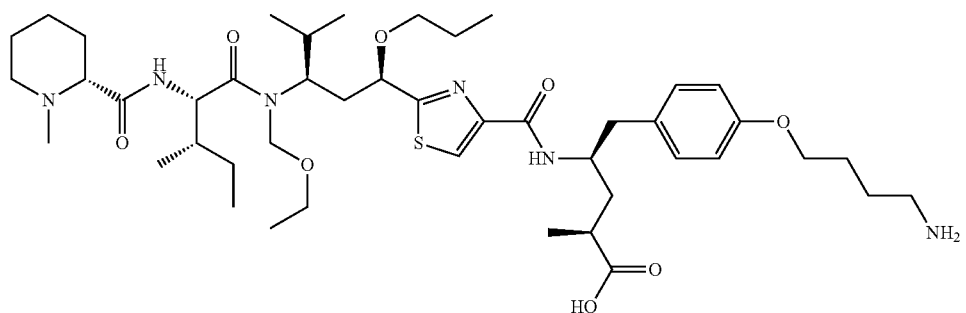

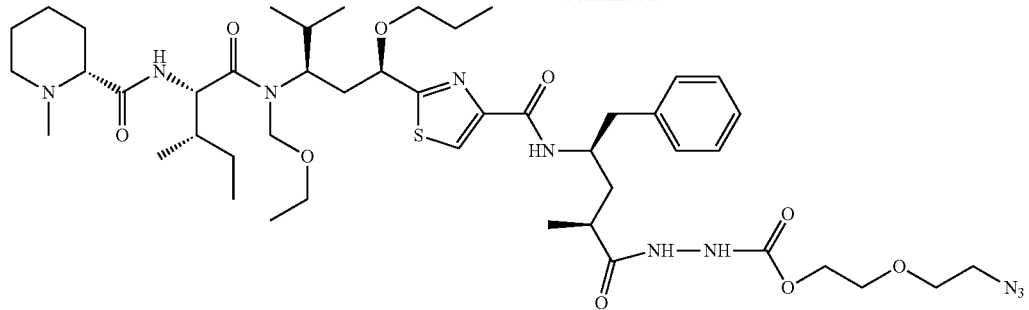
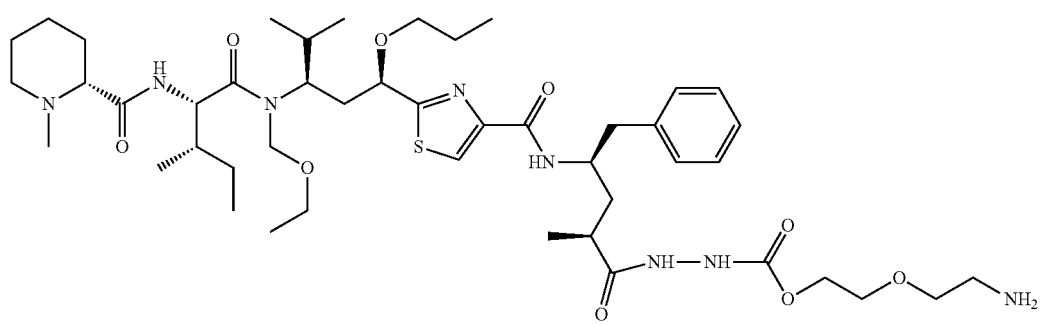
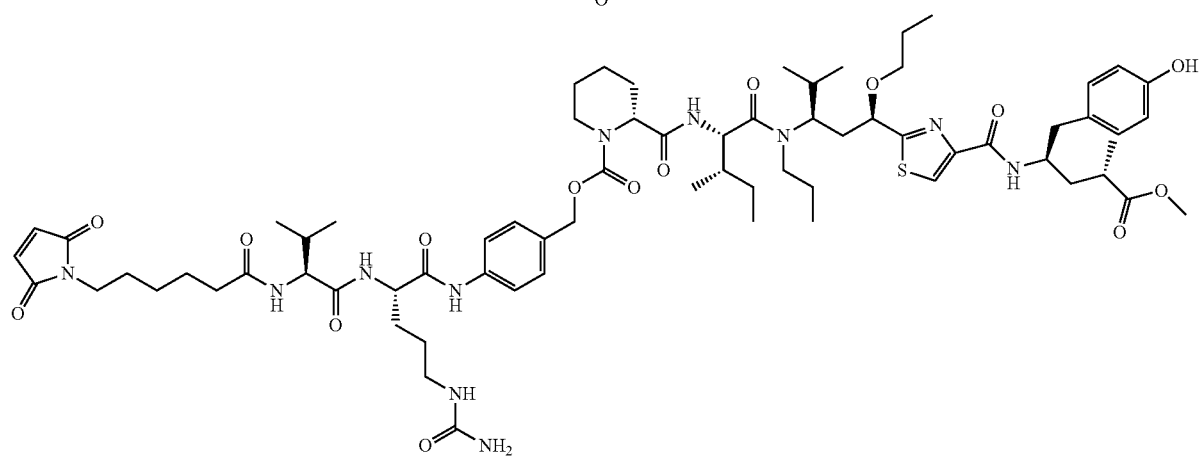
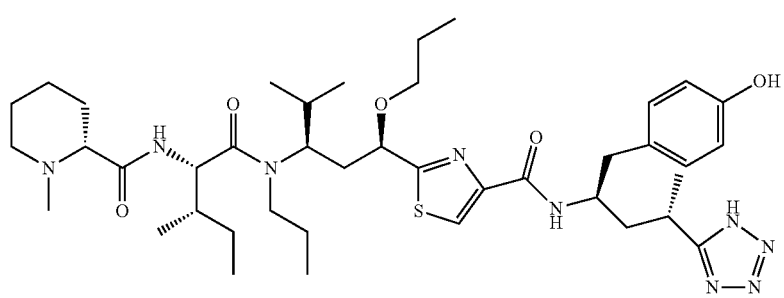
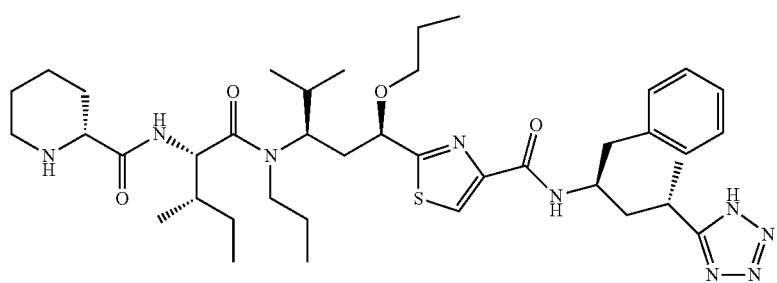

-continued
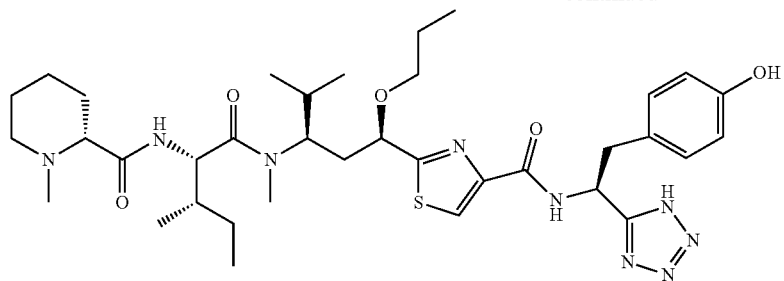
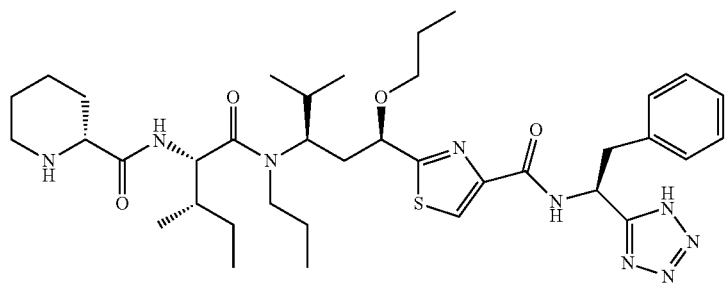
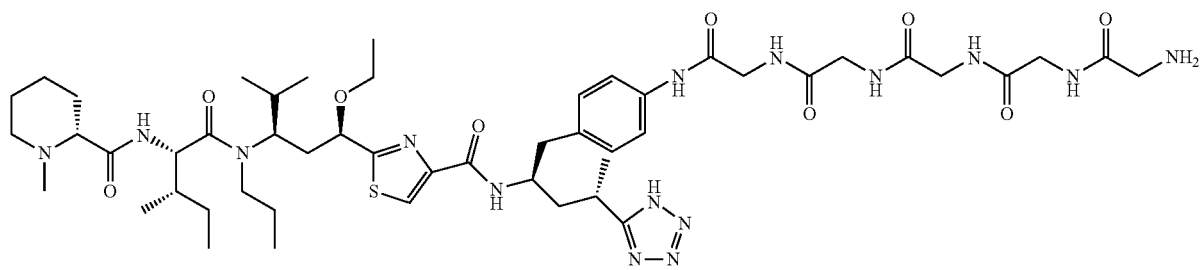
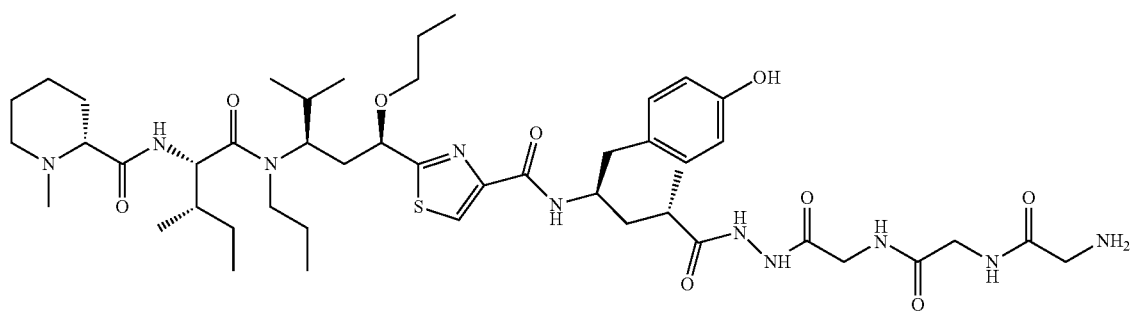
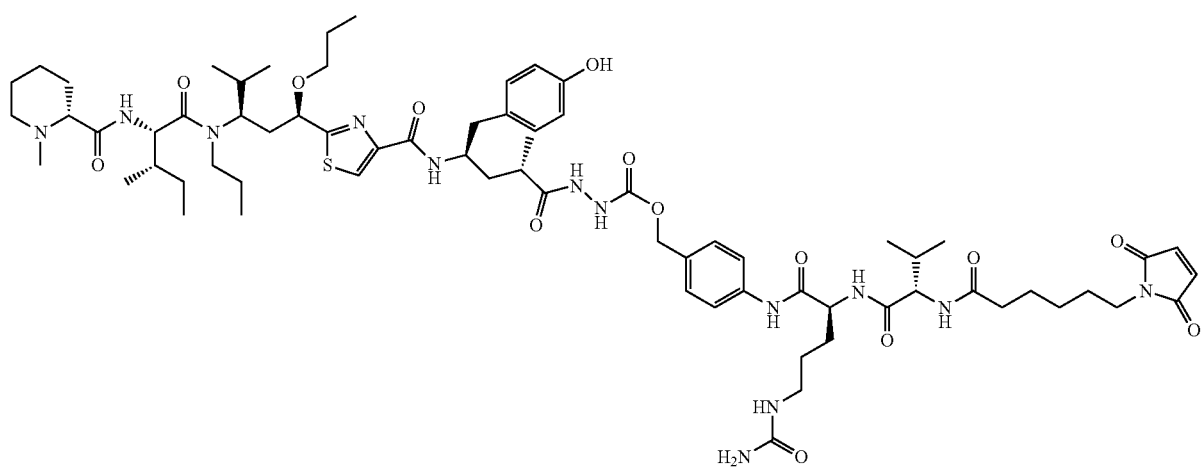

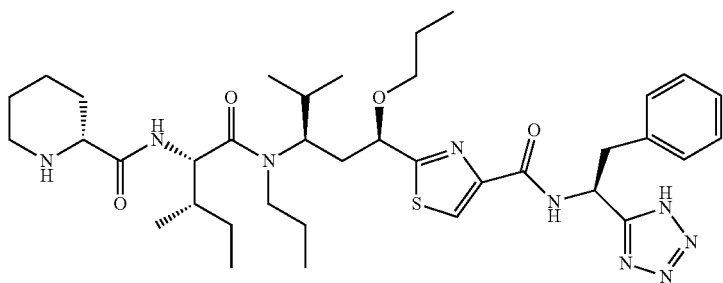
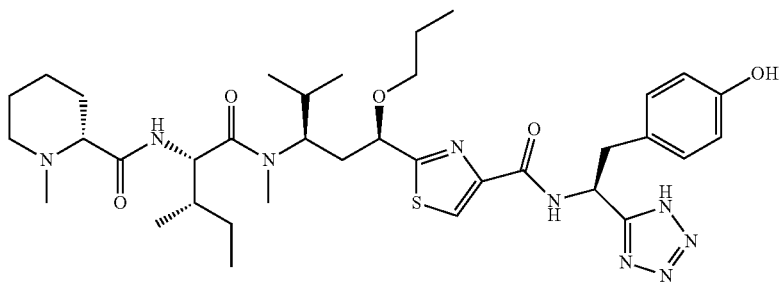
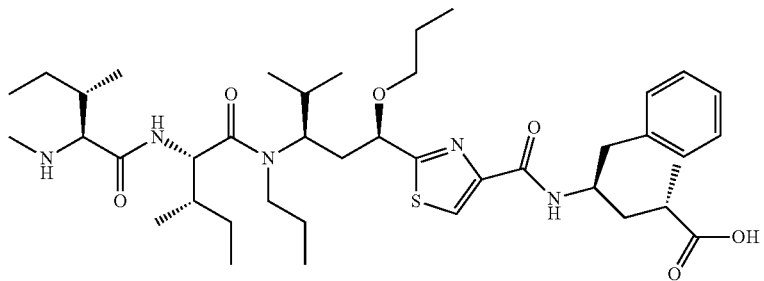
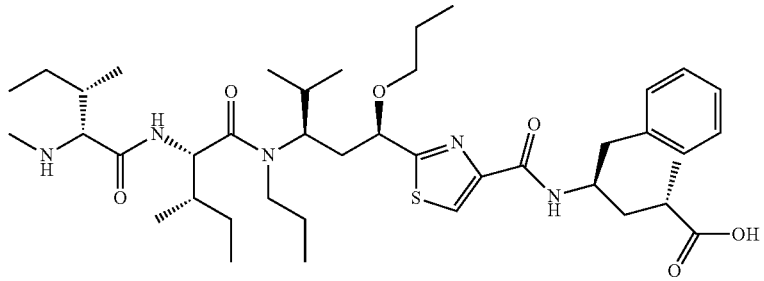
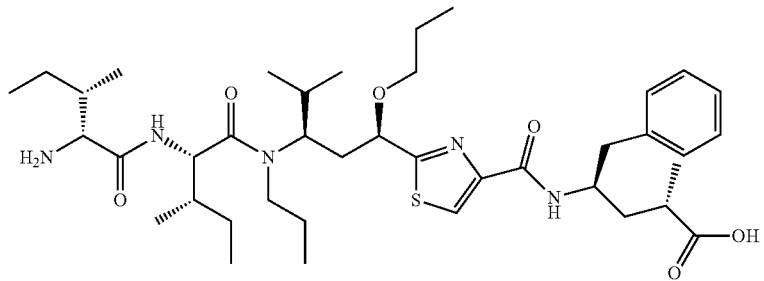
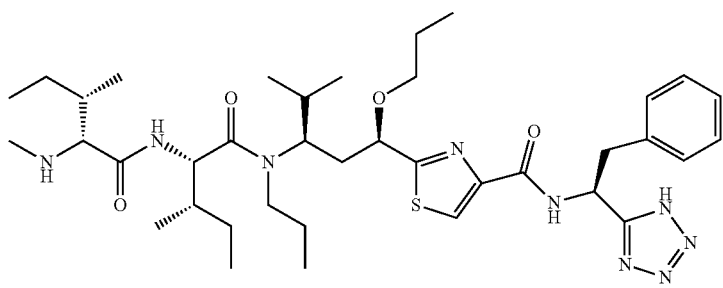

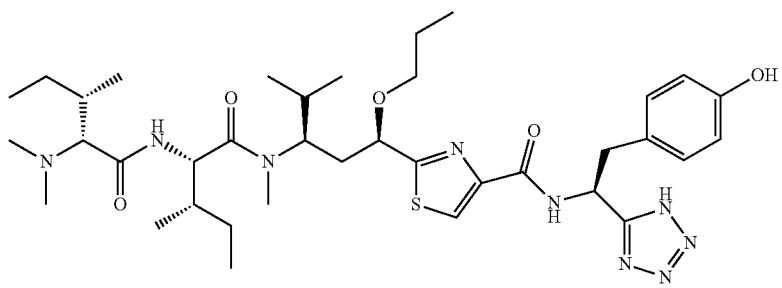
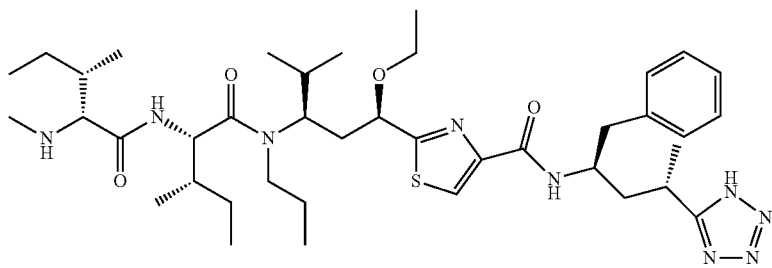
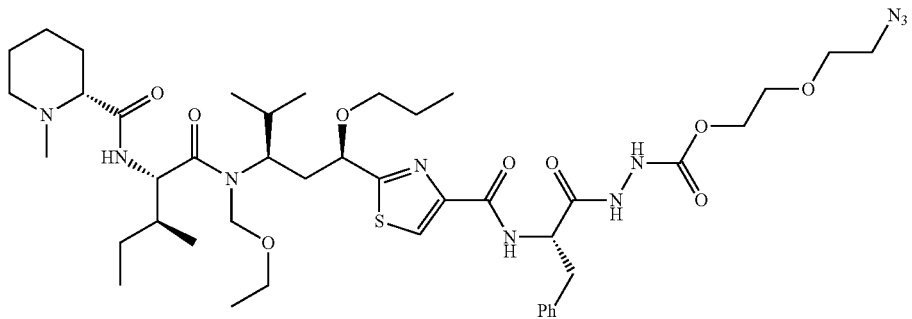
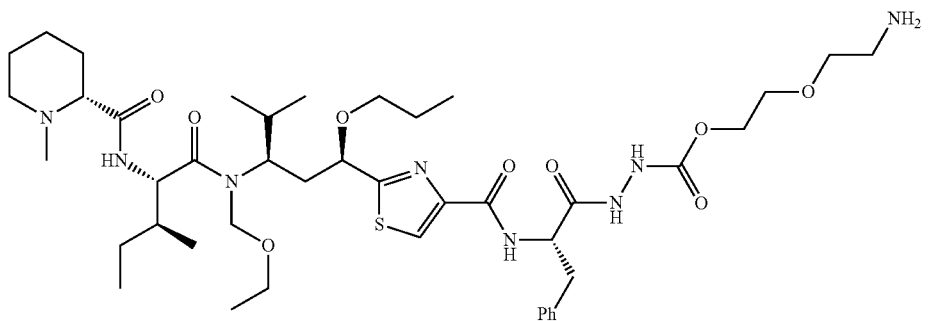
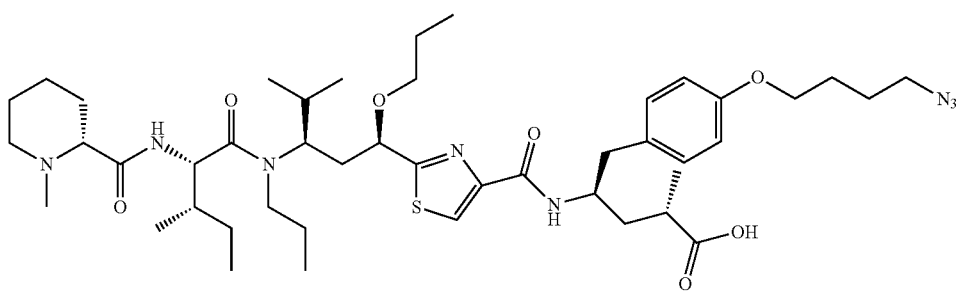

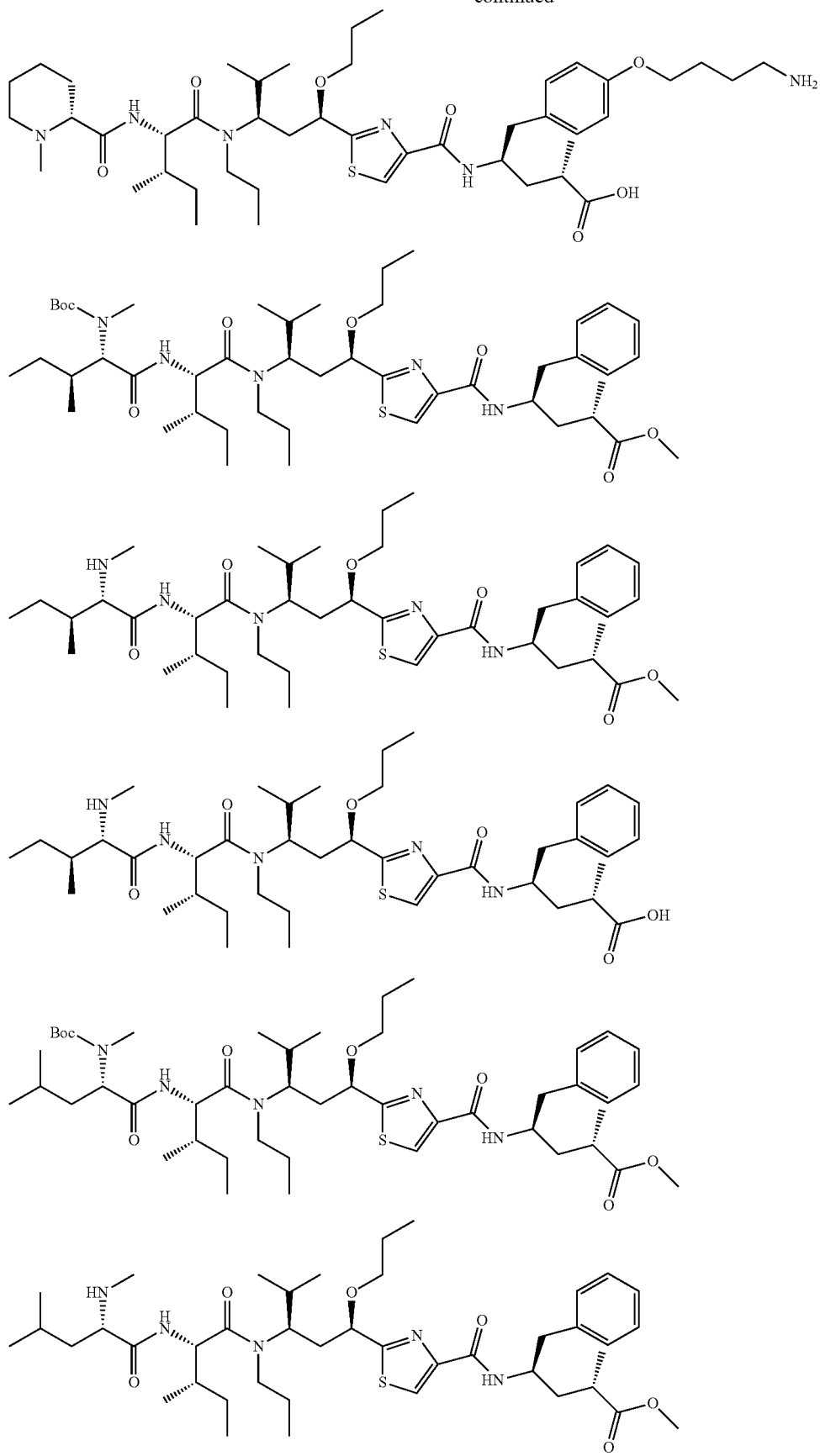

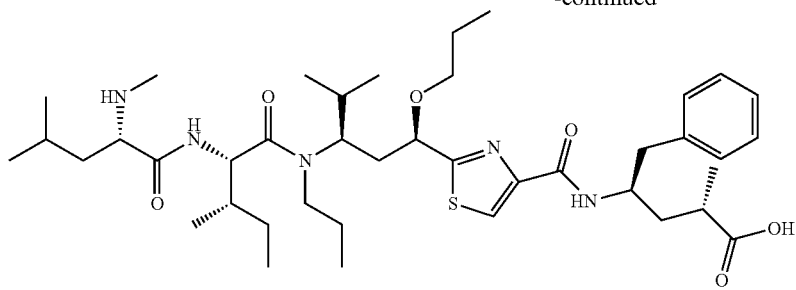
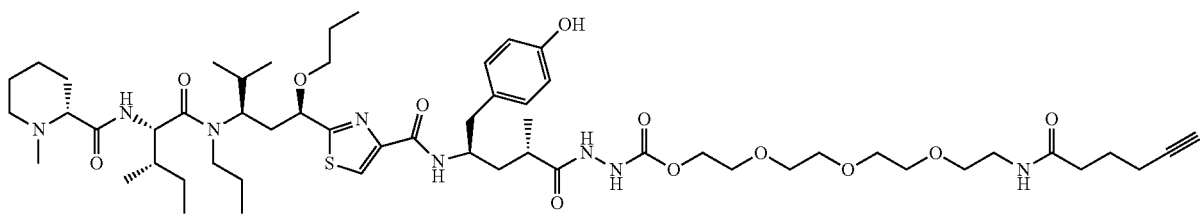
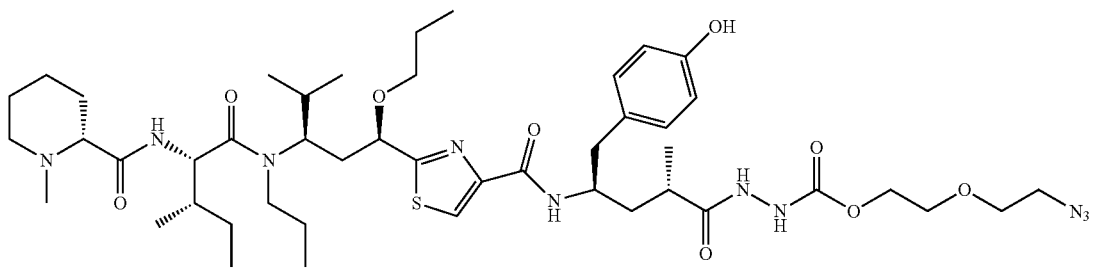
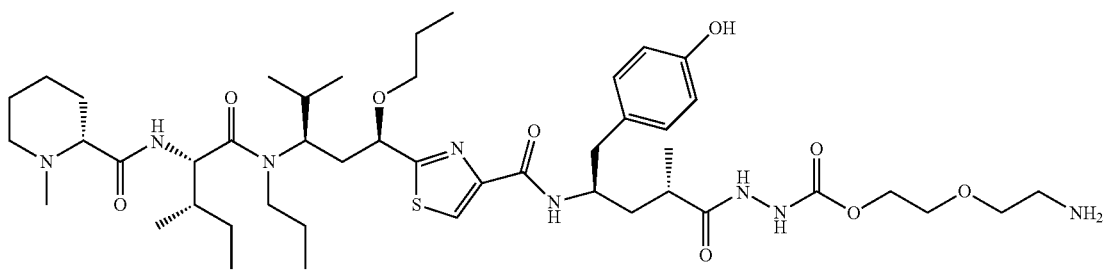
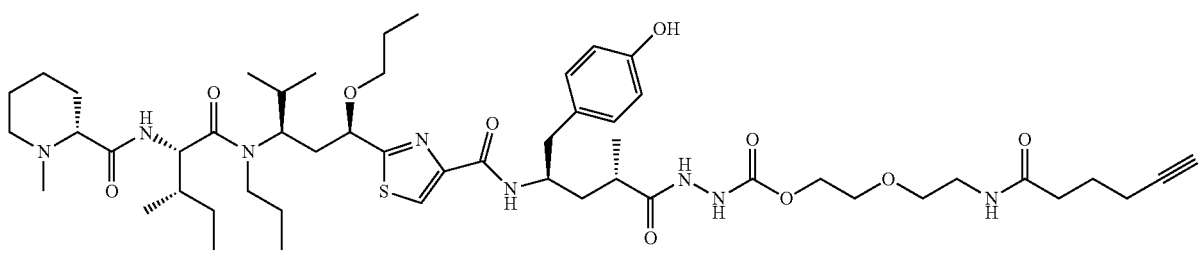
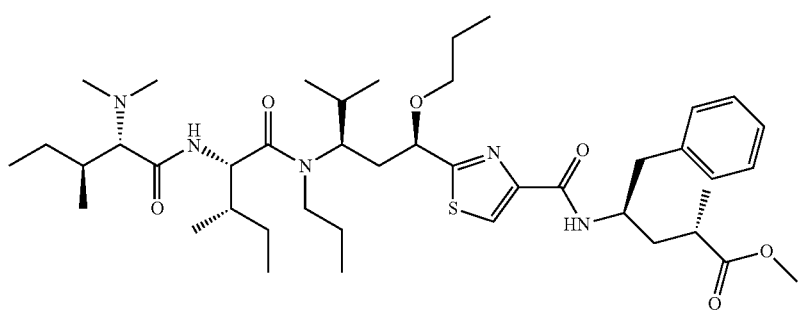

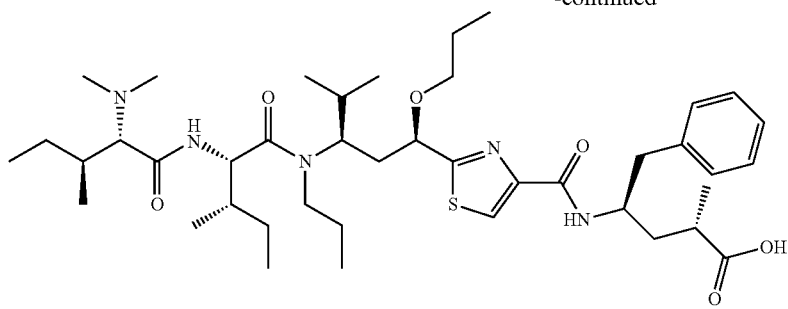
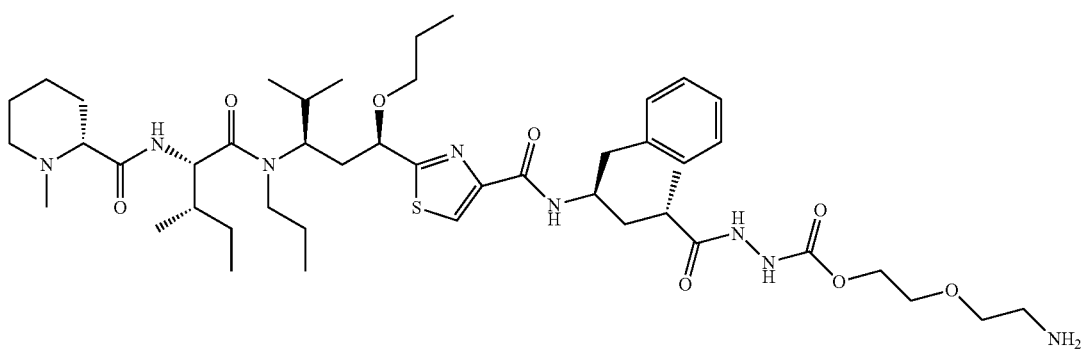
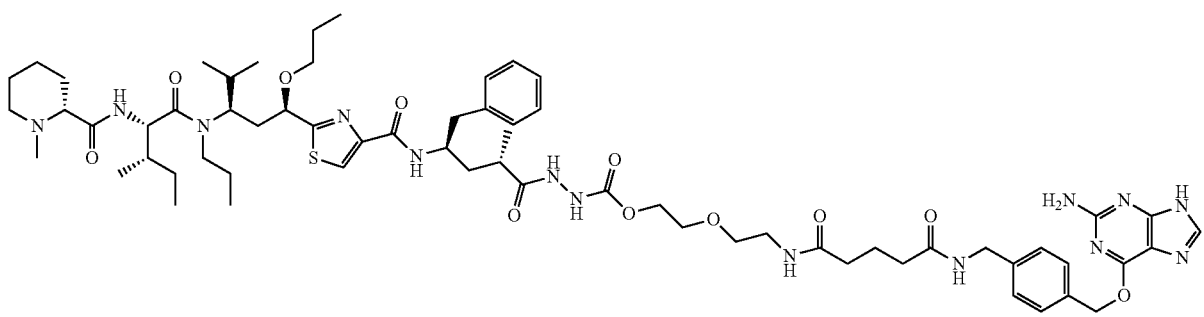
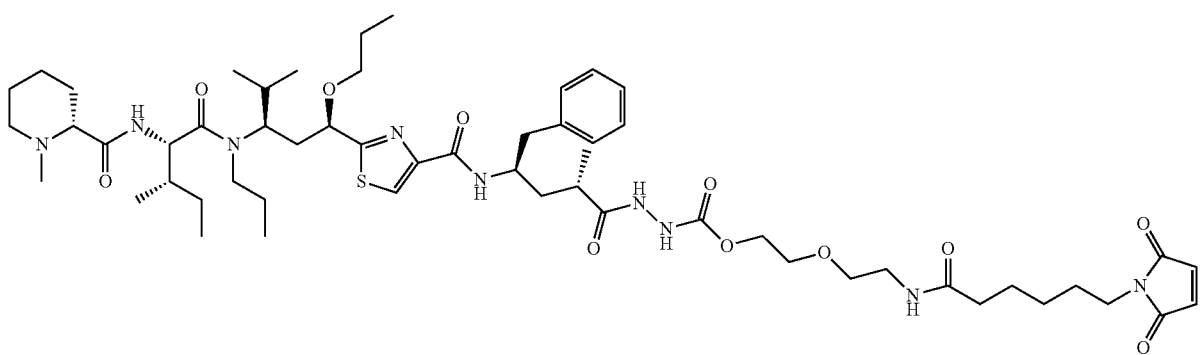
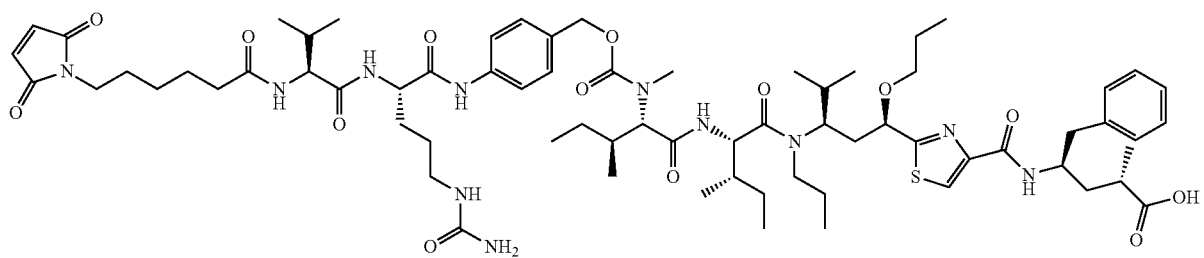

-continued
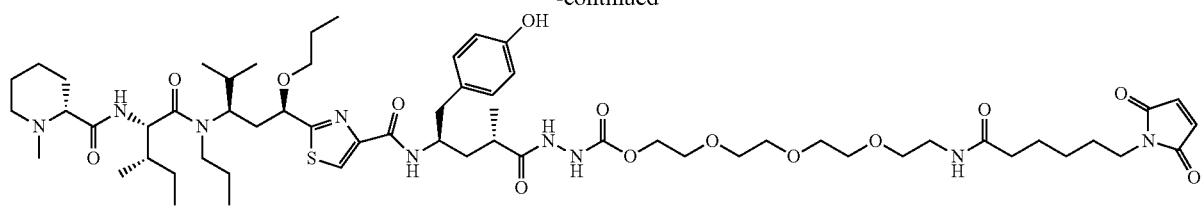
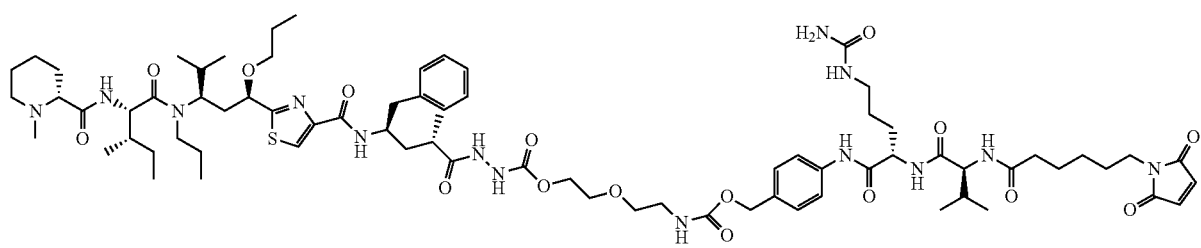
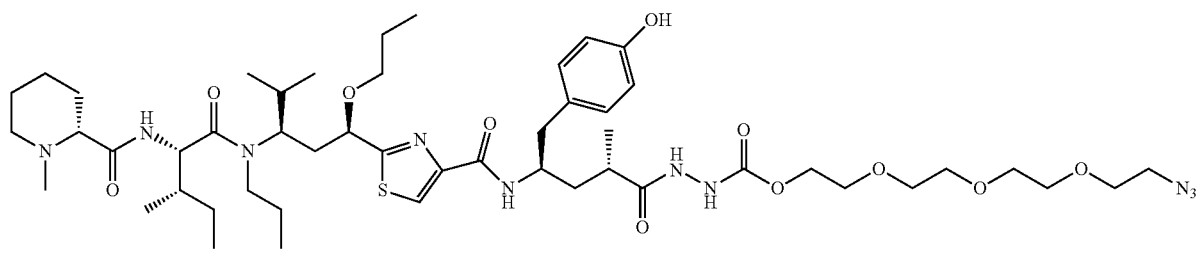
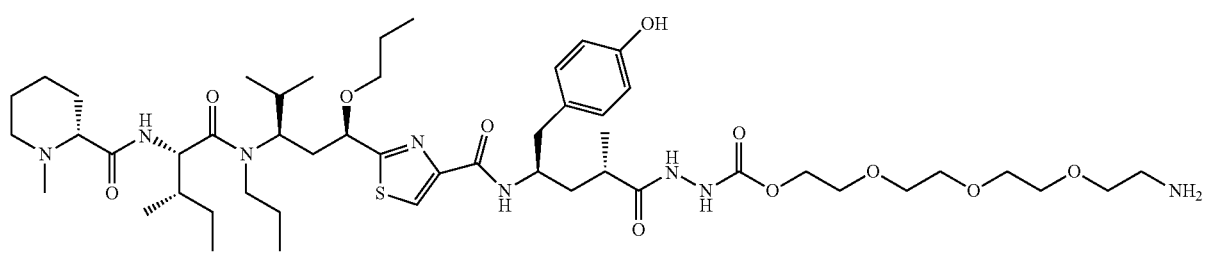
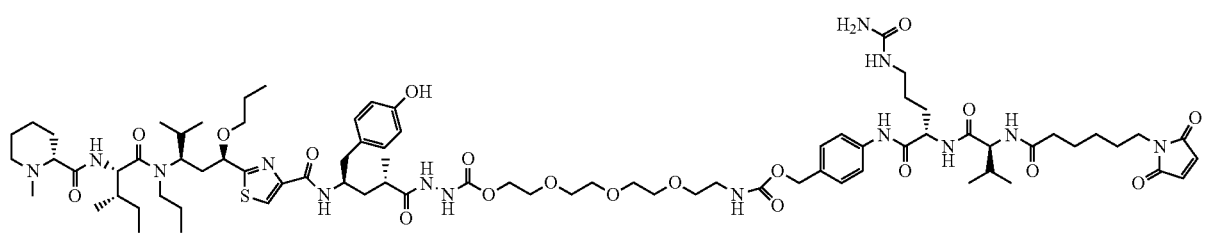
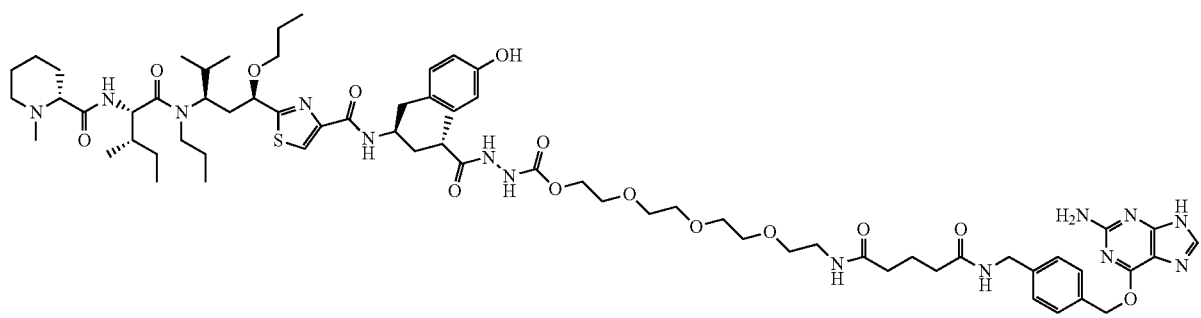

-continued
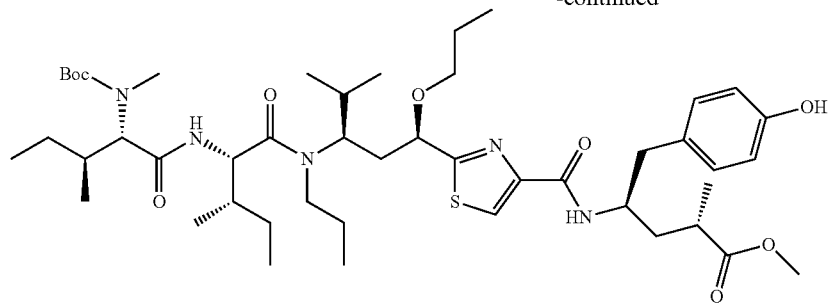
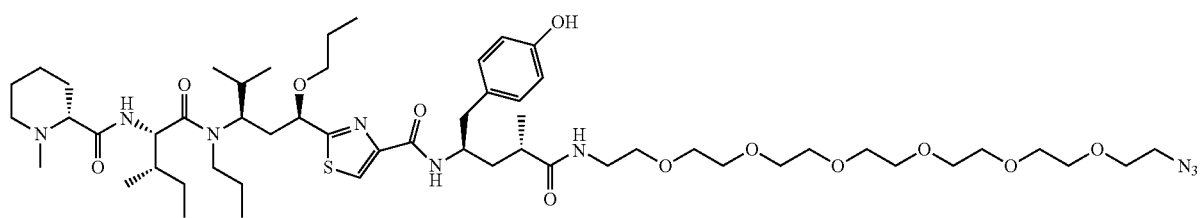
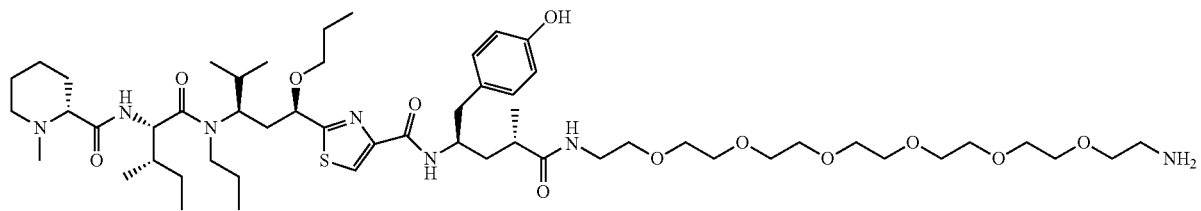
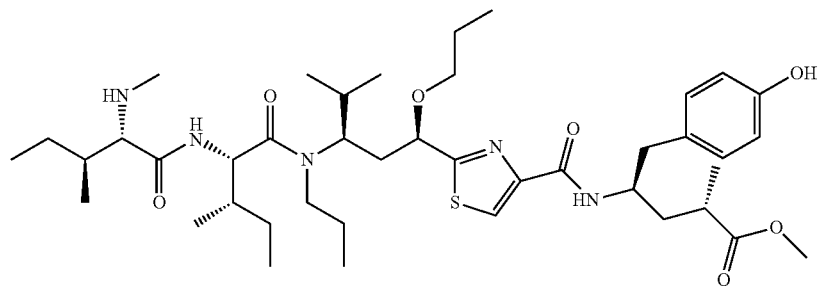
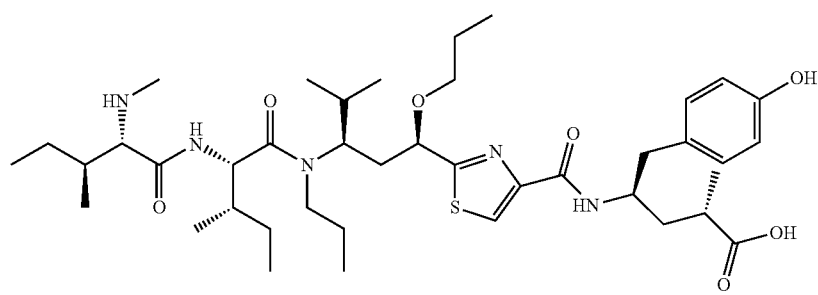
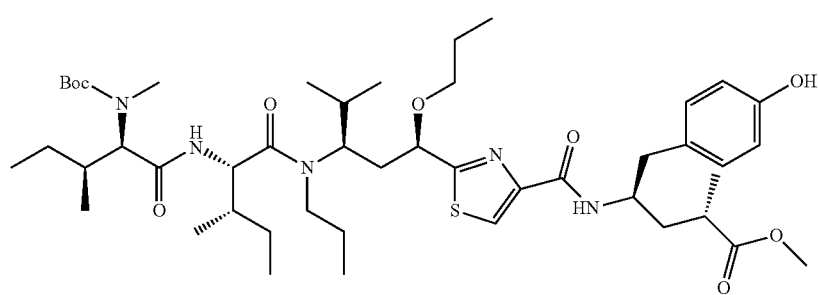

-continued
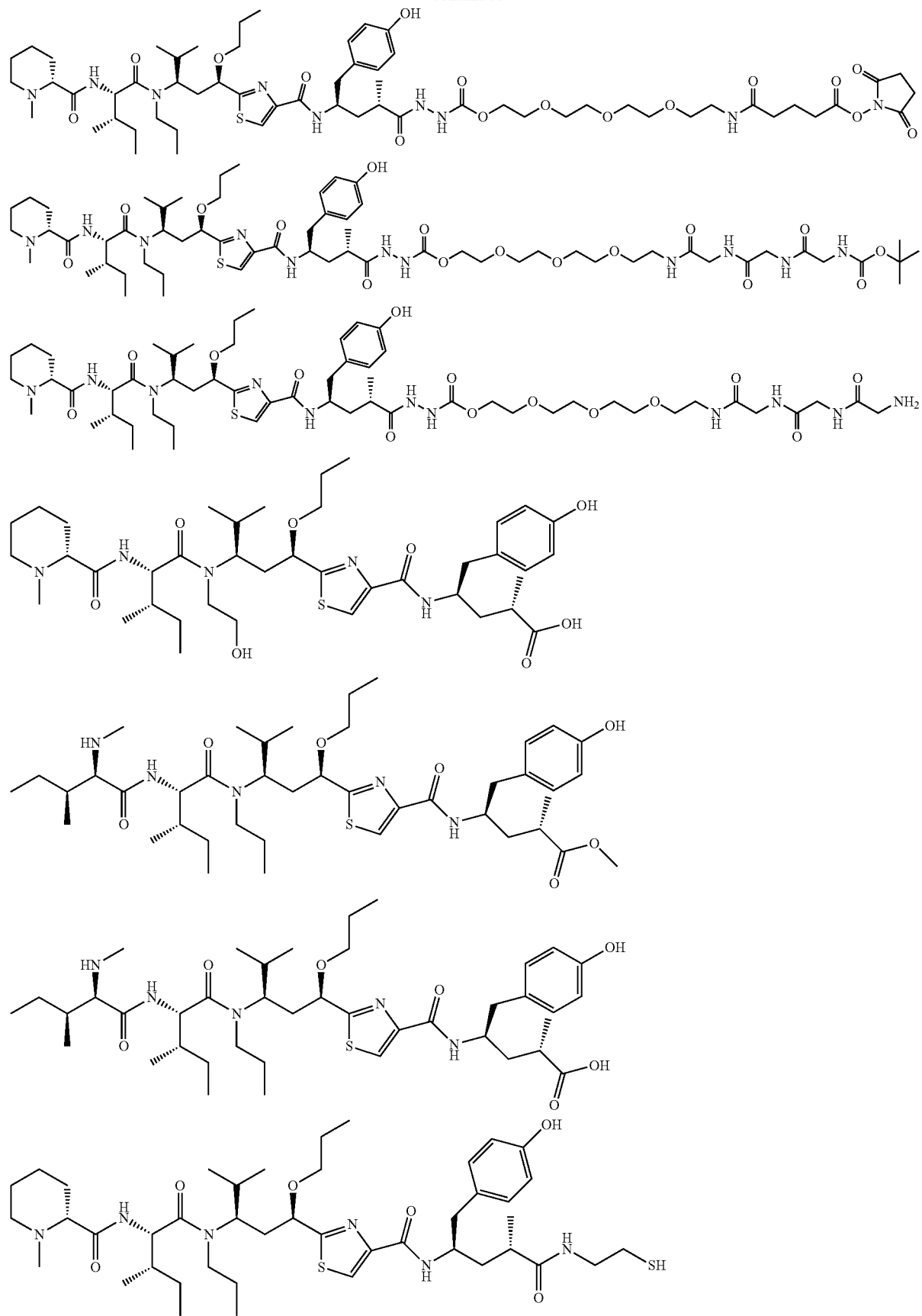

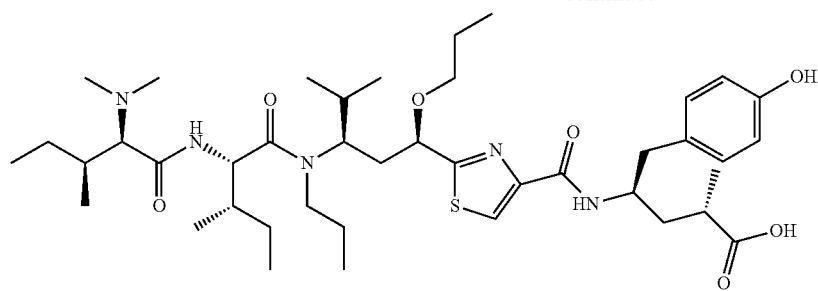
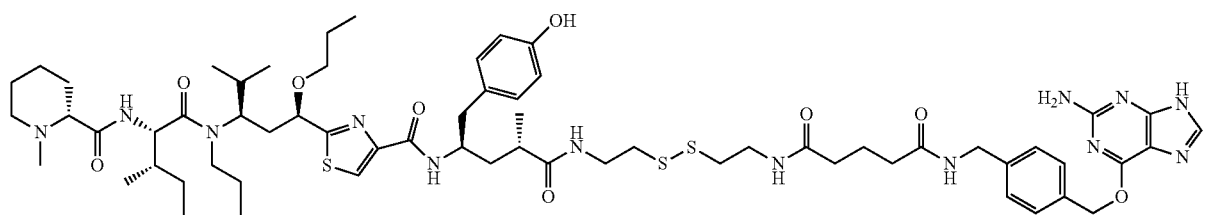
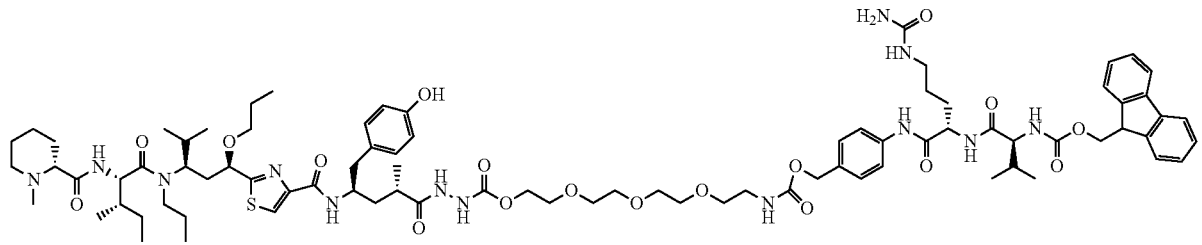
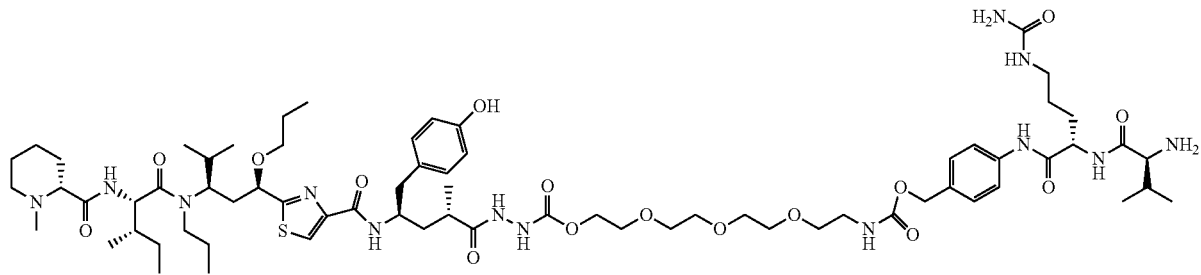
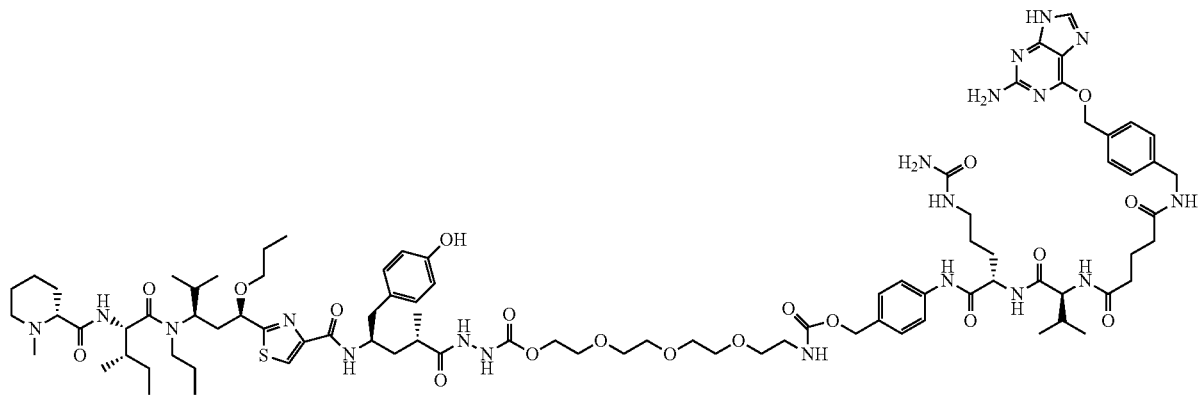

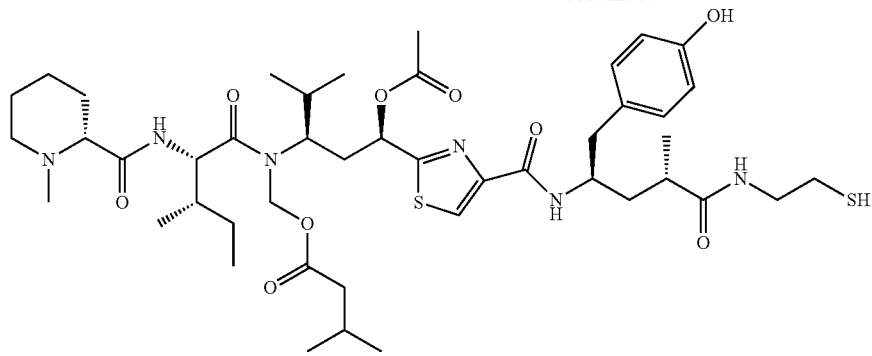
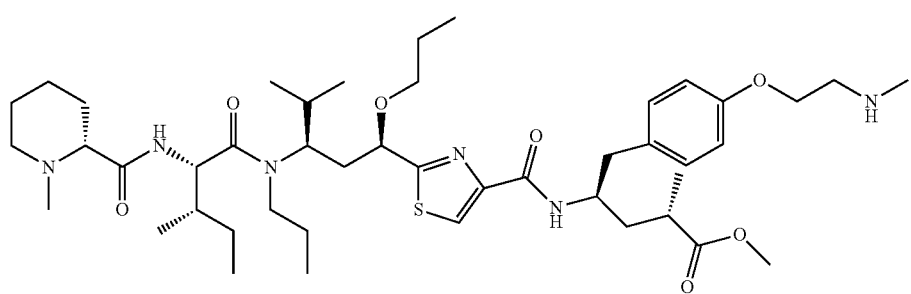
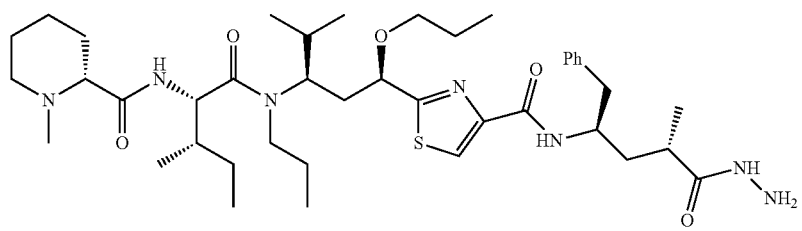
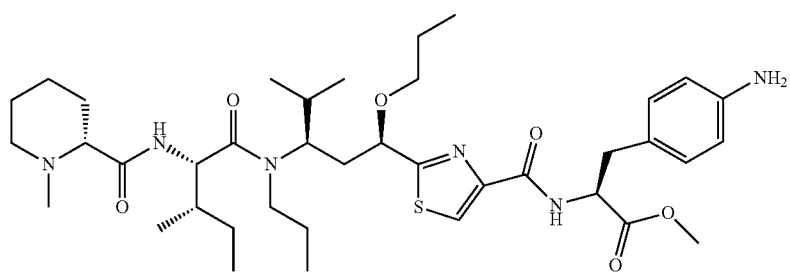
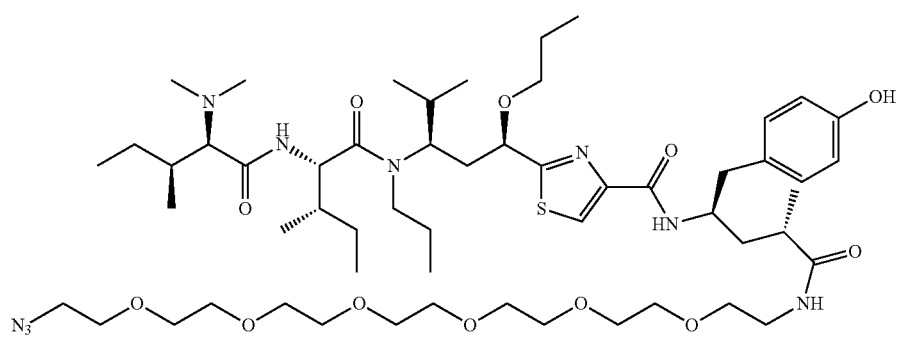

-continued
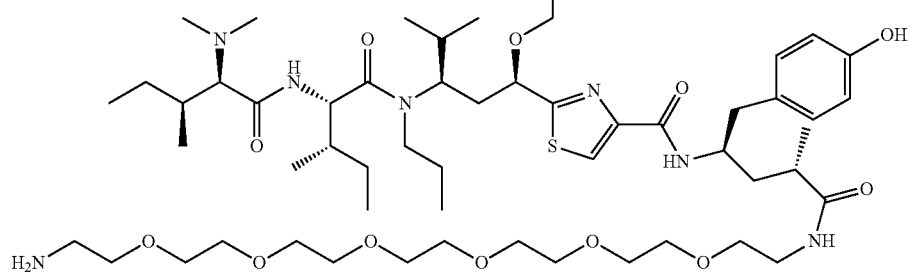
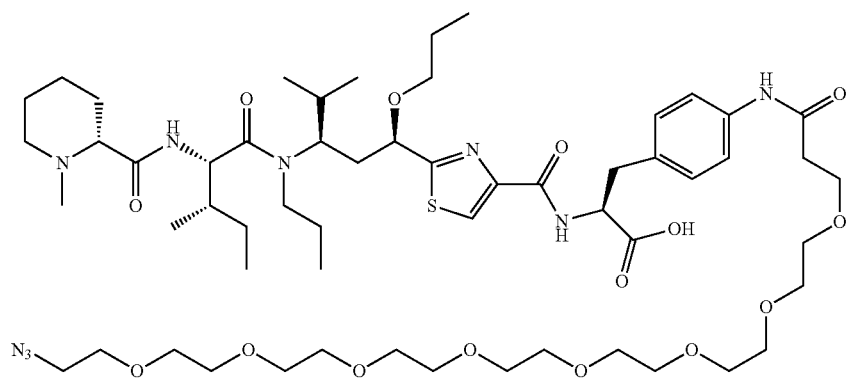
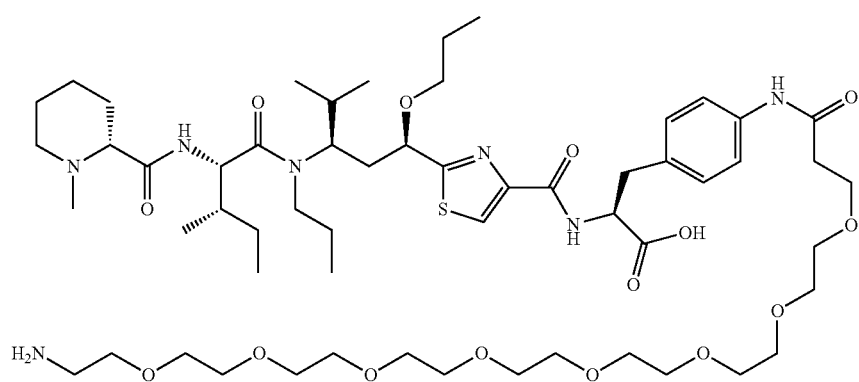
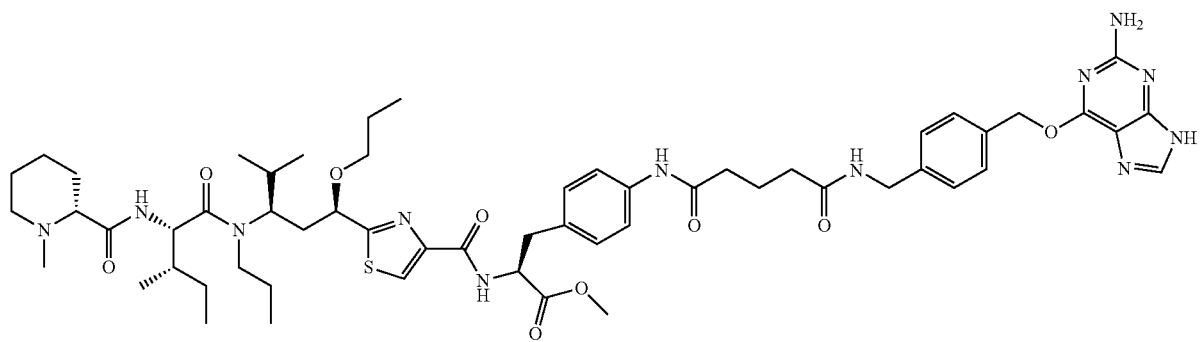

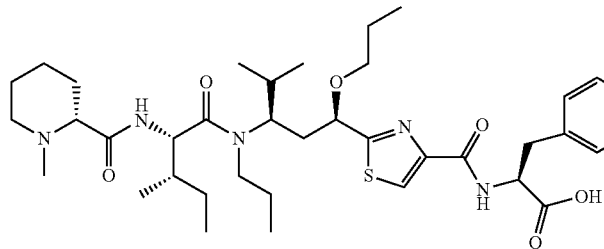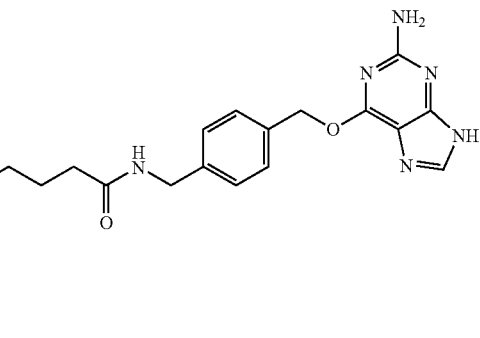
Preferably, the compounds disclosed in International Patent Application PCT/EP2013/002790 are excluded from the present application or patent.
Especially preferably, the following compounds are excluded from the present application or patent:
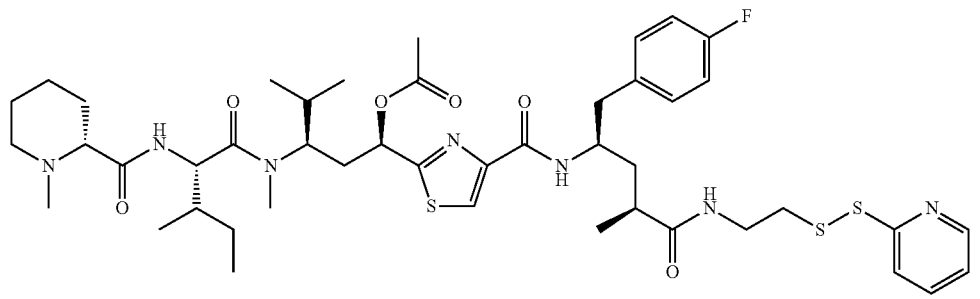
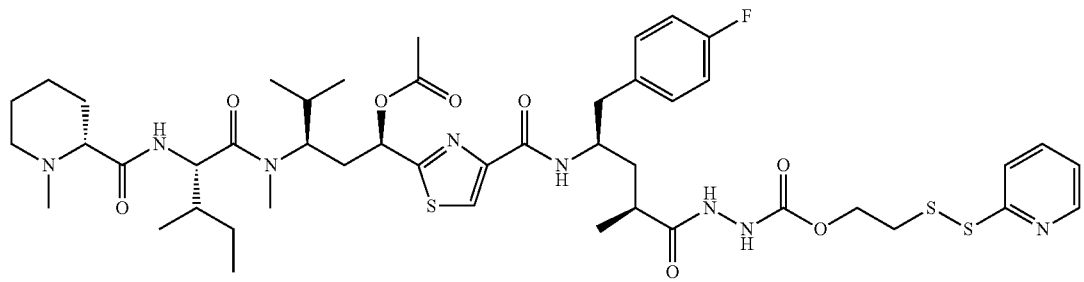
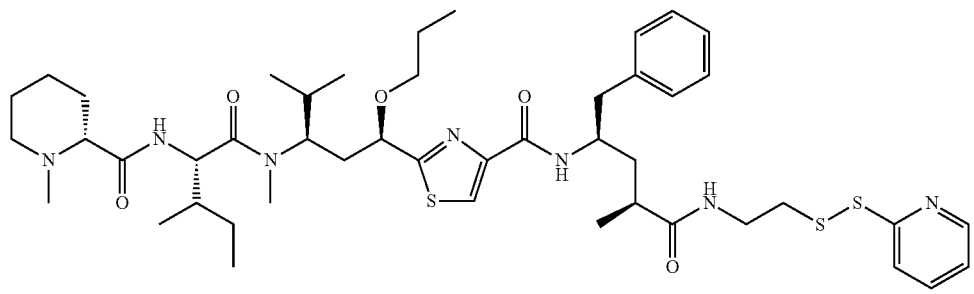
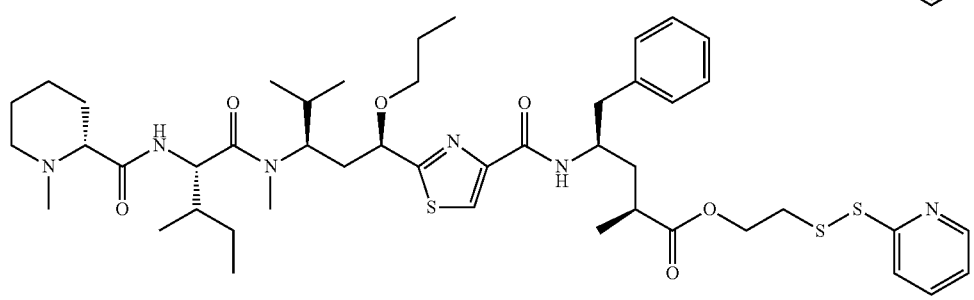

-continued

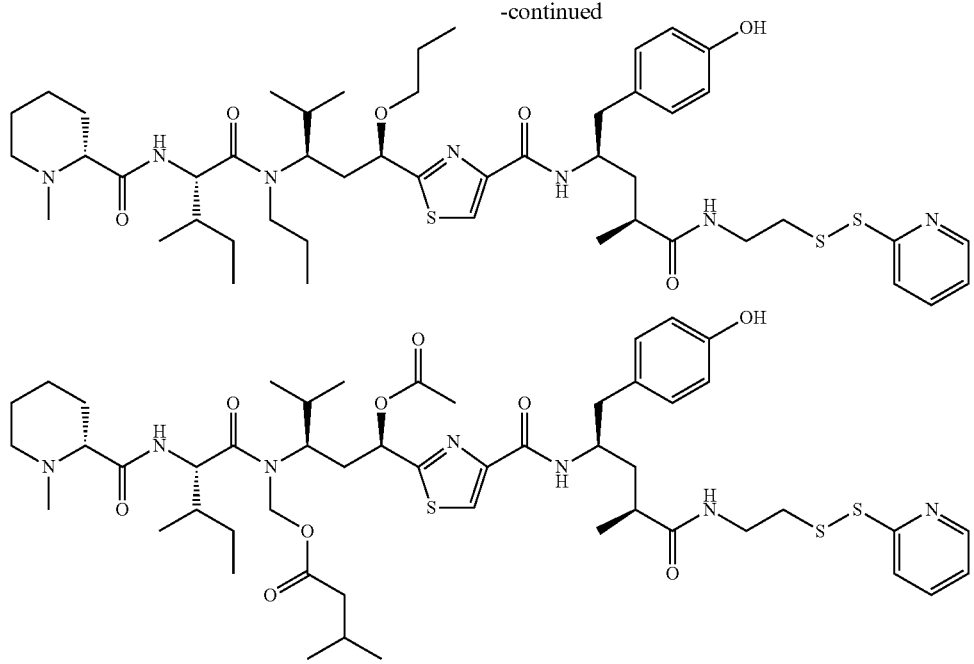

The use of compounds of formula (I), (II), (III) and (IV) for the preparation of medicaments (e.g. by conjugation) for the treatment and/or prevention of cancer or other diseases is also subject of the present invention. Moreover, the present compounds are of interest for the prevention and/or treatment of tumor diseases.

Cancers that can be treated or prevented by the compounds and the corresponding conjugates of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumour, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukaemia and acute myelocytic leukaemia (myeloblastic, promyelocytic, myelomonocytic, monocytic and erythroleukemia); chronic leukaemia (chronic myelocytic (granulocytic) leukaemia and chronic lymphocytic Leukaemia), and polycythemia vera, lymphoma (Hodgkin's disease and non-Hodgkin's disease), multiple myeloma. Waldenstrohm's macroglobulinemia, and heavy chain disease.

Other examples of leukaemias include acute and/or chronic leukaemias, e.g., lymphocytic leukaemia (e.g., as exemplified by the p388 (murine) cell line), large granular lymphocytic leukaemia, and lymphoblastic leukaemia; T-cell leukaemias, e.g., T-cell leukaemia (e.g., as exemplified by the CEM, Jurkat, and HSB-2 (acute), YAC 1 (murine) cell lines), T-lymphocytic leukaemia, and T-lymphoblastic leukaemia; B cell leukaemia (e.g., as exemplified by the SB (acute) cellline), and B-lymphocytic leukaemia; mixed cellieukaemias, e.g., B and T cellieukaemia and B and T lymphocytic leukaemia: myeloid leukaemias, e.g., granulocytic leukaemia, myelocytic leukaemia (e.g., as exemplified by the HL-60 (promyelocyte) cell line), and myelogenous leukaemia (e.g., as exemplified by the K562 (chronic) cellline); neutrophilic leukaemia; eosinophilic leukaemia: monocytic leukaemia (e.g., as exemplified by the THP-1 (acute) cellline); myclomonocytic Leukaemia; Naegeli-type myeloid leukaemia; and nonlymphocytic leukemia. Other examples of leukaemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B.C. Decker Inc. (2000). The entire teachings of the preceding references are incorporated herein by reference.

EXAMPLES

The syntheses of the respective building blocks used for the preparation of the respective compounds of formula (I), (II), (III) and (IV) (Tubulysin and/or Cytolysin Derivatives) were performed e.g. according to procedures described in PCT/EP2008/003762 (WO 2008/138561). The term Cytolysins as used herein refers to synthetic derivatives of Tubulysins.

All compounds described herein were characterized by $^1$H-NMR, $^{13}$C-NMR and mass spectroscopy. The purity was identified by HPLC.

General Procedure for the Synthesis of Tubulysin/Cytolysin Derivatives with Disulfide Spacers:

Synthesis of Tubulysin/Cytolysin-S—S-Py:

Tubulysin/Cytolysin or corresponding building block: 0.1 mmol

DMF: 7.0 mL

HBTU: 0.12 mmol

DIEA: 0.4 mmol

Spacer-HCl: 0.16 mmol

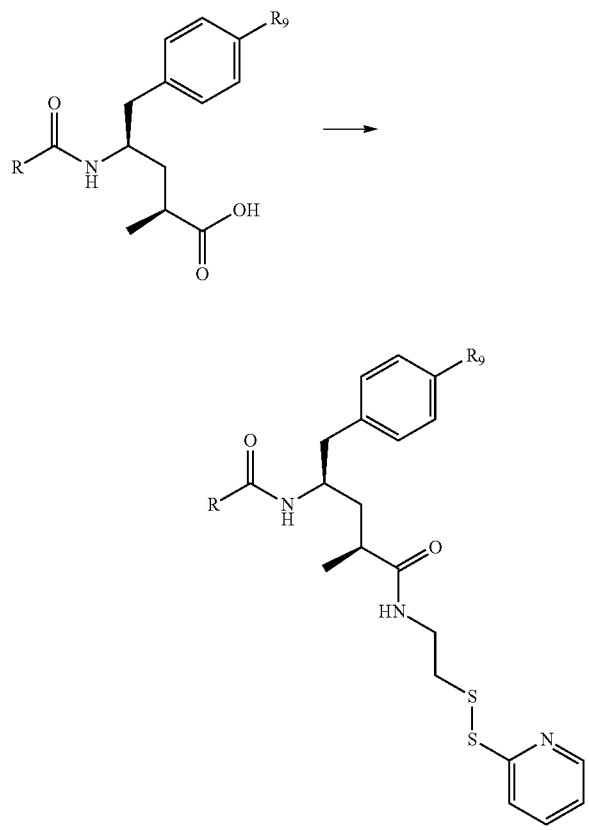

Therein, R is either a suitable protecting group known in the state of the art or the corresponding part of a tubulysin or cytolysin derivative shown in the examples but not limited to these.

To a stirred solution of a Tubulysin/Cytolysin or the corresponding building block and Spacer were added HBTU and diisopropylethylamine (DIEA) at 0° C. After complete addition the cooling bath was removed and the reaction mixture was monitored by TLC or HPLC. After ca. 2-4 h the completion of reaction was indicated, then the mixture was loaded directly to a column and first eluted with pure DCM (ca. 700 mL) and then with a gradient of 1-3% Methanol: DCM to obtain the pure compound in ca. 65-85% yield.

General Procedure for the Synthesis of Tubulysin/Cytolysin Derivatives with Hydrazide Spacers:

Synthesis of Tubulysin/Cytolysin-NHNHCO—(O—CH$_2$—CH$_2$—O—)$_n$—N$_3$ (Hydazide-Spacer):

TAM424: 92 mg (0.119 mmol)

$^t$butyl chloroformate: 16 μL (0.12 mmol, 1.01 eq.)

EtOAc: 2 mL

DIPEA: 70 μL

Linker (e.g. TAM422B): 50 mg (0.16 mmol)

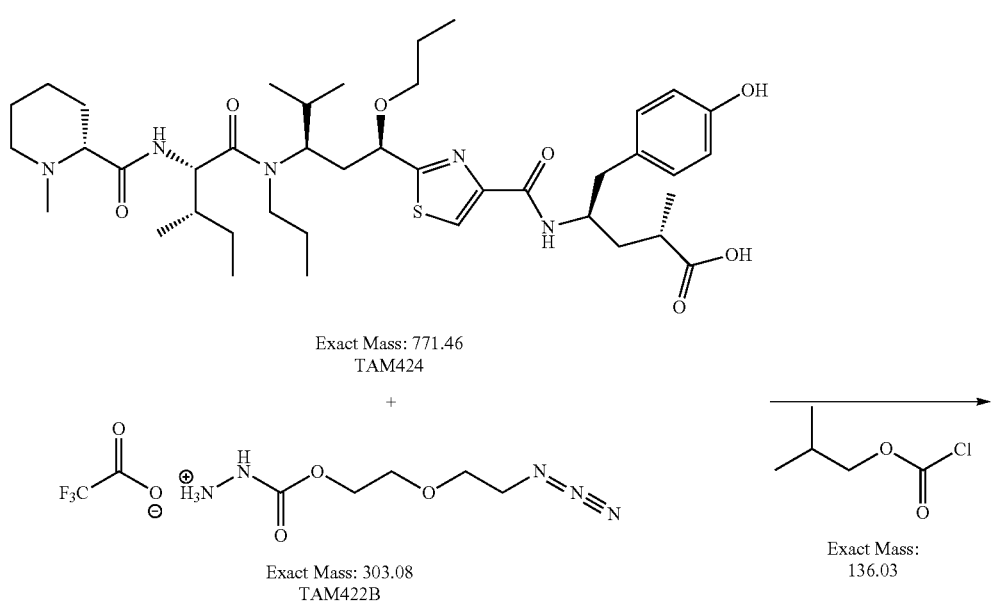

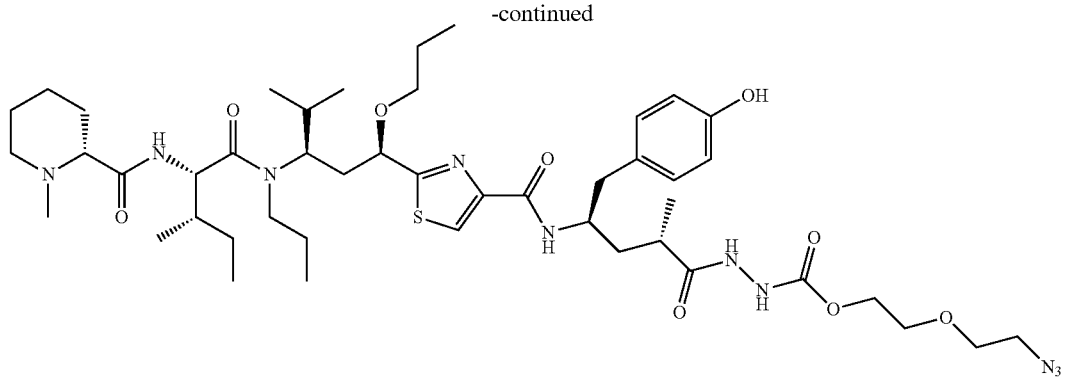

Exact Maa: 942.54
TAM426

DIPEA and isobutyl chloroformate were added together with a syringe into a solution of TAM424 in anhydrous EtOAc at −15° C. After stirring for 45 minutes at −15° C. under argon a solution of TAM422B in anhydrous EtOAc (1.0 mL) was added to the reaction mixture. The resulting solution was stirred under argon at −15° C. for 15 minutes and at room temperature for an additional 45 minutes and then concentrated. The residue was purified by flash chromatography (silica gel, 1-3% MeOH in DCM) to give TAM426 (59.5 mg, >95% purity according to HPLC) in 53% isolated yield.

General Procedure for the Synthesis of Tubulysin/Cytolysin Derivatives with Alkyl Azide Spacer:

Synthesis of Tubulysin/Cytolysin-$(CH_2)_n$—$N_3$:
Tubulysin/Cytolysin: 0.1 mmol
DMF: 5 mL
$K_2CO_3$: 60 mg
Spacer: 0.2 mmol

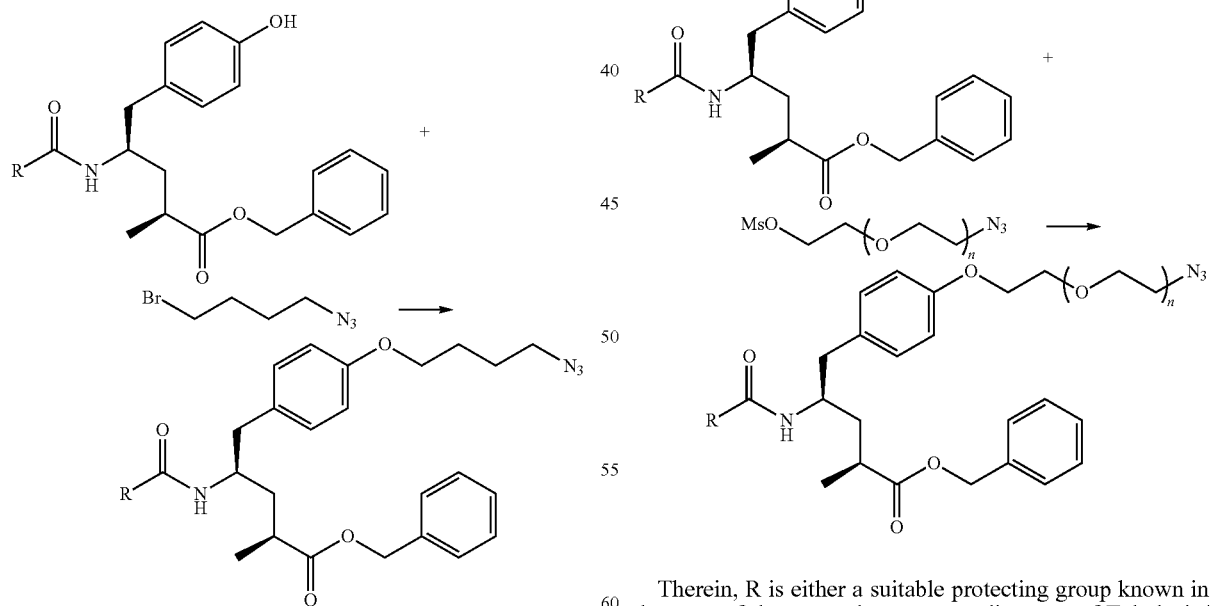

Therein, R is either a suitable protecting group known in the state of the art or the corresponding part of Tubulysin/Cytolysin derivative shown in the examples but not limited to these.

To a stirred solution of Tubulysin/Cytolysin and $K_2CO_3$ was added the corresponding alkyl azide spacer at RT. The reaction mixture was stirred overnight and monitored with TLC or HPLC. After completion of the reaction the solution was concentrated, redissolved in DCM and extracted with saturated ammonium chloride. The aqueous phase was extracted with DCM, the organic fractions were combined and dried over sodium sulphate. After evaporation of the solvent the crude product was purified by column chromatography (1-5%, Methanol:DCM).

General Procedure for the Synthesis of Tubulysin/Cytolysin Derivatives with Ethylenoxy Spacers:

Synthesis of Tubulysin/Cytolysin-$(CH_2$—$CH_2$—$O$—$)_n$-$N_3$:
Tubulysin/Cytolysin: 0.1 mmol
Acetonitrile: 20 mL
$K_2CO_3$: 60 mg
Spacer: 0.2 mmol Therein, R is either a suitable protecting group known in the state of the art or the corresponding part of Tubulysin/Cytolysin derivative shown in the examples but not limited to these.

To a stirred solution of a Tubulysin/Cytolysin or the corresponding building block and $K_2CO_3$ the mesylated (oligo)-ethyleneoxy azide spacer was added at RT and then heated to 60° C. for 18 h. The reaction was monitored with TLC or HPLC. After completion of the reaction the mixture was filtered and concentrated. The residue was redissolved in DCM and extracted with saturated ammonium chloride. The aqueous phase was extracted with DCM, the organic fractions were combined, washed with saturated brine and dried over sodium sulphate. After removing the solvent the product was purified by column chromatography (usually 1-5%; Methanol:DCM).

General Procedure for the Synthesis of Tubulysin/Cytolysin Derivatives with Glycine Spacers:

Synthesis of Tubulysin/Cytolysin-(Glycin)$_n$-NH$_2$:

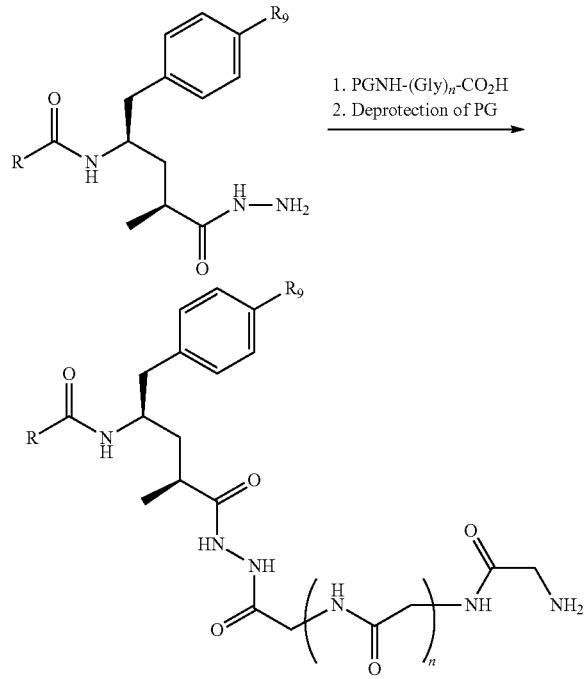

Therein, R is either a suitable protecting group (PG) known in the state of the art or the corresponding part of Tubulysin/Cytolysin derivative shown in the examples but not limited to these.

The number of glycine derivatives is three to ten. The corresponding glycine moieties are used with the appropriate protection groups known in the state of the art; e.g. the amino function is protected before coupling as a FMOC or BOC derivative and the carboxylic terminus is protected as an ester which is able to be removed under commonly known conditions. The carboxylic acid protection is removed before the coupling to the Tubulysin/Cytolysin or the appropriate building block by using the commonly known deprotection conditions.

TAM470: 78.5 mg (0.10 mmol)
$^i$butyl chloroformate: 15 µL (0.11 mmol, 1.01 eq.)
EtOAc: 2.0 mL
DIPEA: 70 µL
Boc-triglycine carboxylic acid: 32 mg (0.11 mmol)

DIPEA and isobutyl chloroformate were added together with a syringe to a solution of N-Boc-triglycine in anhydrous EtOAc at −15° C. After stirring for 45 minutes at −15° C. under argon a solution of TAM470 in anhydrous EtOAc (1.0 mL) was added to the reaction mixture. The resulting solution was stirred under argon at −15° C. for 15 minutes and at room temperature for an additional 45 minutes and then concentrated. The residue was purified by flash chromatography (silica gel, 1-3% MeOH in DCM) to give the BOC protected hydrazine derivative in 76% isolated yield.

The BOC group was removed by dissolving the product obtained above in THF (1 ml) and addition of hydrochloride in THF at 0° C. The reaction mixture was stirred for 30 min at room temperature. The reaction mixture was diluted with dichloromethane and washed with saturated ammonium chloride, dried and concentrated to yield 82 mg of the free amine TAM479 (yield 86%).

| Name | Structure | Mass [e/z] | IC50 [nM] |
|---|---|---|---|
| TAM008 | 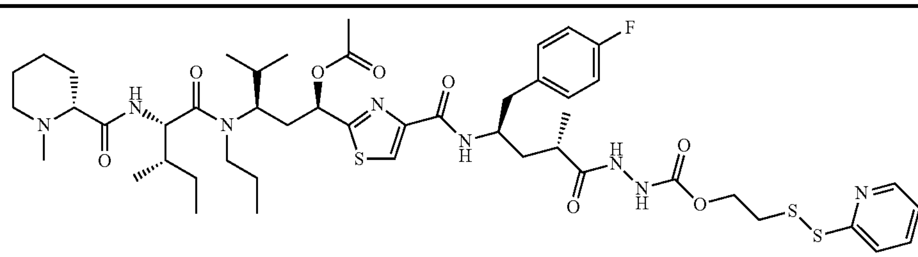 | 1000.4 | |
| TAM024 | 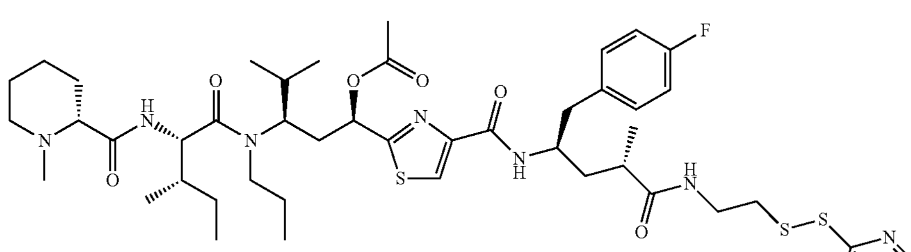 | 941.4 | |

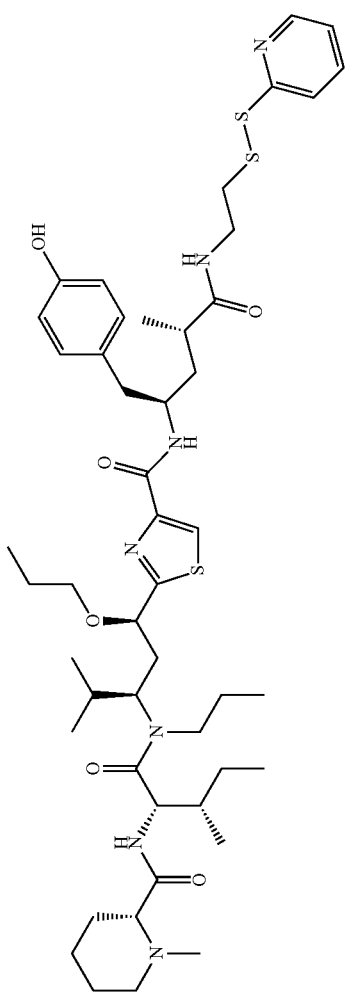
TAM274  940.3
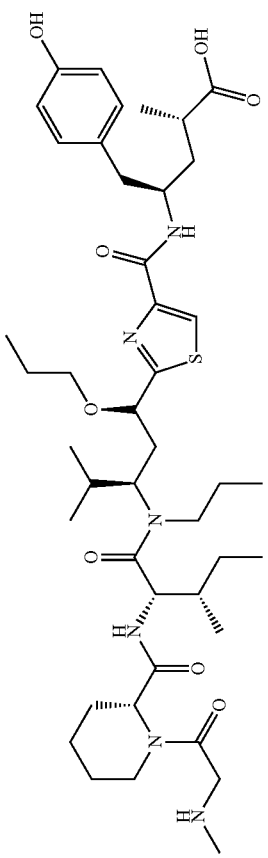
TAM320  829.1
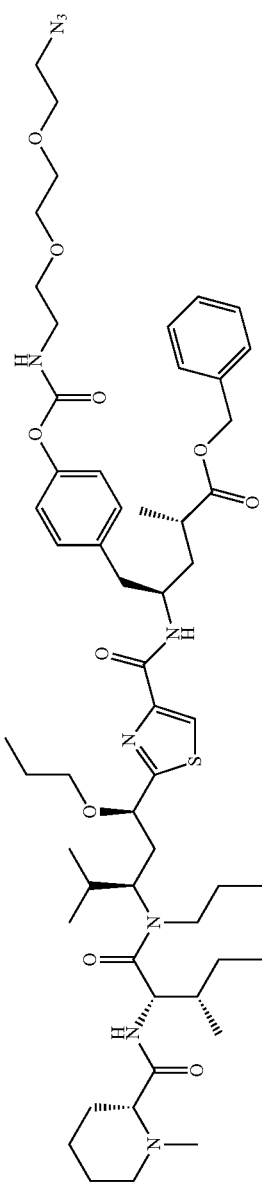
TAM370  1061.6

-continued
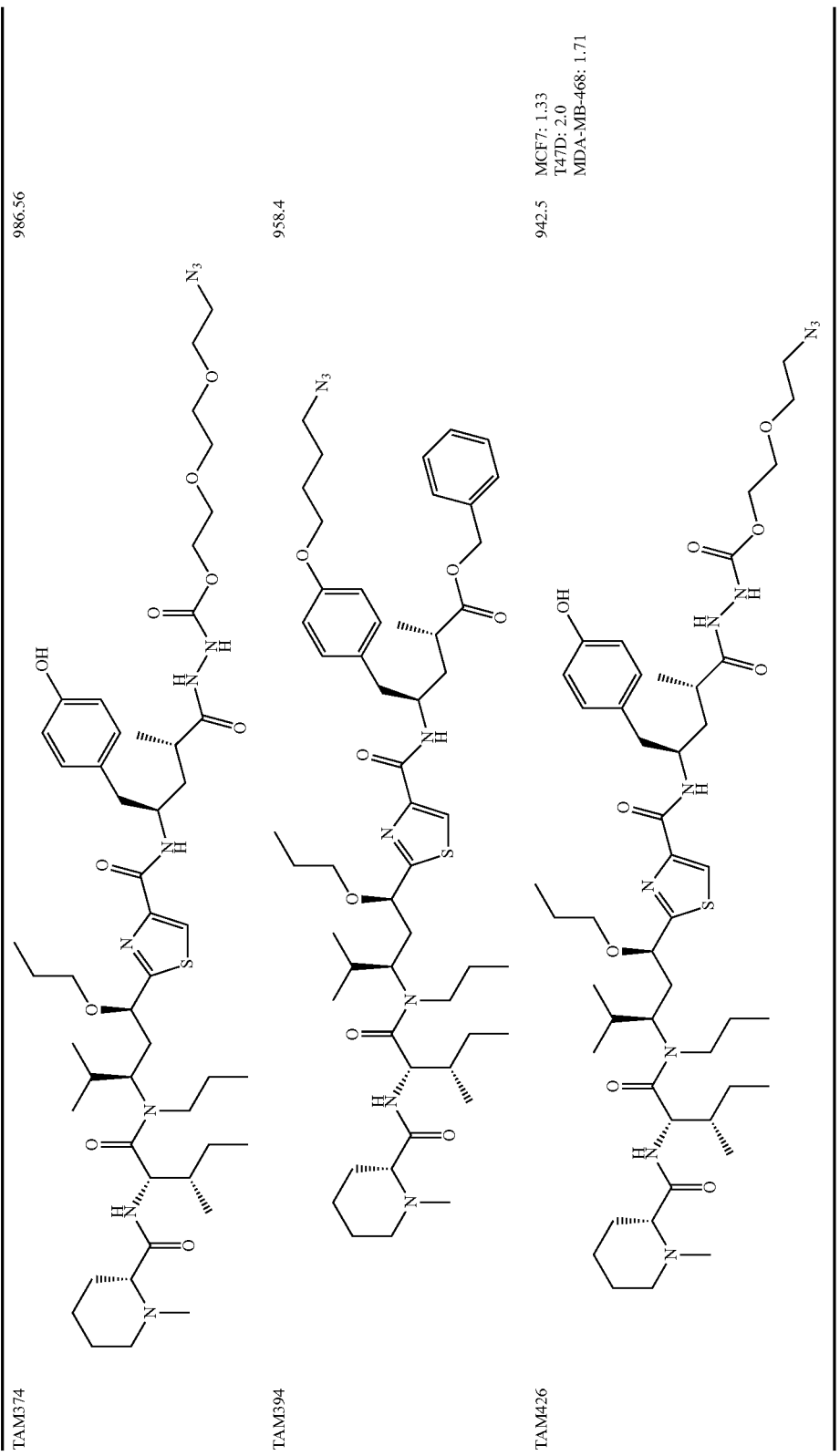

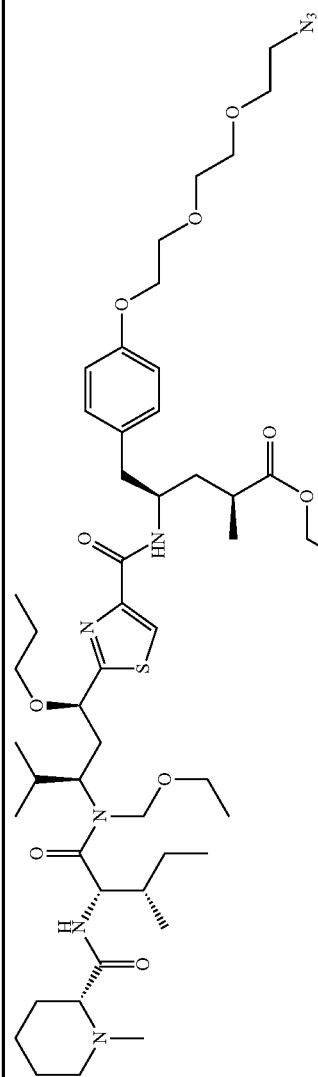
TPM263    1034.5
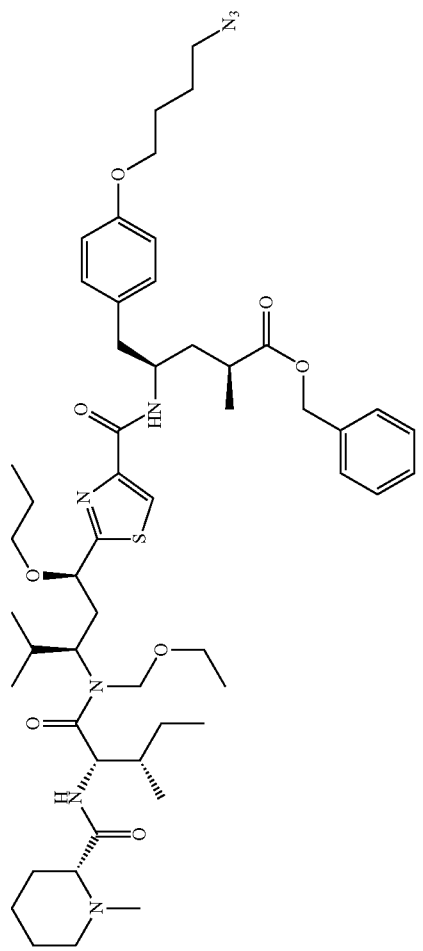
TPM262    974.5

| | | |
|---|---|---|
| TAM334 | 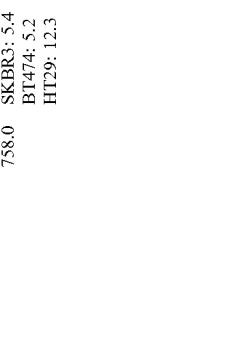 | 758.0 SKBR3: 5.4<br>BT474: 5.2<br>HT29: 12.3 |
| TAM365 | 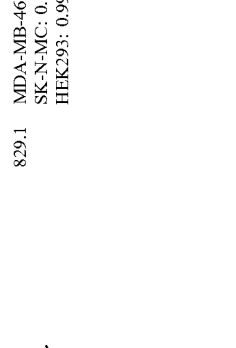 | 829.1 MDA-MB-468: 3.41<br>SK-N-MC: 0.92<br>HEK293: 0.99 |
| TAM371 | 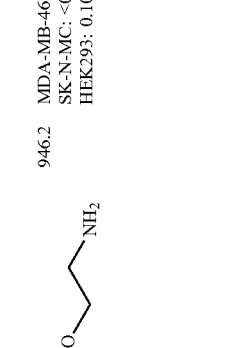 | 946.2 MDA-MB-468: 0.13<br>SK-N-MC: <0.01<br>HEK293: 0.10 |
| TAM375 | 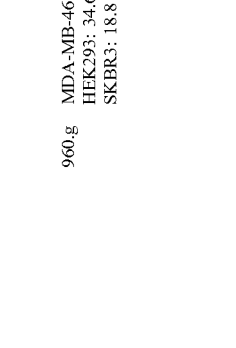 | 960.g MDA-MB-468: 25.8<br>HEK293: 34.6<br>SKBR3: 18.8 |

| | | | |
|---|---|---|---|
| TAM405 | 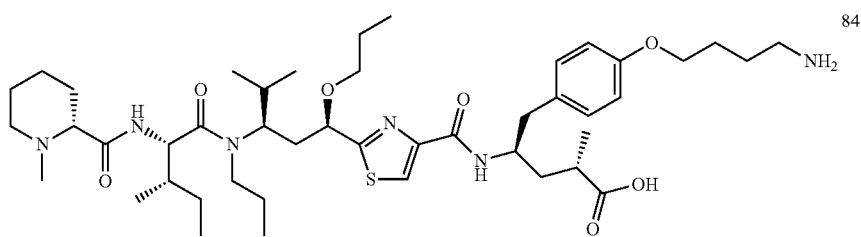 | 843.1 | |
| TAM428 | 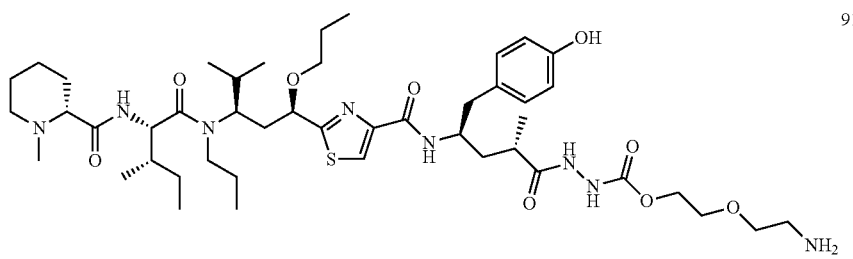 | 916.5 | MCF7: 20.6<br>T-47D: 32.0<br>MDA-MB-468: 16.8 |
| TPM258 | 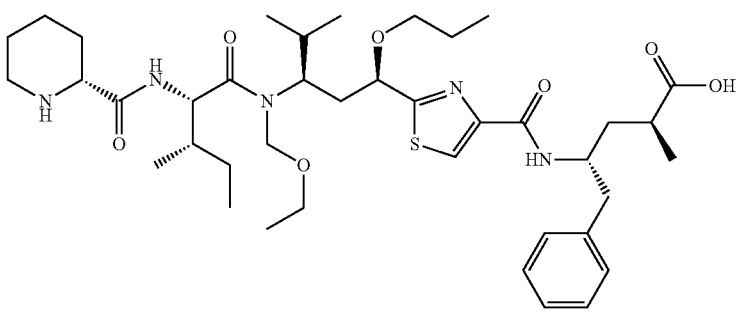 [SMILES: CCCO[C@H](C[C@H](C(C)C)N(COCC)C(=O)[C@@H](NC(=O)[C@H]1CCCCN1)[C@@H](C)CC)c1nc(C(=O)N[C@@H](Cc2ccccc2)C[C@H](C)C(=O)O)cs1] | 758.0 | |
| TPM264 | 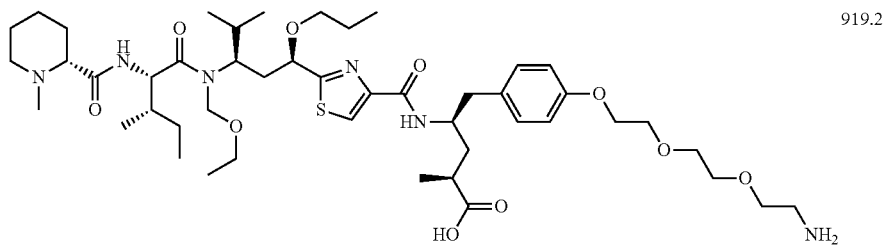 | 919.2 | |
| TPM266 | 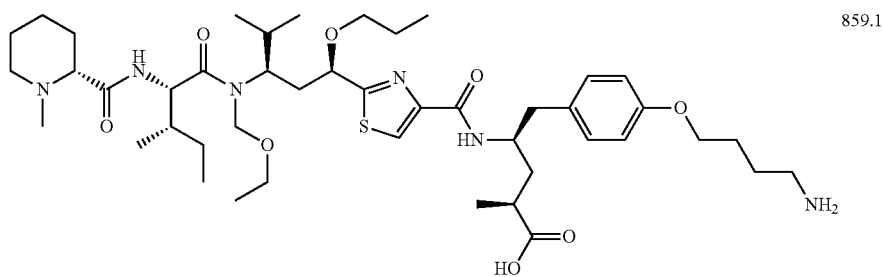 | 859.1 | |
| TPM285 | 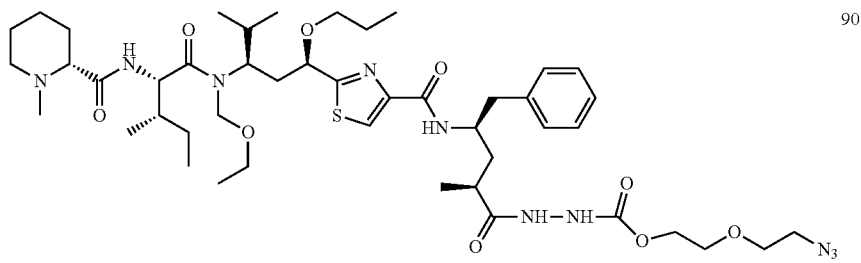 | 900.49 | MCF-7: 0.27<br>T-47D: 0.79<br>MDA-MB-468: 0.64<br>SK.N-MC: 0.50 |

TPM295 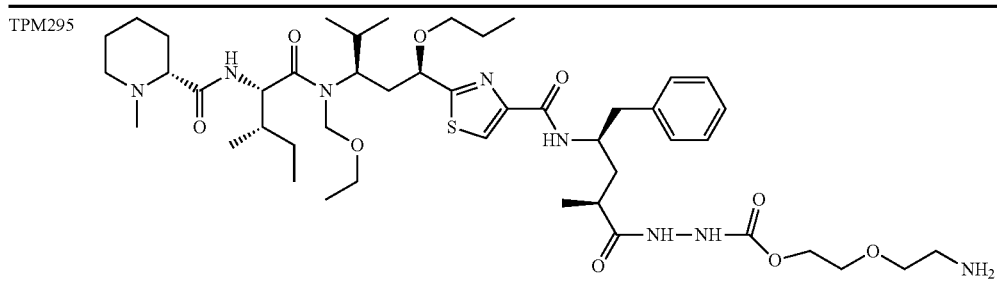

874.50 MCF-7: 8.96
T-47D: 15.0
MDA-MB-468: 10.3
SK.N-MC: 9.83

TAM479 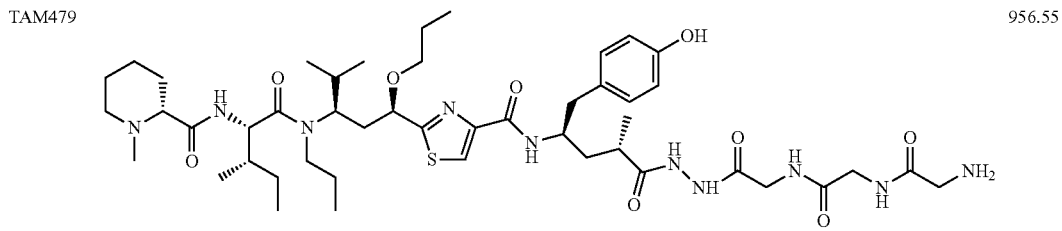

956.55

In general the new molecules of the present invention show an activity against several cancer cell lines between 0.01 to 400 nM.

Possible chemical and enzymatic mediated conjugations of the compounds of the present invention are e.g. amine mediated conjugation, Intein or Sortase A mediated conjugation, TGase mediated conjugation, thiol mediated conjugation and "click chemistry" mediated conjugation, but not limited thereto.

It is the objective of the present invention to provide Tubulysin/Cytolysin derivatives which are modified in such a way that these derivatives can be used either directly or through the further use of an appropriate linker for conjugation to any kind of transport vehicles whether these are targeting molecules or biomolecules, such as proteins, peptides, small molecules or polymeric carriers which can carry a targeting principle.

The described derivatives having an amino function can be used to attach an appropriate linker such as e.g. the valine citrulline maleimide linker useful for the coupling to thiol groups G. M. Dubowchik et al., Bioconjugate Chem 2002, 13, 855-869; S. C. Jeffrey et al., J. Med. Chem. 2005, 48, 1344-1358).

Synthesis of Maleimido-Val-Cit-PABOCO-Tubulysin/Cytolysin-TAM461:

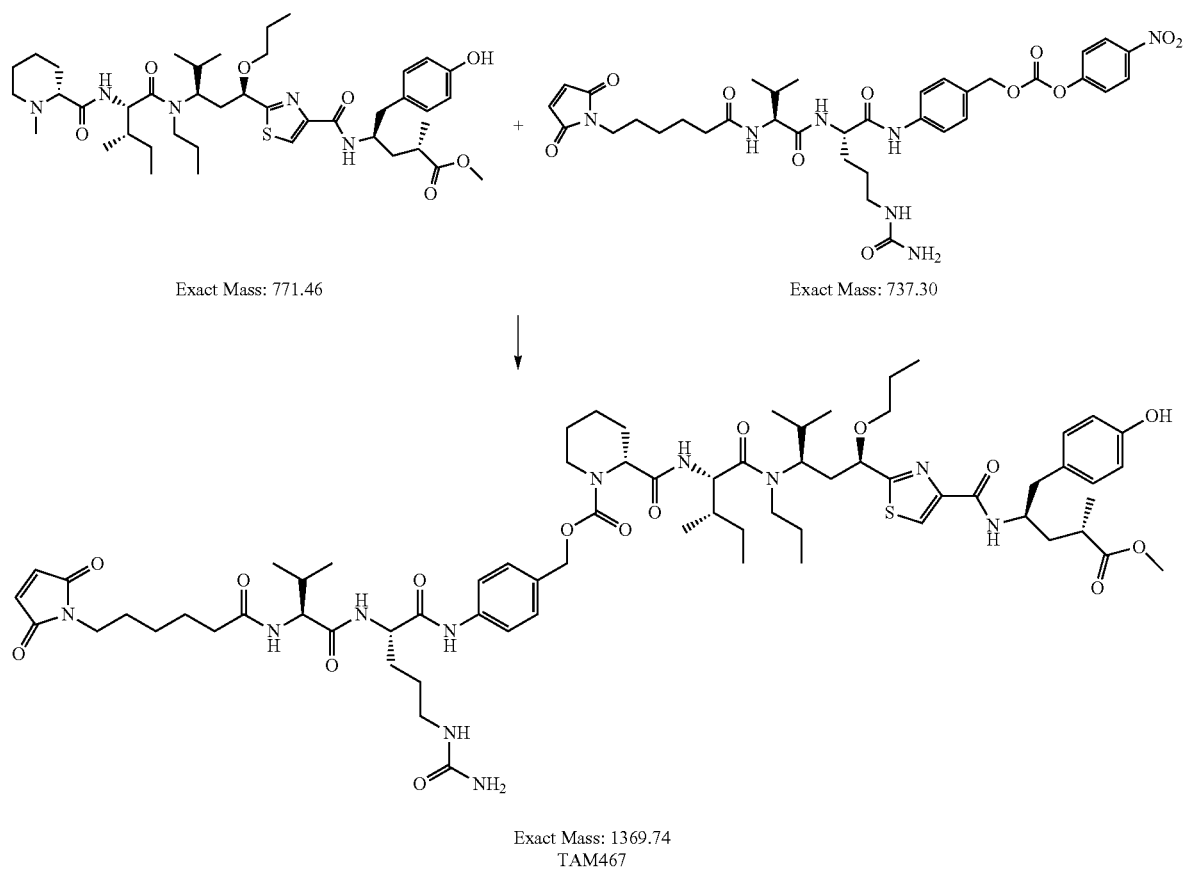

Exact Mass: 1369.74
TAM467

TAM461: 30.0 mg (0.041 mmol)
DMF: 3 mL
TAM465: 35 mg (0.045 mmol)
HOBt: 1.4 mg
DIPEA: 10 μL TAM461 and TAM465 were dissolved in anhydrous DMF under dry conditions and the resulting solution was treated with HOBt and DIPEA. The reaction was stirred at RT for 18 h. The reaction mixture was concentrated and the resulting oil was purified by column chromatography using 2-6% methanol: DCM to give 35 mg (64%) of TAM467 as a white solid. ESI-MS: m/z=1371 [M+H].

Synthesis of Maleimido-Val-Cit-PABOCO-Tubulysin/Cytolysin-TAM470:

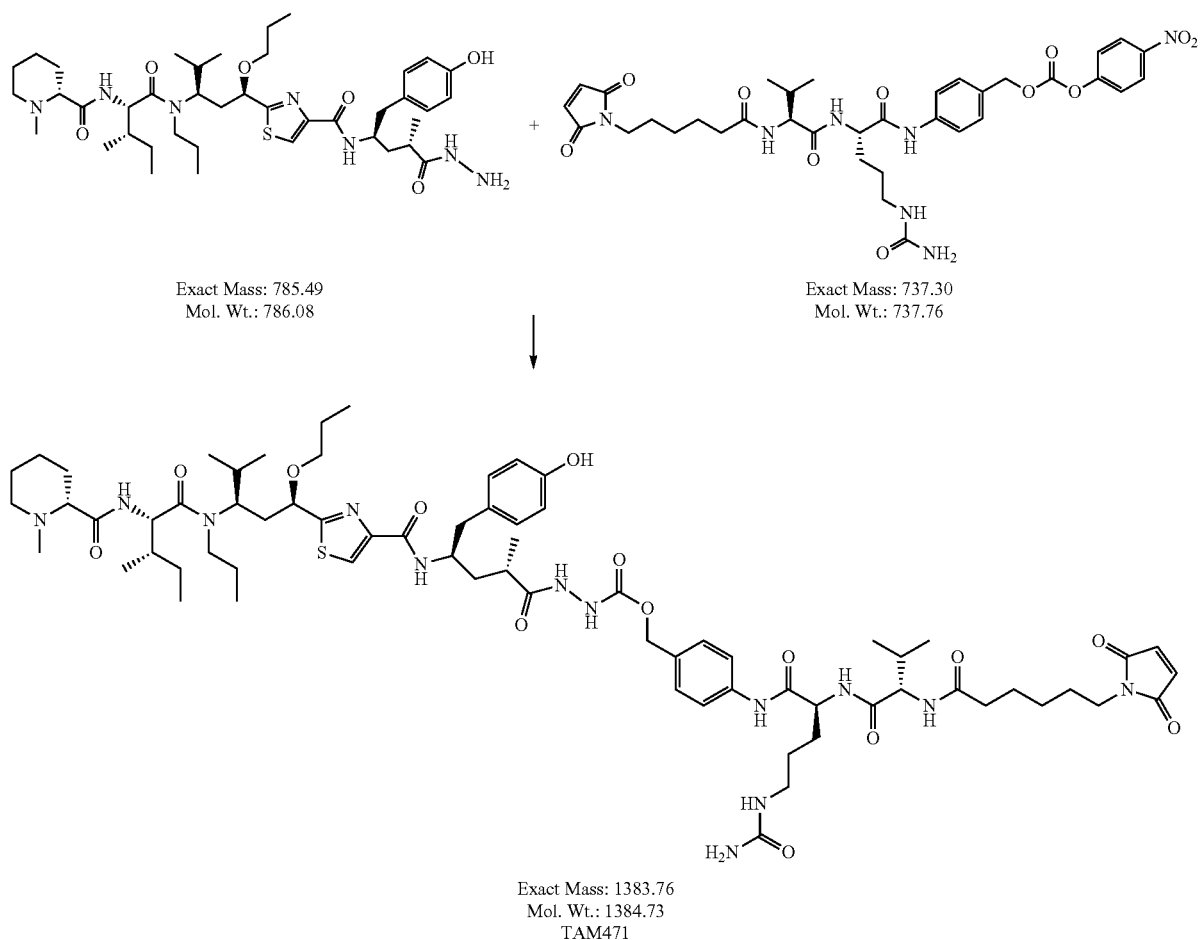 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NN)cs1 ; CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1 ; CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCc2ccc(NC(=O)[C@H](CCCNC(N)=O)NC(=O)[C@@H](NC(=O)CCCCCN3C(=O)C=CC3=O)C(C)C)cc2)cs1]

TAM470 (Tubulysin/Cytolysin): 0.07 mmol
DMF: 5 mL
TAM466 (Linker): 50 mg (0.065 mmol)
HOBt: 2.4 mg
DIPEA: 18 μL TAM470 and TAM466 were dissolved in anhydrous DMF under dry conditions and the resulting solution was treated with HOBt and DIPEA. The reaction was stirred at RT for 18 h and then analysed with TLC, indicating completion of reaction, The reaction mixture was concentrated and the resulting oil was purified with column chromatography using 4-12% methanol: DCM to give 56 mg of TAM471 (yield: 62%). ESI-MS: 1384.6 [M+1].

Synthesis of Antibody-Drug Conjugates can be synthesized using the appropriate reduced antibodies and TAM467 or TAM471 according to e.g. protocols described in G. M. Dubowchik et al., Bioconjugate Chem. 2002, 13, 855-869.

Further Examples
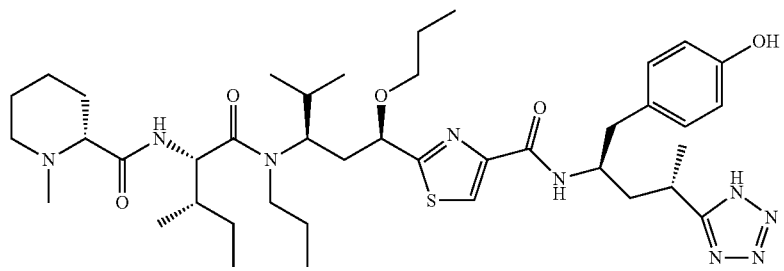
Exact Mass: 795.48
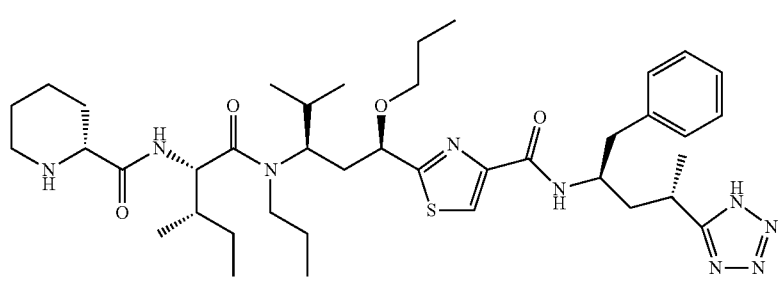
Exact Mass: 765.47
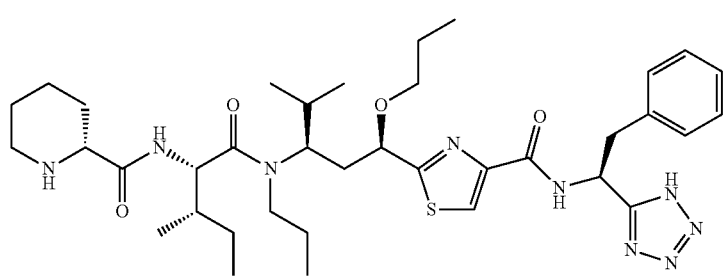
Exact Mass: 723.43
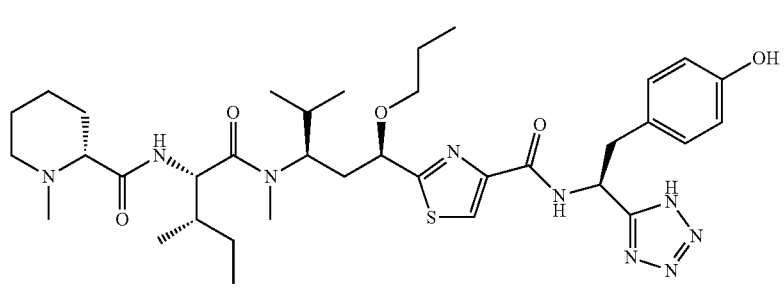
Exact Mass: 725.40
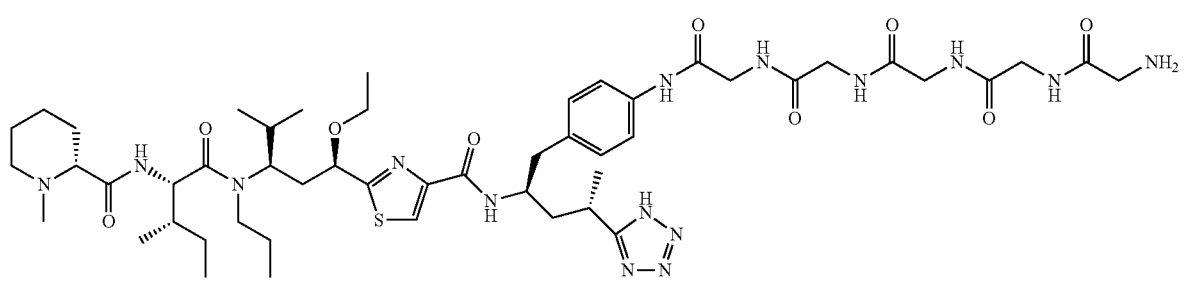
Exact Mass: 1065.59

-continued
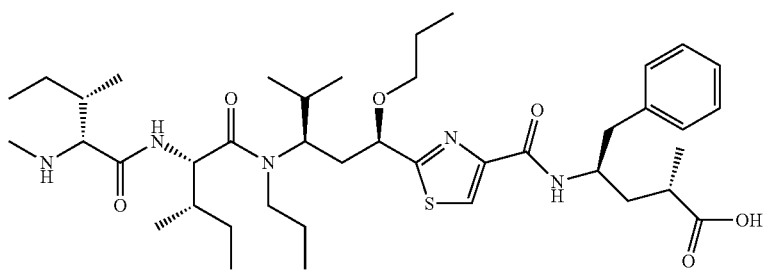
Exact Mass: 757.48
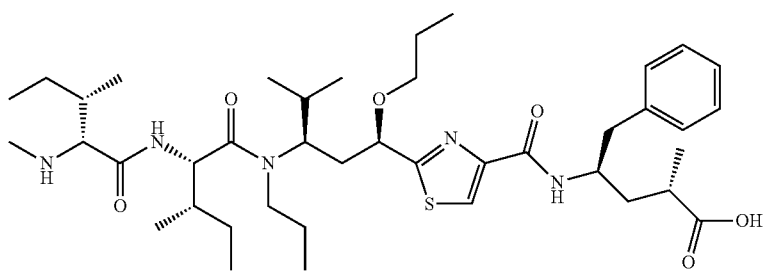
Exact Mass: 757.48
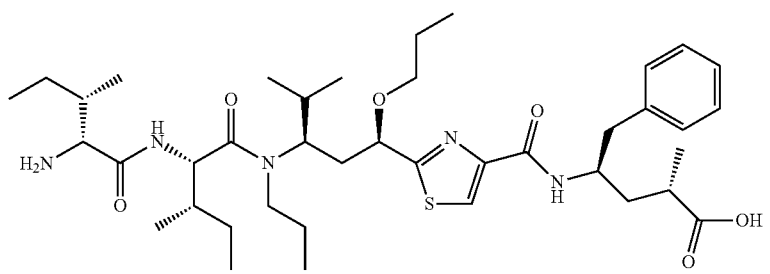
Exact Mass: 743.47
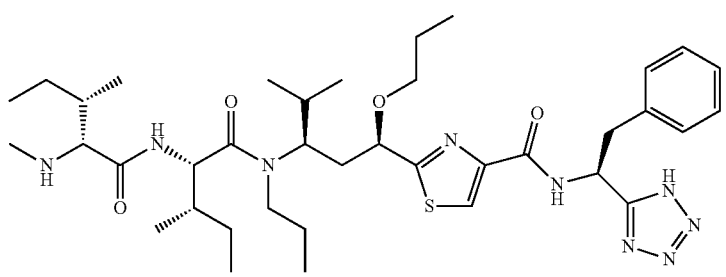
Exact Mass: 739.46
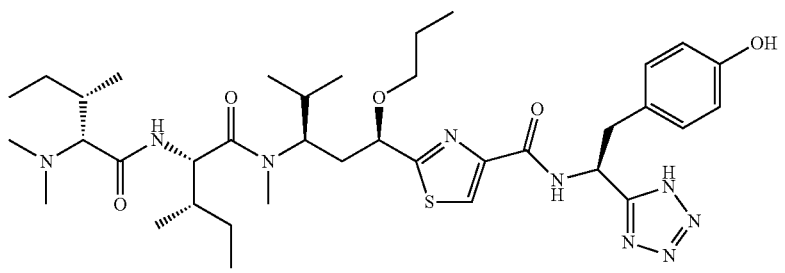
Exact Mass: 741.44

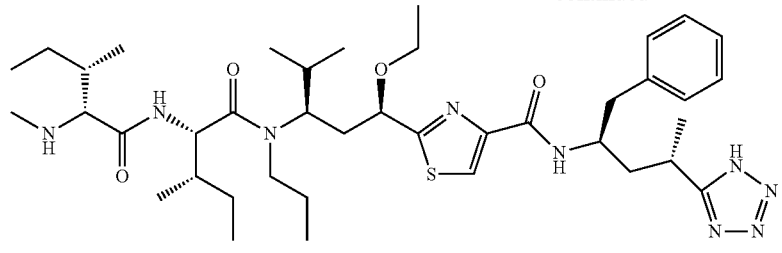

Exact Mass: 767.49

Reaction of the Tubu Tripeptide TPM260 with the Azido-PEG-Phenylalanine Hydrazine TPM283:

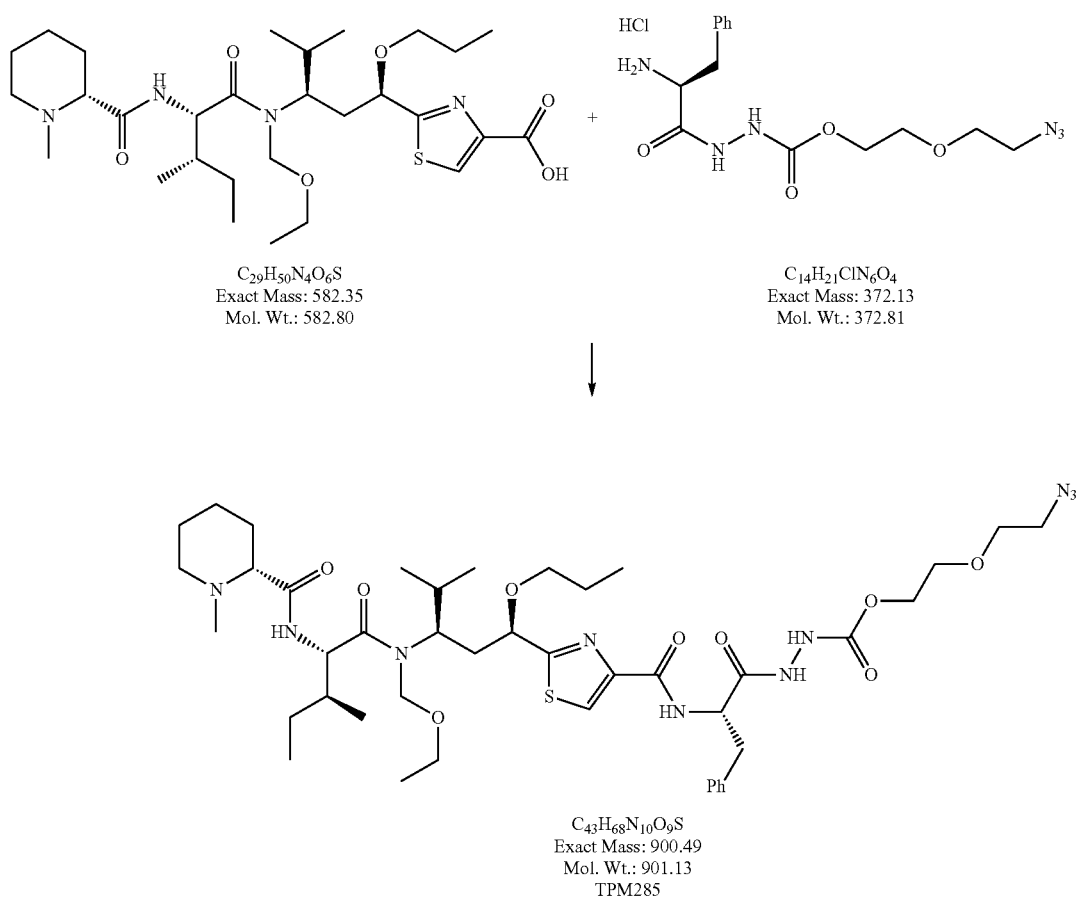 [SMILES: CCCO[C@H](C[C@H](C(C)C)N(COCC)C(=O)[C@@H](NC(=O)[C@H]1CCCCN1C)[C@@H](C)CC)c1nc(C(=O)O)cs1 ; Cl ; [N-]=[N+]=NCCOCCOC(=O)NNC(=O)[C@@H](N)Cc1ccccc1 ; CCCO[C@H](C[C@H](C(C)C)N(COCC)C(=O)[C@@H](NC(=O)[C@H]1CCCCN1C)[C@@H](C)CC)c1nc(C(=O)N[C@@H](Cc2ccccc2)C(=O)NNC(=O)OCCOCCN=[N+]=[N-])cs1]

To a solution of the acid (TPM260, 279 mg, 0,478 mmol) in 5 ml dry DMF, DIPEA (0.18 ml, 2.1 eq.), HO-At (72 mg, 1.1 eq.) and EWG*HCl (97 mg, 1.05 eq.) were added. The solution was stirred at room temperature for 15 min. and a solution of the amine (TPM283, 232 mg) in 1 ml dry DMF were added. The mixture was stirred for 24 hours at room temperature. The reaction mixture was diluted with ether and brine. The organic phase was separated and washed again with brine. The combined organic phases were dried ($Na_2SO_4$) and concentrated in vacuo. The crude product was chromatographed (silica, dichloromethane:methanol 97:3→96:4). 279 mg of TPM285 were obtained (69% yield).

Reduction of the Azide TPM285 to the Amine TPM295:

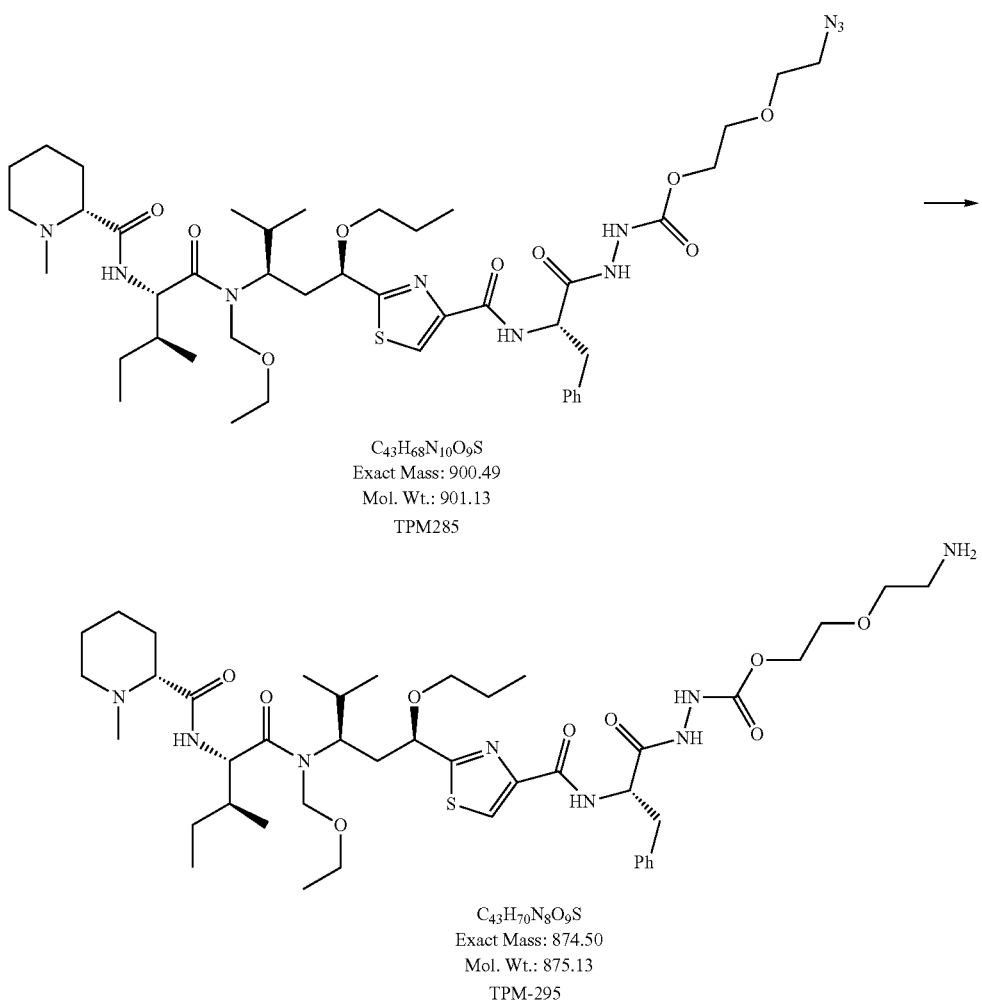

The azide (TPM285, 9.6 mg) was dissolved in 2 ml dry ethanol under Ar and a 10% Pd/C was added. Ar was changed to hydrogen (1 atm.) and the suspension was stirred for 5 h at room temperature. Pd/C was filtered through a pad of Celite and washed with dichloromethane. Concentration in vacuo gave 12 mg of TPM295.

The same described derivatives having an primary amino function can be used for an enzymatic coupling with the enzyme Transglutaminase to biomolecules having a glutamine at appropriate positions, e.g. antibodies (G. Pasut, F. M. Veronese, State of the Art in PEGylation: The great versatility achieved after forty years of research, J. Control. Release (2012) 161, 461-472 and references cited therein).

Synthesis of Antibody-Drug Conjugates using Herceptin™ and TAM375 and TGase was performed according to procedures known to a person skilled in the art with different Drug Antibody Ratios (DAR) of one and two.

FIG. 1 shows dose-response curves of the in-vitro cytotoxic activity of TAM375 ADC-1 and TAM375 ADC-2 against the SK-BR-3 human breast cancer cell line. TAM-375 ADC-1 has an IC50 [M] of 2.246e-010 and TAM-375 ADC-2 has an IC50 [M] of 1.257e-010.

The derivatives described in this invention having an azide function can be used for an coupling utilizing the so-called Click chemistry whereby the counterpart has an alkyne function. The same type of chemistry can be used with an reverse order of function groups, i.e. having an alkyne spacer group on the Tubulysin/Cytolysin and an azide function at the molecule which is going to be conjugated (J. M. Baskin et al., PNAS, 2007, 104 (43), 16793-16797; E. M. Sletten et al., 2011 Acc. Chem. Res. 2011, 44 (9) 666-676; M. K Schultz et al., Org. Lett. 2010, 12, 2398-401; F. Schoenebeck et al., JACS 2009, 131, 8121-8133).

The derivatives described in this invention having an glycine tag of three to 10 glycins on the appropriate positions of the tubulysins/cytolysins can be used for an enzymatic coupling with the enzyme Sortase having the required sequence of LPXTG at the molecule which is going to be conjugated (Lit.: G. Pasut, F. M. Veronese, State of the Art in PEGylation: The great versatility achieved after forty years of research, J. Control. Release (2012) 161, 461-472; M. W.-L. Popp, H. L. Ploegh, Making and Breaking Peptide Bonds: Protein Engineering Using Sortase, Ang. Chemie Int. Ed. 2011, 50, 5024-5032).

Additional Examples

The following compounds have been synthesized in analogy to the procedures described above:

| Name | Structure | MS data [M + H] | IC50 [nM] |
|---|---|---|---|
| TAM484 | 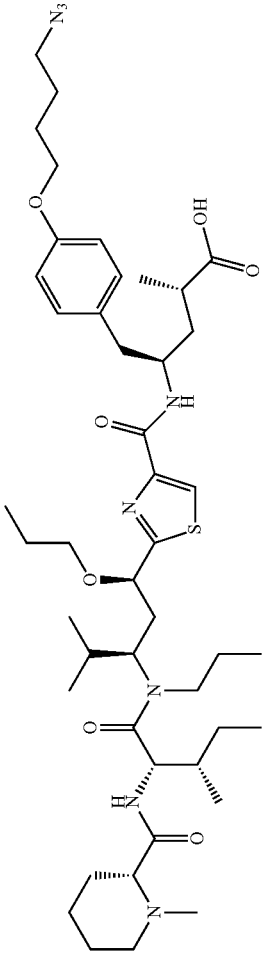 | 869.6 | |
| TAM486 (= TAM405) | 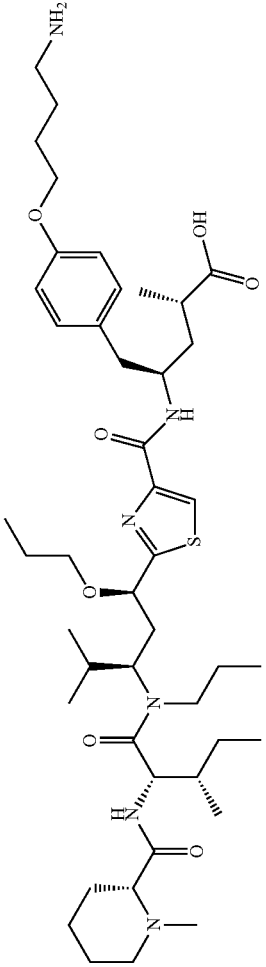 | 843.5 | SK-N-MC 48.5<br>BT-474 50.9<br>MDA-MB-468 81.5<br>MCF-7 57.5<br>T-47D 142.0 |
| TAM487 | 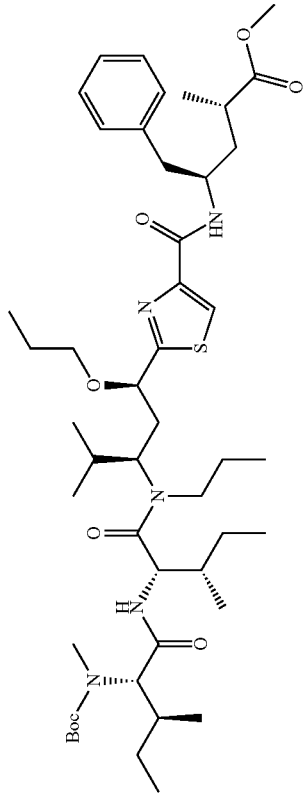 | 872.5 | |

-continued

| Name | Structure | MS data [M + H] | IC50 [nM] |
|---|---|---|---|
| TAM489 | 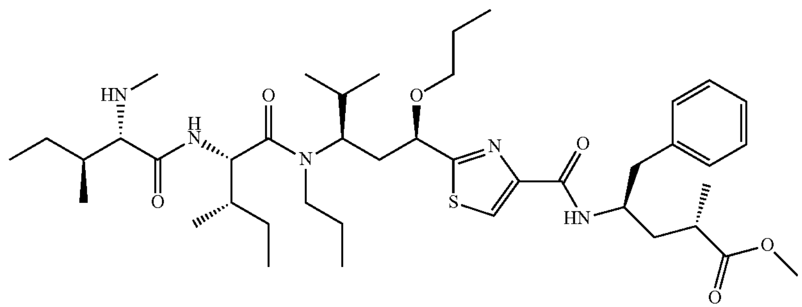 [SMILES: CCCO[C@H](C[C@H](C(C)C)N(CCC)C(=O)[C@@H](NC(=O)[C@@H](NC)[C@@H](C)CC)[C@@H](C)CC)c1nc(C(=O)N[C@@H](Cc2ccccc2)C[C@H](C)C(=O)OC)cs1] | 772.5 | |
| TAM491 | 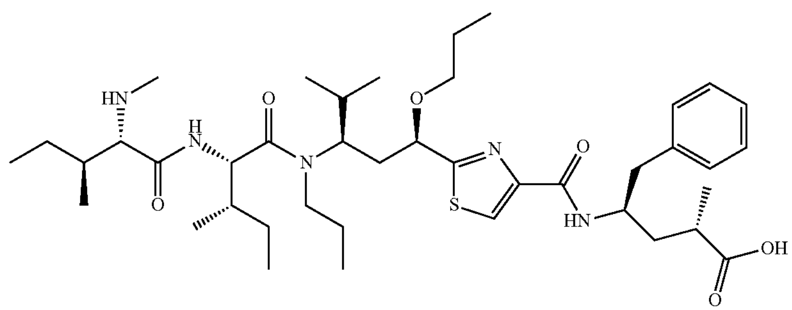 [SMILES: CCCO[C@H](C[C@H](C(C)C)N(CCC)C(=O)[C@@H](NC(=O)[C@@H](NC)[C@@H](C)CC)[C@@H](C)CC)c1nc(C(=O)N[C@@H](Cc2ccccc2)C[C@H](C)C(=O)O)cs1] | 758.5 | SK-N-MC 4.57<br>BT-474 1.84<br>MCF-7 1.77<br>MDA-MB-468 2.68 |
| TAM494 | 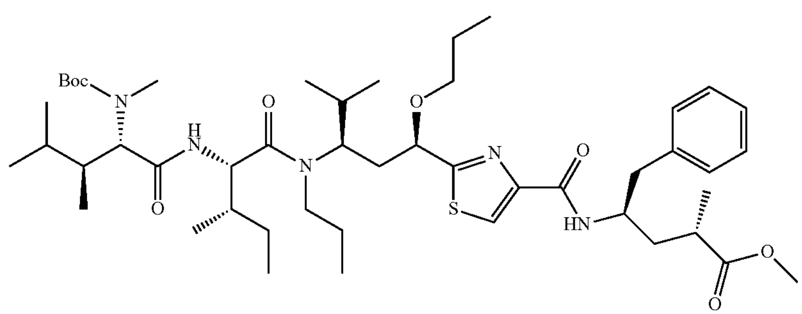 [SMILES: CCCO[C@H](C[C@H](C(C)C)N(CCC)C(=O)[C@@H](NC(=O)[C@H]([C@@H](C)C(C)C)N(C)C(=O)OC(C)(C)C)[C@@H](C)CC)c1nc(C(=O)N[C@@H](Cc2ccccc2)C[C@H](C)C(=O)OC)cs1] | 872.6 | |

-continued

| Name | Structure | MS data [M + H] | IC50 [nM] |
|---|---|---|---|
| TAM496 | 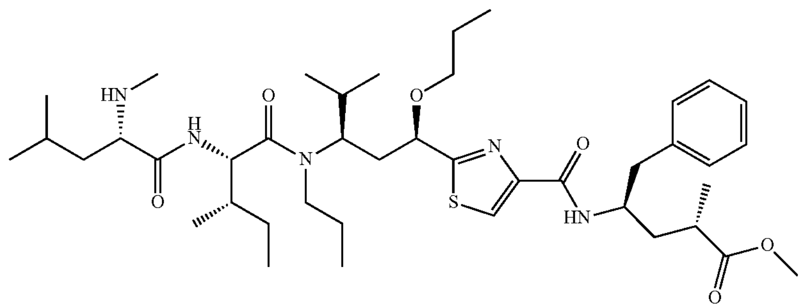 [SMILES: CCCO[C@H](C[C@H](C(C)C)N(CCC)C(=O)[C@@H](NC(=O)[C@H](CC(C)C)NC)[C@@H](C)CC)c1nc(C(=O)N[C@@H](Cc2ccccc2)C[C@H](C)C(=O)OC)cs1] | 772.5 | MCF-7 103.0<br>BT-474 95.2<br>MDA-MB-468 214.0<br>SK-N-MC 300 |
| TAM497 | 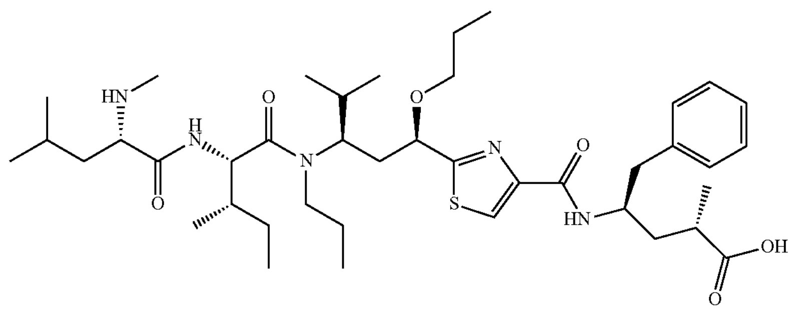 [SMILES: CCCO[C@H](C[C@H](C(C)C)N(CCC)C(=O)[C@@H](NC(=O)[C@H](CC(C)C)NC)[C@@H](C)CC)c1nc(C(=O)N[C@@H](Cc2ccccc2)C[C@H](C)C(=O)O)cs1] | 758.5 | MCF-7 64.3<br>BT-474 50.0<br>MDA-MB-468 85.6<br>SK-N-MC 83.3 |
| TAM507 | 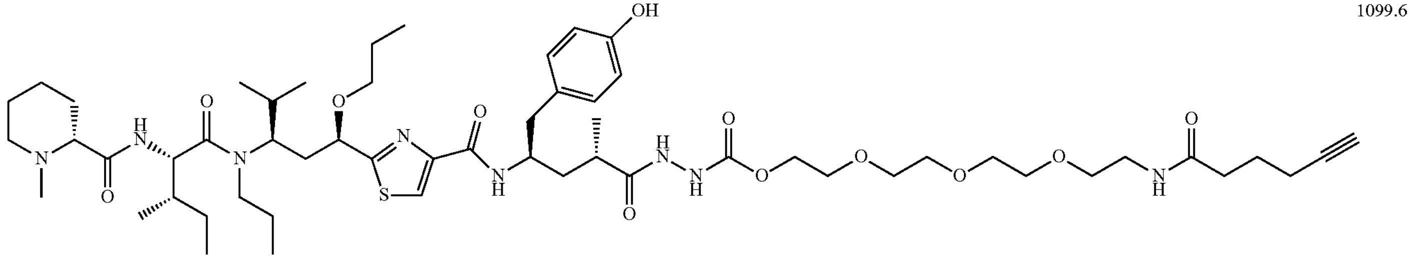 | 1099.6 | |

-continued

| Name | Structure | MS data [M + H] | IC50 [nM] |
|---|---|---|---|
| TAM508 | 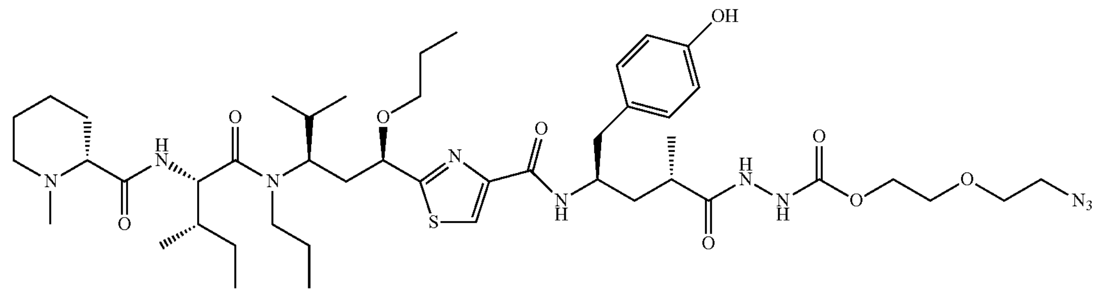 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCN=[N+]=[N-])cs1] | 943.5 | |
| TAM509 (= TAM428) | 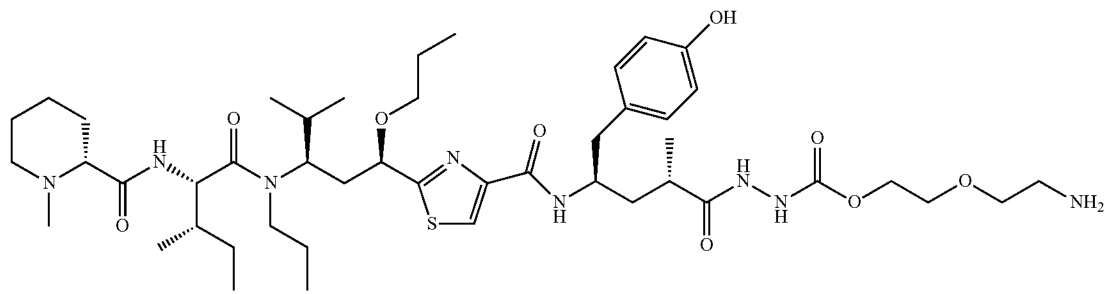 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCN)cs1] | 917.5 | As ADC with Herceptin and DAR 2: 0.219 |
| TAM510 | 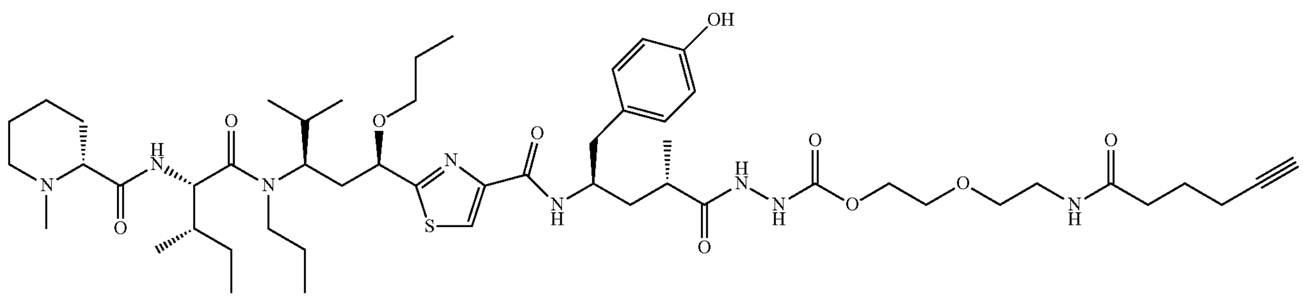 [SMILES: C#CCCCC(=O)NCCOCCOC(=O)NNC(=O)[C@@H](C)C[C@H](Cc1ccc(O)cc1)NC(=O)c1csc([C@@H](C[C@H](C(C)C)N(CCC)C(=O)[C@@H](NC(=O)[C@H]2CCCCN2C)[C@@H](C)CC)OCCC)n1] | 1011.6 | |

| Name | Structure | MS data [M + H] | IC50 [nM] |
|---|---|---|---|
| TAM521 | 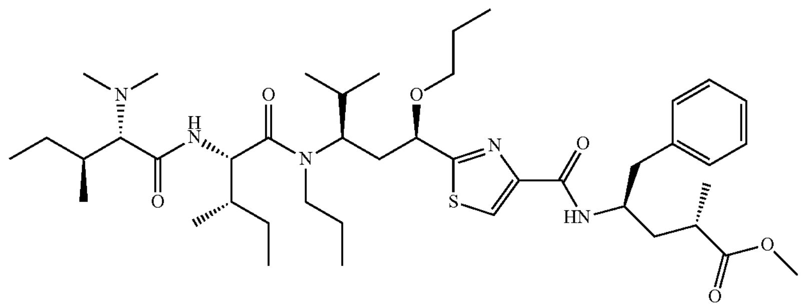 [SMILES: CCCO[C@H](C[C@H](C(C)C)N(CCC)C(=O)[C@@H](NC(=O)[C@H]([C@@H](C)CC)N(C)C)[C@@H](C)CC)c1nc(C(=O)N[C@@H](Cc2ccccc2)C[C@H](C)C(=O)OC)cs1] | 786.5 | MCF-7 6.74<br>BT-474 4.07<br>MDA-MB-468 20.0<br>SK-N-MC 15.3 |
| TAM522 | 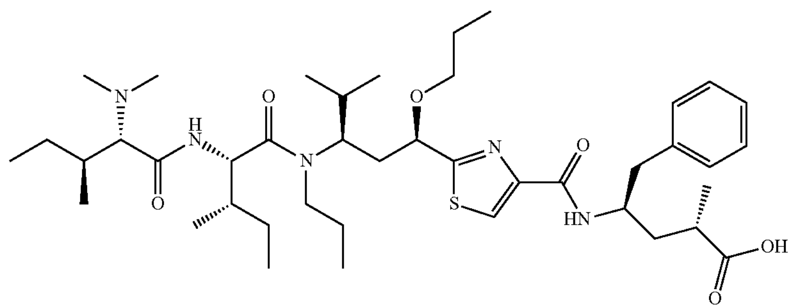 [SMILES: CCCO[C@H](C[C@H](C(C)C)N(CCC)C(=O)[C@@H](NC(=O)[C@H]([C@@H](C)CC)N(C)C)[C@@H](C)CC)c1nc(C(=O)N[C@@H](Cc2ccccc2)C[C@H](C)C(=O)O)cs1] | 772.5 | MCF-7 0.79<br>BT-474 0.98<br>MDA-MB-468 2.0<br>SK-N-MC 1.54 |
| TAM523 | 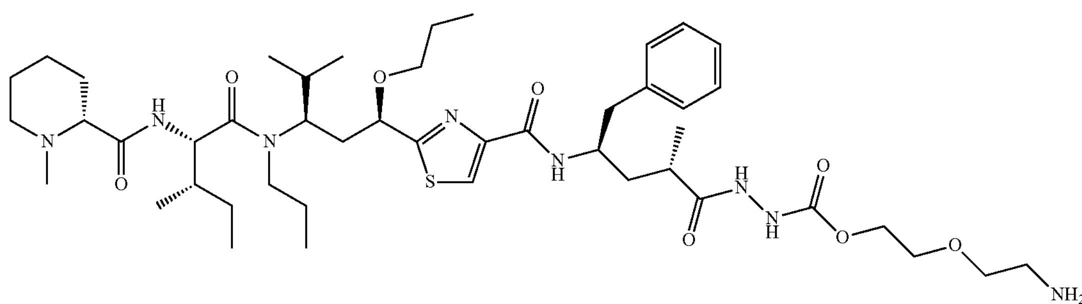 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccccc2)C[C@H](C)C(=O)NNC(=O)OCCOCCN)cs1] | 901.5 | MCF-7 92.1<br>BT-474 65.0<br>MDA-MB-468 221.0<br>SK-N-MC 150.0 |

-continued

| Name | Structure | MS data [M + H] | IC50 [nM] |
|---|---|---|---|
| TAM535 | 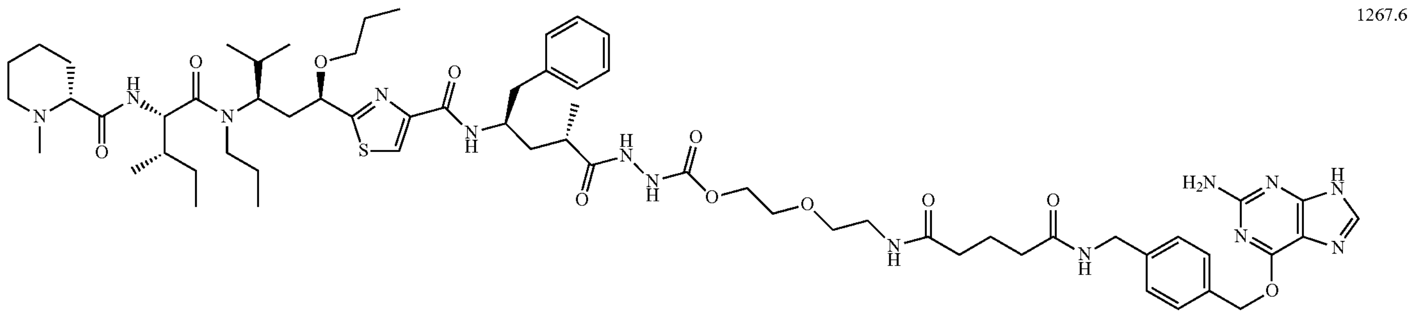 | 1267.6 | |
| TAM550 | 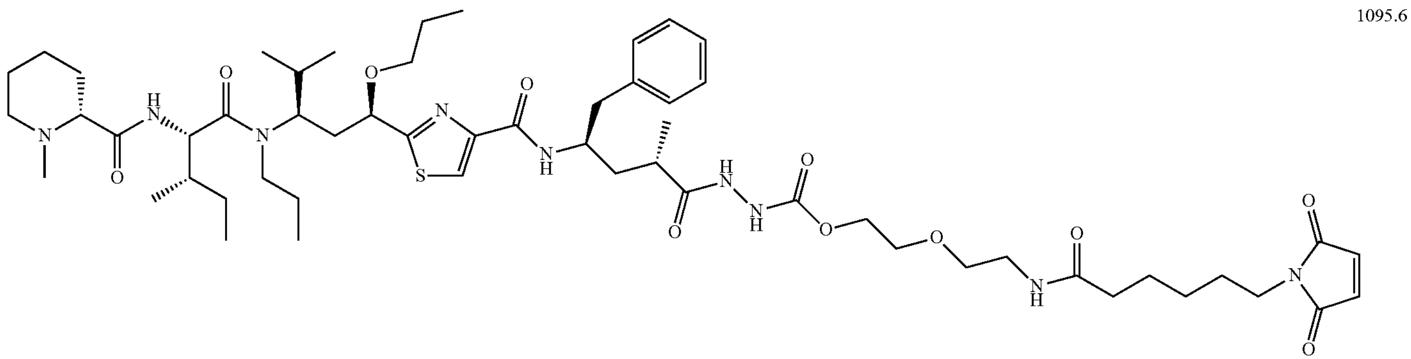 | 1095.6 | |
| TAM551 | 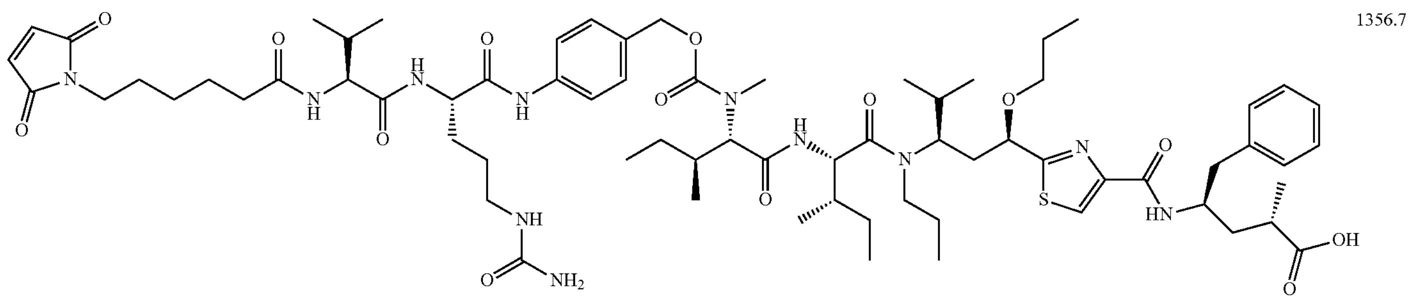 | 1356.7 | HT1080 90.0 |

-continued
| Name | Structure | MS data [M + H] | IC50 [nM] |
|------|-----------|-----------------|-----------|
| TAM552 | 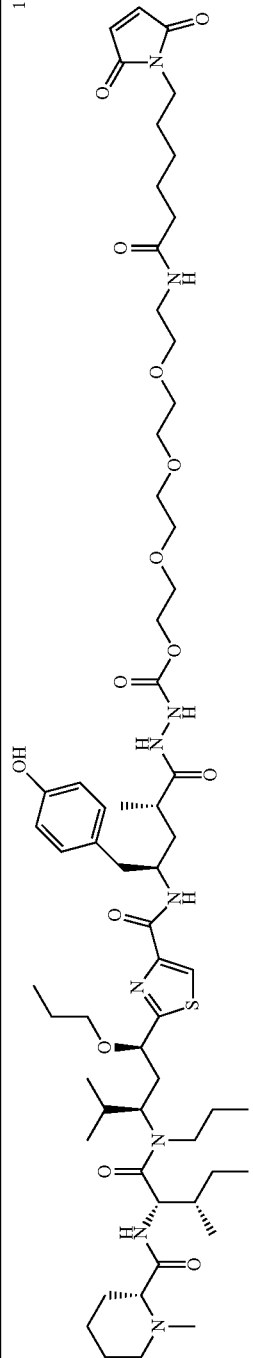 | 1198.6 | HT1080 10.0 |
| TAM553 | 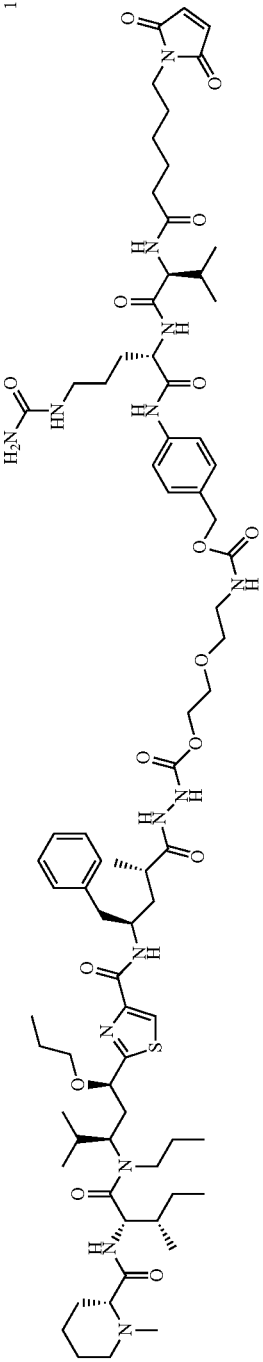 | 1500.8 | HT1080 98.0 |
| TAM556 | 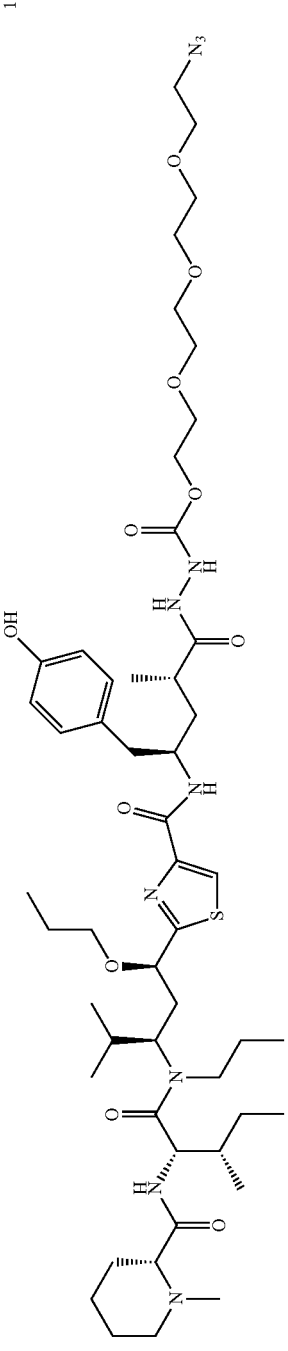 | 1031.6 | |

-continued

| Name | Structure | MS data [M + H] | IC50 [nM] |
|---|---|---|---|
| TAM557 | 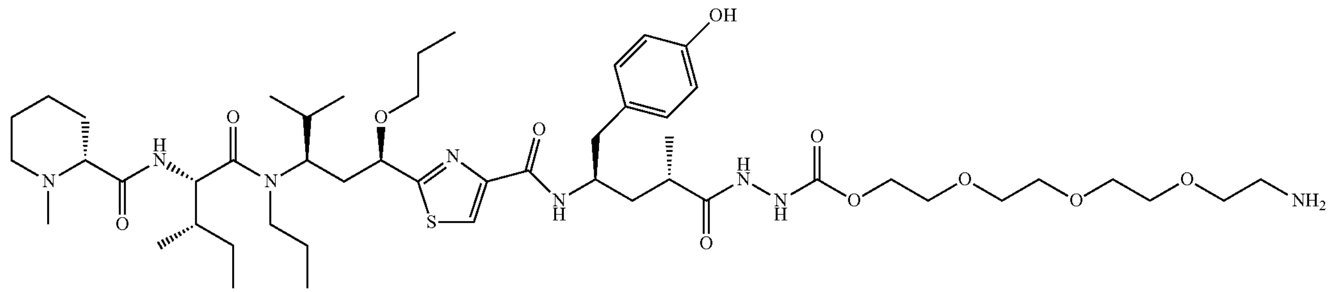 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCOCCOCCN)cs1] | 1005.6 | |
| TAM558 | 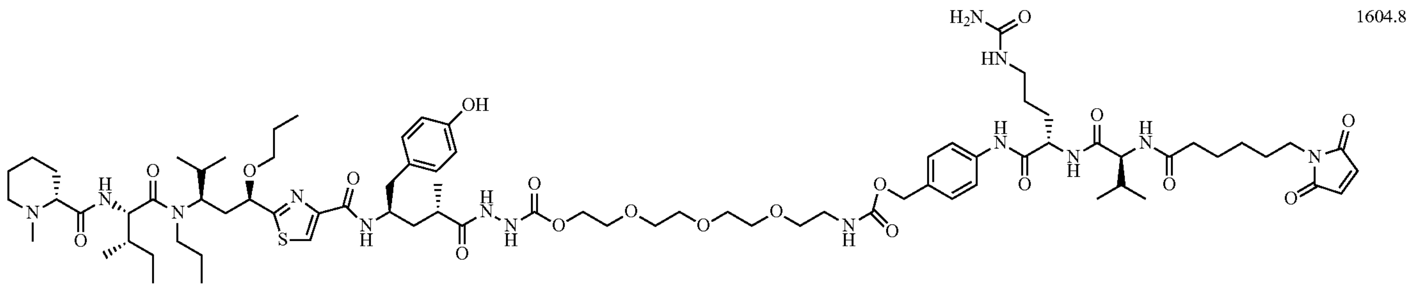 | 1604.8 | HT1080 98.0 |
| TAM559 | 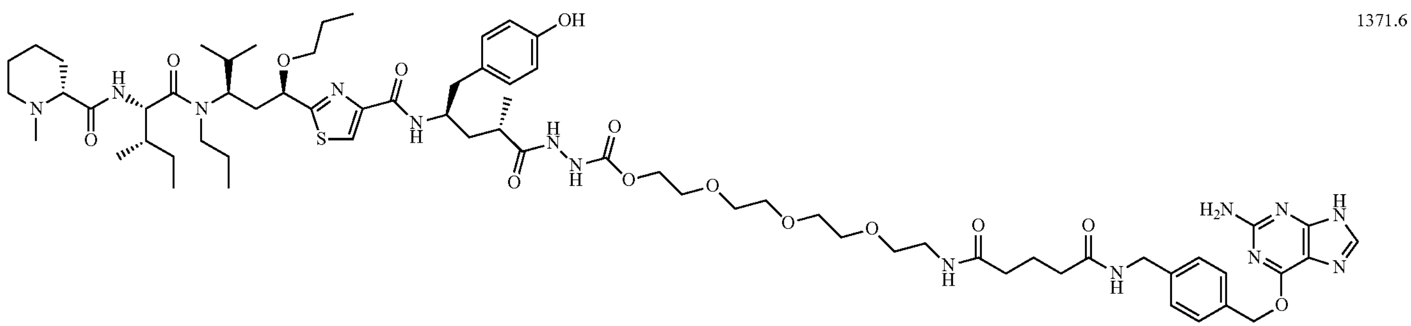 | 1371.6 | |

-continued

| Name | Structure | MS data [M + H] | IC50 [nM] |
|---|---|---|---|
| TAM594 | 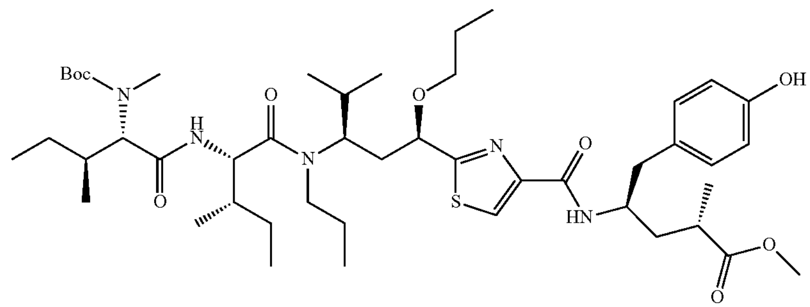 [SMILES: CCCO[C@H](C[C@H](C(C)C)N(CCC)C(=O)[C@@H](NC(=O)[C@H]([C@@H](C)CC)N(C)C(=O)OC(C)(C)C)[C@@H](C)CC)c1nc(C(=O)N[C@@H](Cc2ccc(O)cc2)C[C@H](C)C(=O)OC)cs1] | 888.5 | |
| TAM596 | 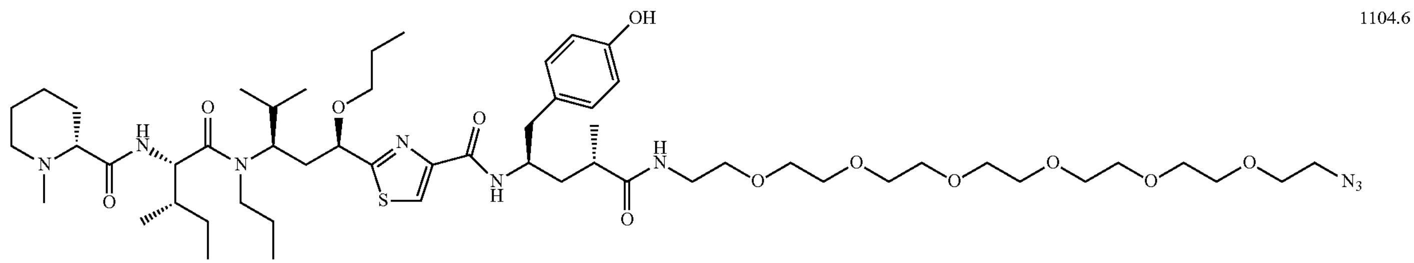 | 1104.6 | |
| TAM597 | 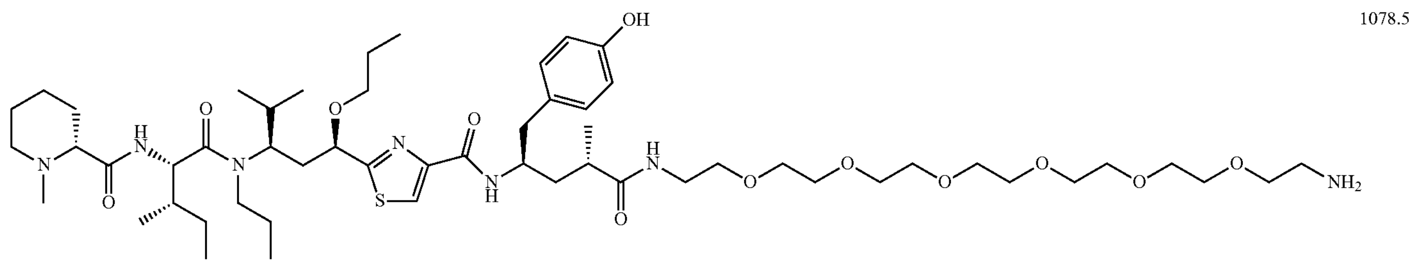 | 1078.5 | As ADC with Herceptin and DAR 2: 0.172 |

-continued

| Name | Structure | MS data [M + H] | IC50 [nM] |
|---|---|---|---|
| TAM598 | 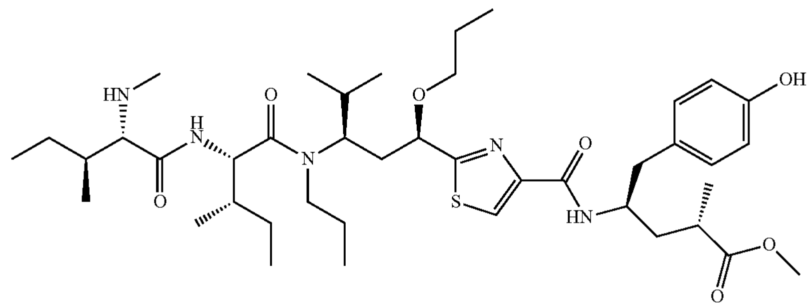 [SMILES: CCCO[C@H](C[C@H](C(C)C)N(CCC)C(=O)[C@@H](NC(=O)[C@@H](NC)[C@@H](C)CC)[C@@H](C)CC)c1nc(C(=O)N[C@@H](Cc2ccc(O)cc2)C[C@H](C)C(=O)OC)cs1] | 788.5 | MCF-7 4.39<br>MDA-MB-468 5.15<br>SK-N-MC 6.74<br>T-47D 8.17 |
| TAM599 | 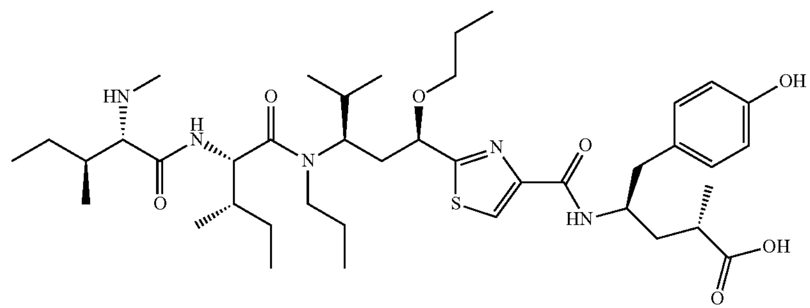 [SMILES: CCCO[C@H](C[C@H](C(C)C)N(CCC)C(=O)[C@@H](NC(=O)[C@@H](NC)[C@@H](C)CC)[C@@H](C)CC)c1nc(C(=O)N[C@@H](Cc2ccc(O)cc2)C[C@H](C)C(=O)O)cs1] | 774.5 | MCF-7 0.65<br>MDA-MB-468 0.64<br>SK-N-MC 0.77<br>T-47D 1.22 |
| TAM601 | 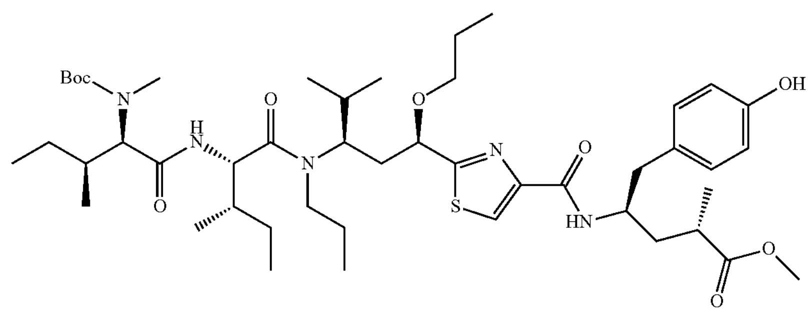 [SMILES: CCCO[C@H](C[C@H](C(C)C)N(CCC)C(=O)[C@@H](NC(=O)[C@@H]([C@@H](C)CC)N(C)C(=O)OC(C)(C)C)[C@@H](C)CC)c1nc(C(=O)N[C@@H](Cc2ccc(O)cc2)C[C@H](C)C(=O)OC)cs1] | 888.5 | |

-continued

| Name | Structure | MS data [M + H] | IC50 [nM] |
|---|---|---|---|
| TAM605/626 | 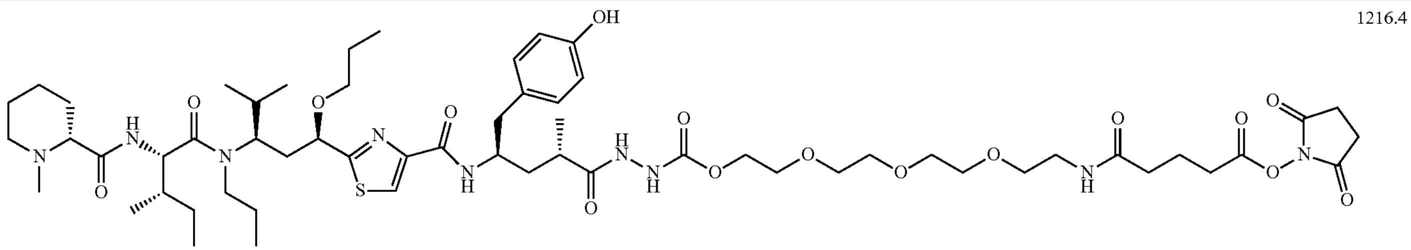 | 1216.4 | |
| TAM606 | 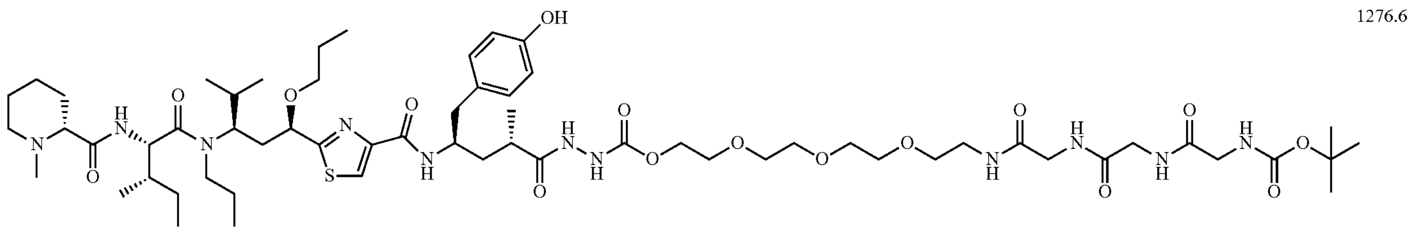 | 1276.6 | |
| TAM607 | 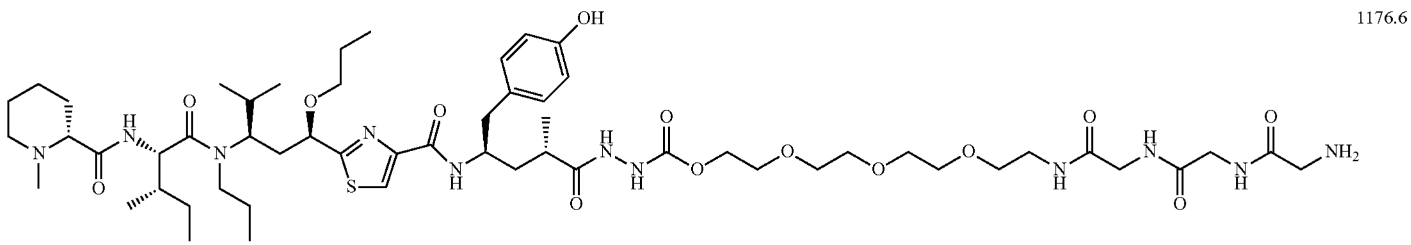 | 1176.6 | |

-continued

| Name | Structure | MS data [M + H] | IC50 [nM] |
|---|---|---|---|
| TAM608 | 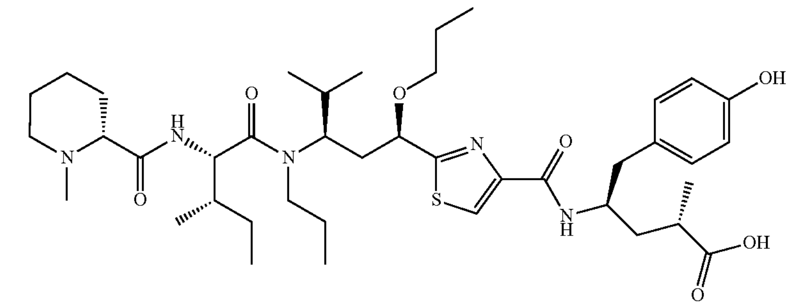 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)O)cs1] | 773.0 | MCF-7 4.06<br>BT-474 1.69<br>MDA-MB-468 2.24<br>SK-N-MC 1.54 |
| TAM609 | 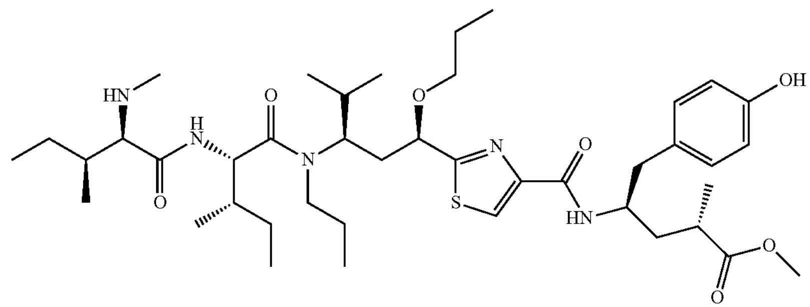 [SMILES: CCCO[C@H](C[C@H](C(C)C)N(CCC)C(=O)[C@@H](NC(=O)[C@H](NC)[C@@H](C)CC)[C@@H](C)CC)c1nc(C(=O)N[C@@H](Cc2ccc(O)cc2)C[C@H](C)C(=O)OC)cs1] | 788.5 | MCF-7 2.17<br>BT-474 0.5<br>MDA-MB-468 3.32<br>SK-N-MC 2.12 |
| TAM610 | 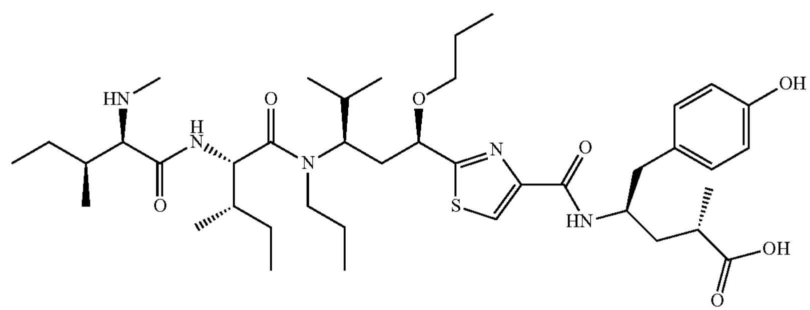 [SMILES: CCCO[C@H](C[C@H](C(C)C)N(CCC)C(=O)[C@@H](NC(=O)[C@H](NC)[C@@H](C)CC)[C@@H](C)CC)c1nc(C(=O)N[C@@H](Cc2ccc(O)cc2)C[C@H](C)C(=O)O)cs1] | 774.5 | MCF-7 0.2<br>BT-474 0.1<br>MDA-MB-468 0.3<br>SK-N-MC 0.1 |

-continued

| Name | Structure | MS data [M + H] IC50 [nM] |
|---|---|---|
| TAM620 | 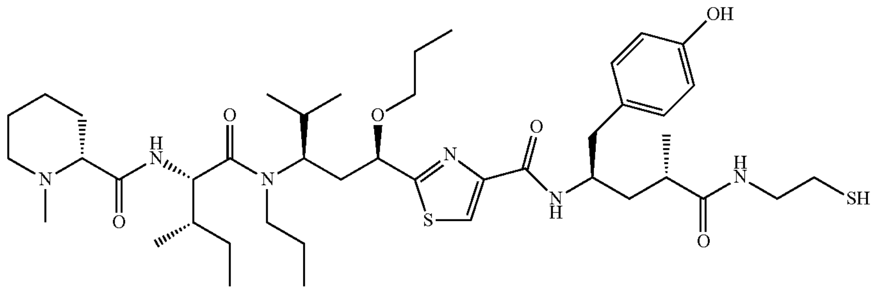 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NCCS)cs1] | 831.5 |
| TAM628 | 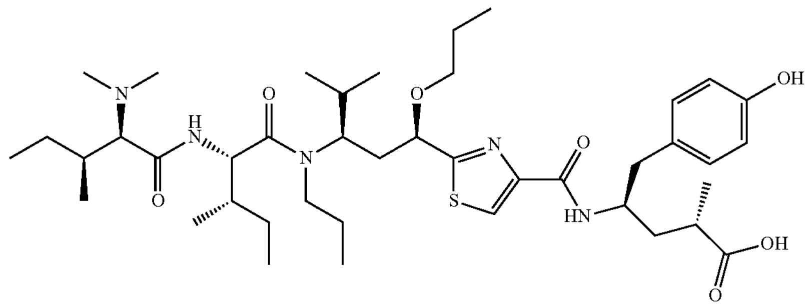 [SMILES: CCCO[C@H](C[C@H](C(C)C)N(CCC)C(=O)[C@@H](NC(=O)[C@@H]([C@@H](C)CC)N(C)C)[C@@H](C)CC)c1nc(C(=O)N[C@@H](Cc2ccc(O)cc2)C[C@H](C)C(=O)O)cs1] | 788.5 |
| TAM649 | 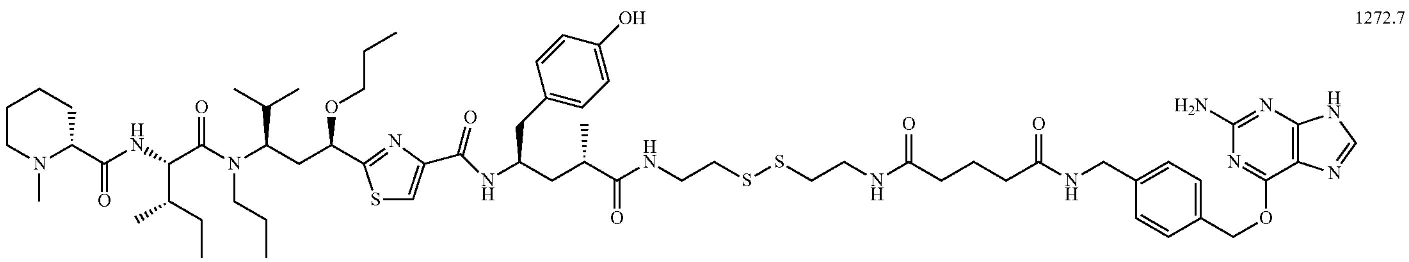 | 1272.7 |

| Name | Structure | MS data [M + H] IC50 [nM] |
|---|---|---|
| TAM663 | 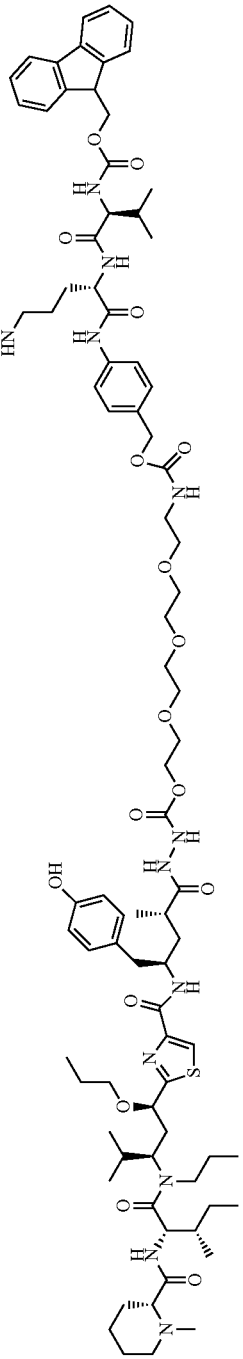 | 1632.8 |
| TAM665 | 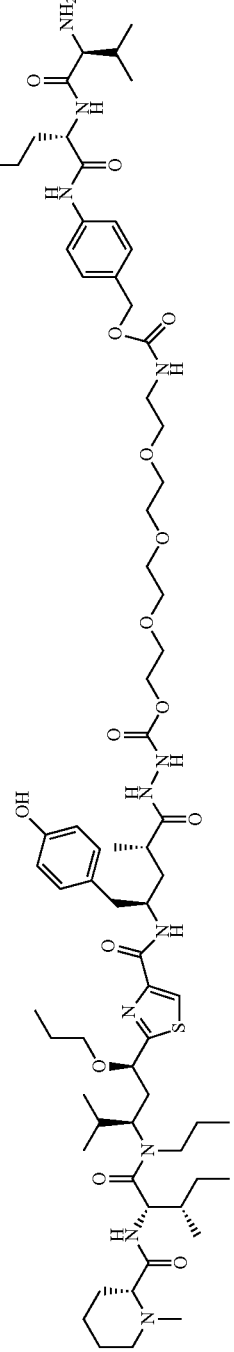 | 1410.5 |

| Name | Structure | MS data [M + H] | IC50 [nM] |
|---|---|---|---|
| TAM666 | 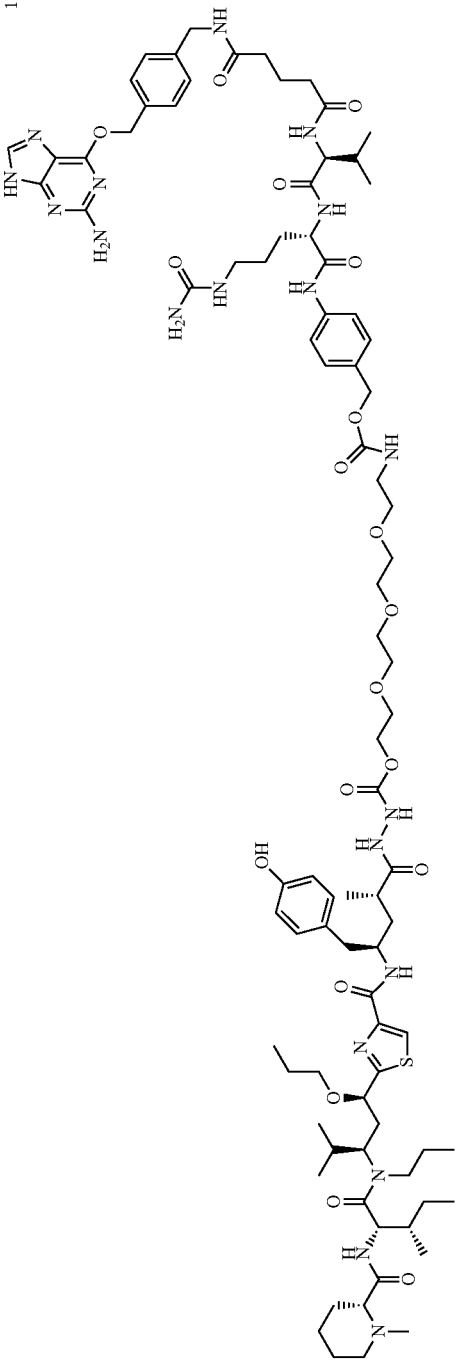 | 1777.6 | |
| TAM674 | 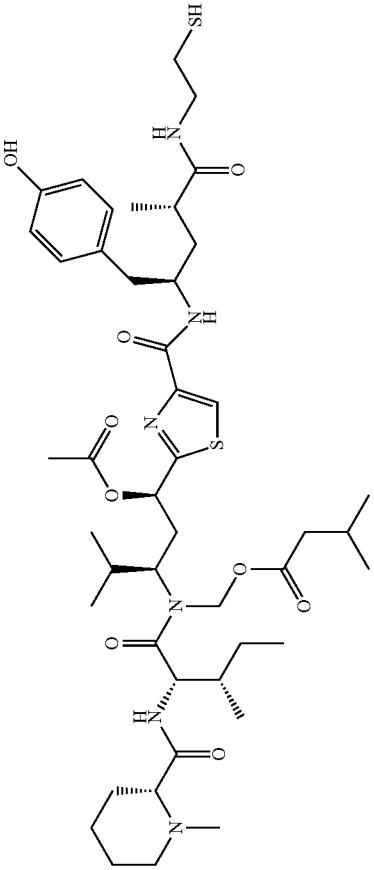 | 903.4 | HT-29 4.4<br>A2780 8.7<br>NCI-H1299 19.0 |

-continued

| Name | Structure | MS data [M + H] | IC50 [nM] |
|---|---|---|---|
| TAM675B | 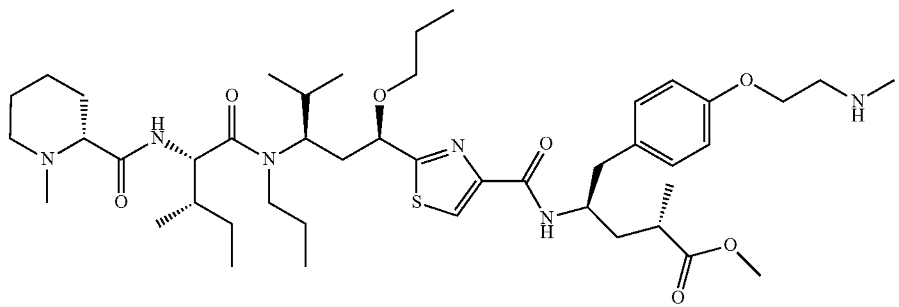 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(OCCNC)cc2)C[C@H](C)C(=O)OC)cs1] | 843.5 | |
| TPM320 | 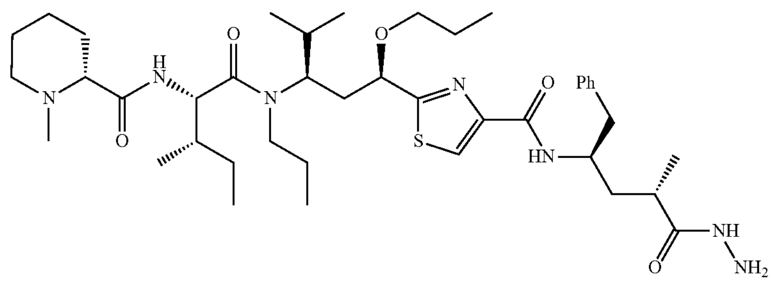 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccccc2)C[C@H](C)C(=O)NN)cs1] | 769.49 | SK-N-MC 16.0 BT-474 11.0 |
| TAM682 | 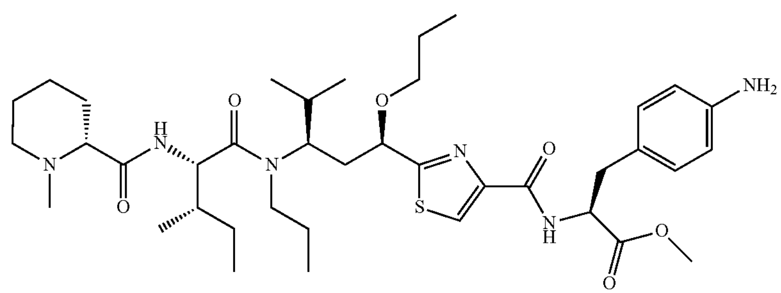 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(N)cc2)C(=O)OC)cs1] | 743.0 | |

-continued

| Name | Structure | MS data [M + H] | IC50 [nM] |
|---|---|---|---|
| TAM683 | 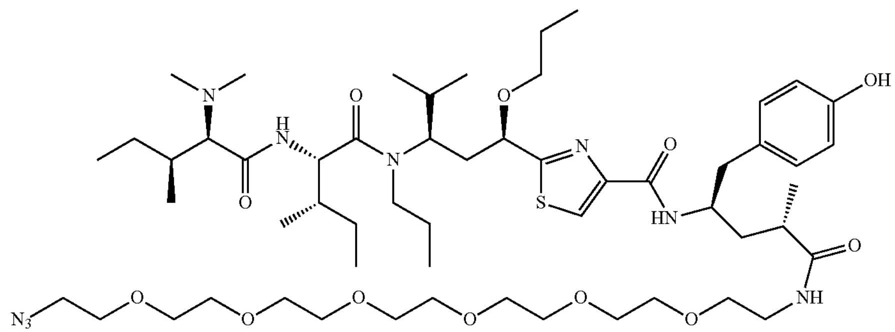 [SMILES: CCCO[C@H](C[C@H](C(C)C)N(CCC)C(=O)[C@@H](NC(=O)[C@@H]([C@@H](C)CC)N(C)C)[C@@H](C)CC)c1nc(C(=O)N[C@@H](Cc2ccc(O)cc2)C[C@H](C)C(=O)NCCOCCOCCOCCOCCOCCOCCN=[N+]=[N-])cs1] | 1120.5 | |
| TAM687 | 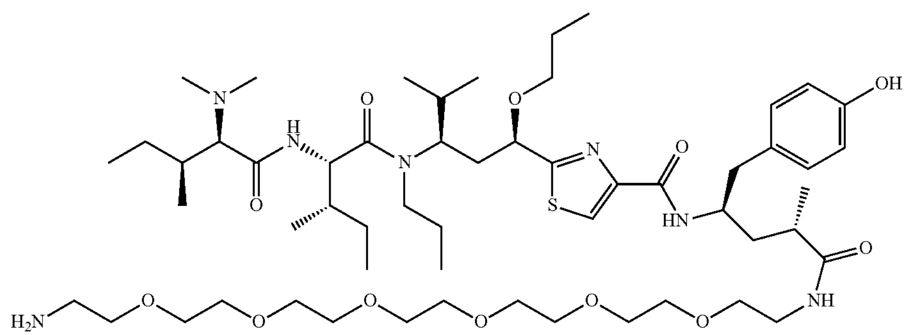 [SMILES: CCCO[C@H](C[C@H](C(C)C)N(CCC)C(=O)[C@@H](NC(=O)[C@@H]([C@@H](C)CC)N(C)C)[C@@H](C)CC)c1nc(C(=O)N[C@@H](Cc2ccc(O)cc2)C[C@H](C)C(=O)NCCOCCOCCOCCOCCOCCOCCN)cs1] | 1094.5 | |

| Name | Structure | MS data [M + H] IC50 [nM] |
|---|---|---|
| | 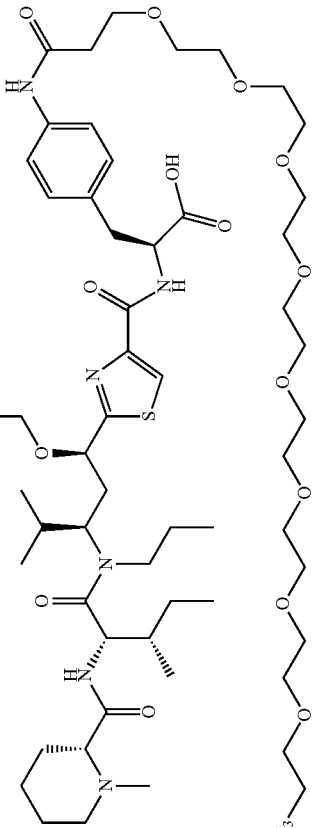 | 1178.5 |
| | 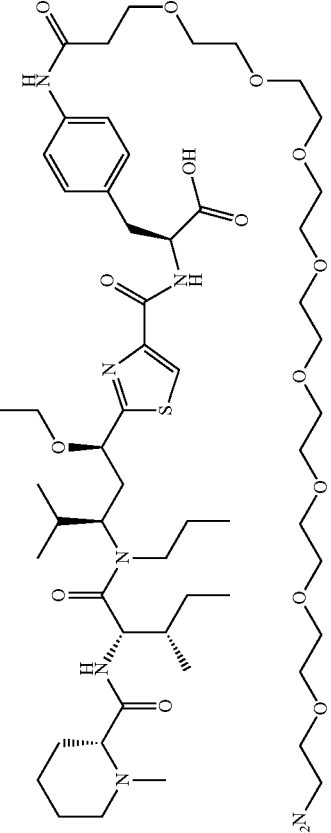 | 1152.5 |

| Name | Structure | MS data [M + H] | IC50 [nM] |
|---|---|---|---|
| — | 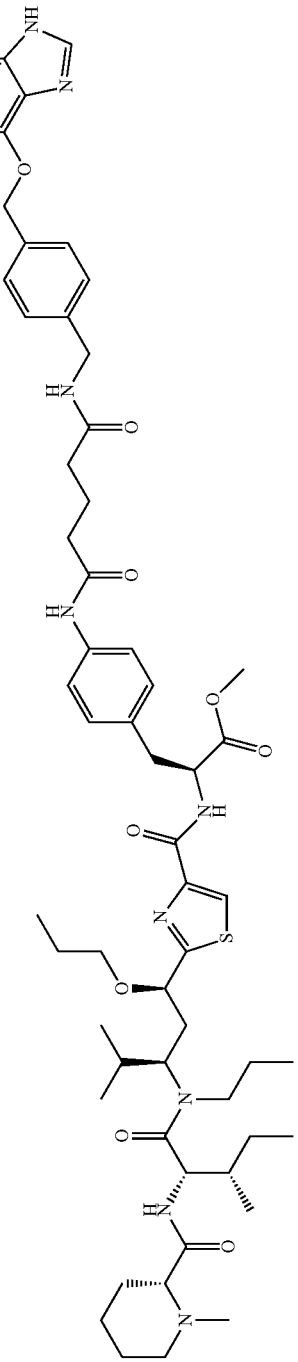 | 1109.4 | |
| — | 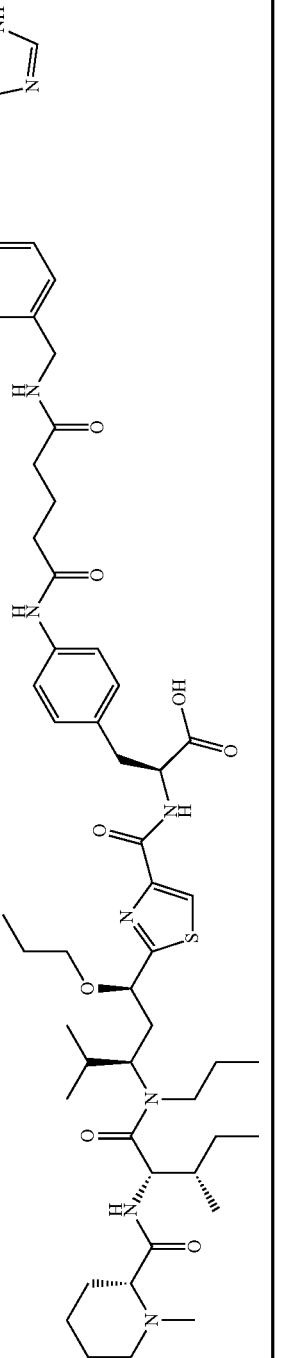 | 1095.4 | |

The invention claimed is:
1. A compound of formula (I)

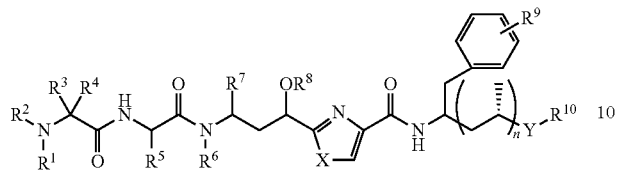

wherein
n is 0 or 1;
X is O or S;
Y is a CO group or a $CH_2$ group or a bond;
$R^2$ and $R^3$ are independently H or an alkyl, cycloalkyl, heteroalkyl or heterocycloalkyl group, all of which may optionally be substituted, or $R^2$ and $R^3$ together are a group of formula $(CH_2)_m$ wherein m is 2, 3, 4 or 5;
$R^4$ is H, an alkyl, cycloalkyl, heteroalkyl or heterocycloalkyl group, all of which may optionally be substituted;
$R^5$ is H, an alkyl, cycloalkyl, heteroalkyl or heterocycloalkyl group, all of which may optionally be substituted;
$R^6$ is H, an alkyl, alkenyl, alkynyl, heteroalkyl, aralkyl or heteroaralkyl group, all of which may optionally be substituted;
$R^7$ is H, an alkyl, alkenyl, alkynyl, heteroalkyl, aralkyl or heteroaralkyl group, all of which may optionally be substituted;
$R^8$ is H, an alkyl, heteroalkyl group, aralkyl or heteroaralkyl group, all of which may optionally be substituted; and
$R^1$ is H, an alkyl group or a heteroalkyl group, all of which may optionally be substituted; and
$R^9$ is H, OH, SH, CN, $NH_2$, $NO_2$, halogen, or an alkyl, heteroalkyl, aryl, heteroaryl, aryloxy or heteroaryloxy group, all of which may optionally be substituted; and
$R_{10}$ is selected from the following groups,

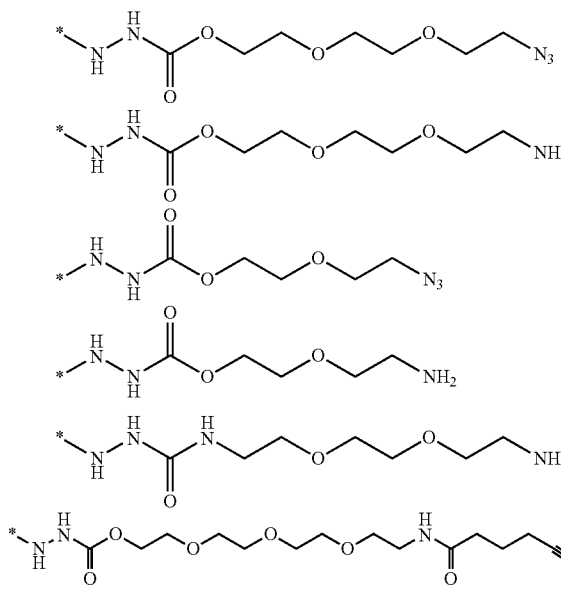

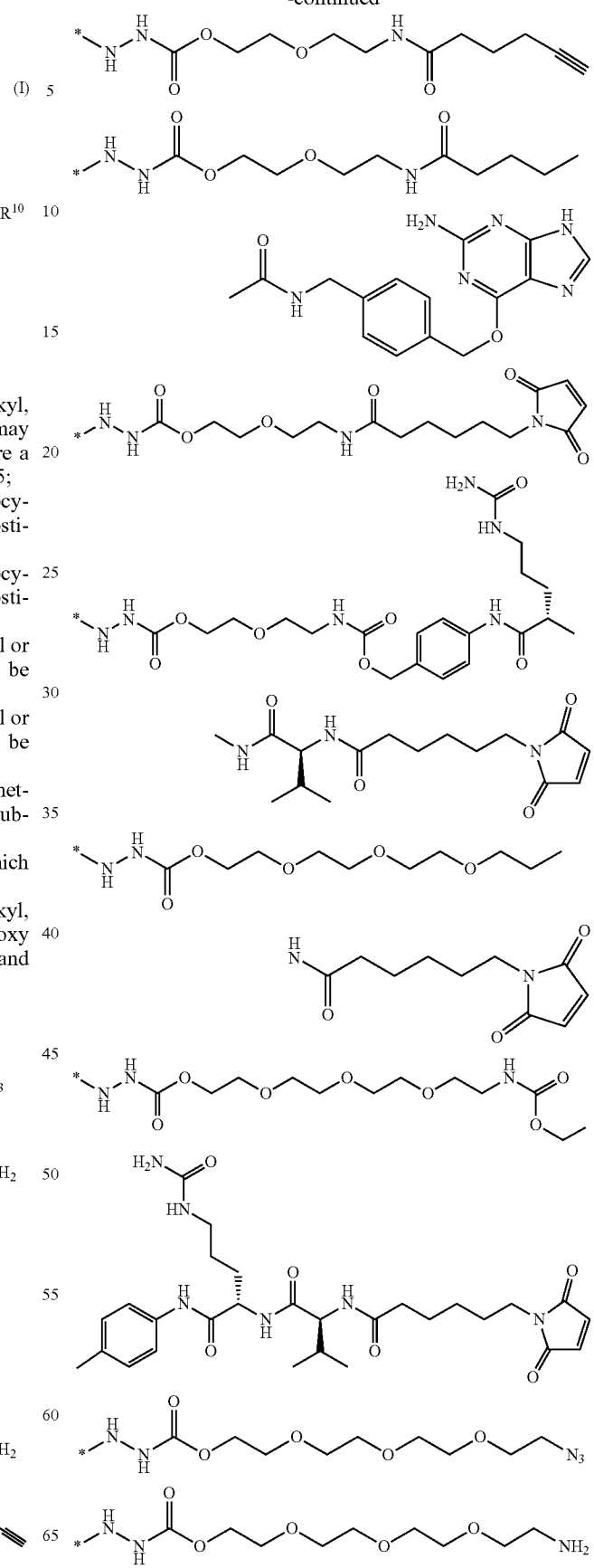

-continued

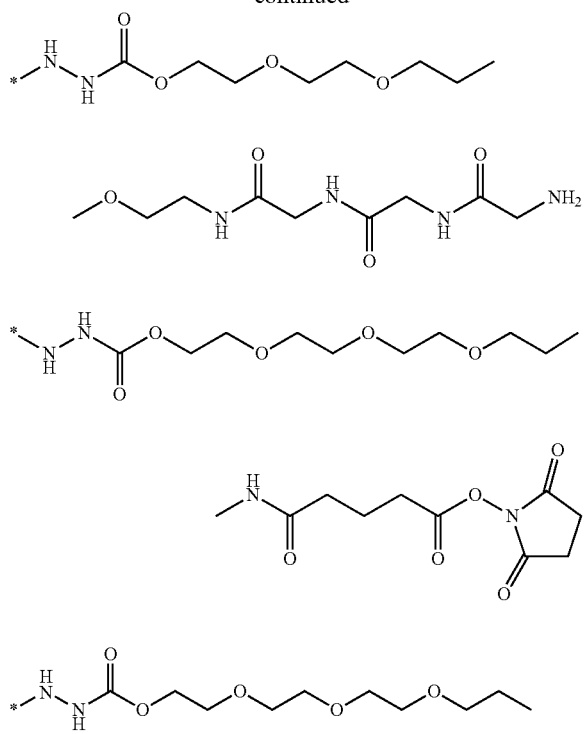

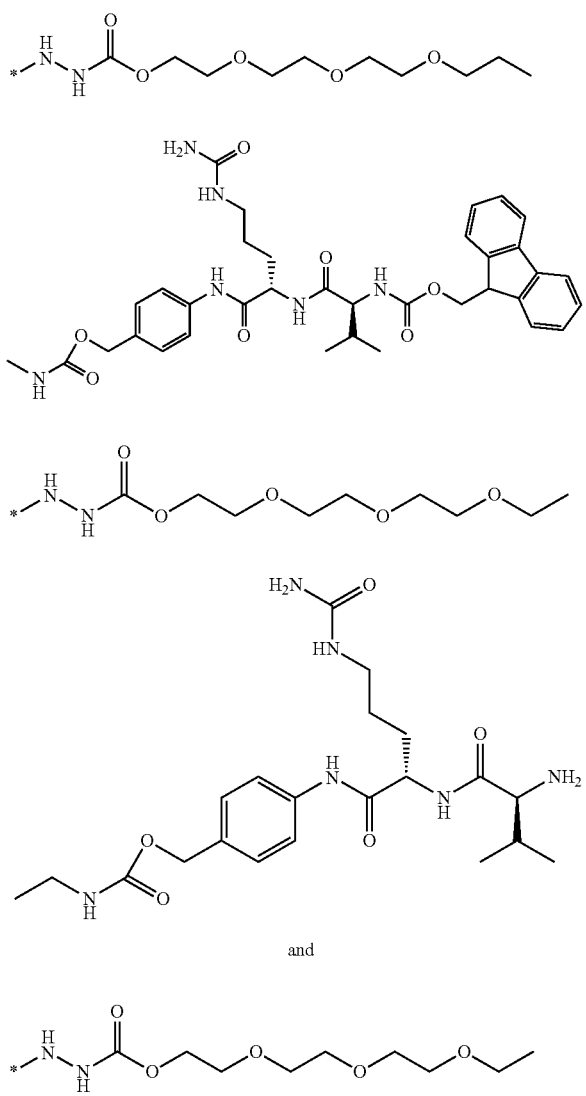

and

-continued

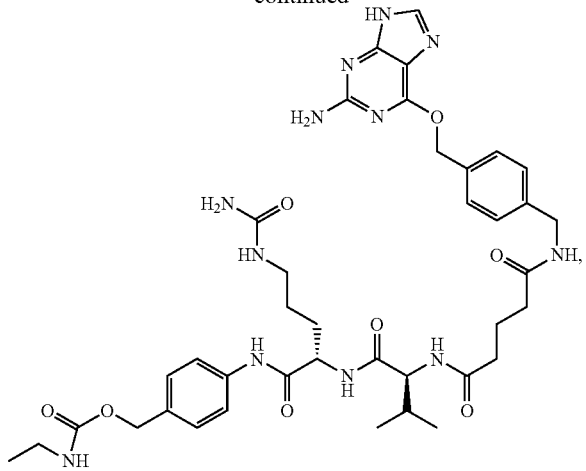

wherein * denotes the point of attachment to the compound of formula (I),
or a pharmacologically acceptable salt thereof.

2. A compound according to claim 1 having the following formula (II):

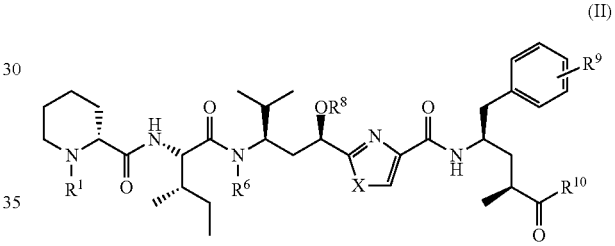

(II)

wherein $R^1$, $R^6$, $R^8$, $R^9$, $R^{10}$ and X are as defined claim 1.

3. A compound according to claim 1, wherein $R^6$ is a $C_{1-6}$ alkyl group, a group of formula —$CH_2CH_2OH$ or a group of formula $CH_2OR^{61}$ or $CH_2OCOR^{62}$, wherein $R^{61}$ is $C_{1-6}$ alkyl and $R^{62}$ is $C_{1-6}$ alkyl, $C_2$-$C_6$ alkenyl, phenyl, or $CH_2$-Phenyl.

4. A compound according to claim 1, wherein $R^8$ is H, an acetyl, a —$CH_2OCH_3$ or a $C_{1-6}$ alkyl group.

5. A compound according to claim 1, wherein $R^1$ is hydrogen, a methyl group or a group of formula —CO—$CH_2$—NH—$CH_3$; $R^9$ is H, OH, SH, F, CN, $NH_2$, Ph, Me, OMe, $CF_3$, OAc, NHMe or $NMe_2$; and $R^{10}$ is a group of Formula —$X^2$-$L^2$-$A^2$.

6. A compound according to claim 1, having the following formula (IV):

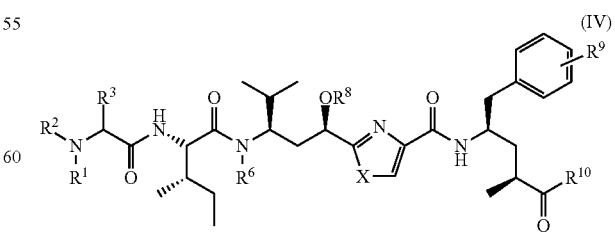

(IV)

wherein X, $R^1$, $R^6$, $R^8$, $R^9$ and $R^{10}$ are as defined in claim 1 and $R^2$ is a $C_{1-6}$ alkyl group and $R^3$ is a $C_{1-6}$ alkyl group.

7. A compound according to claim 1 which is selected from the following compounds:
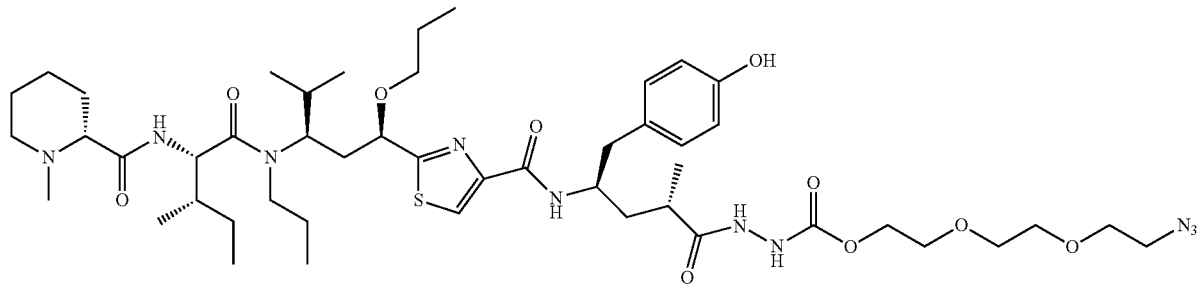
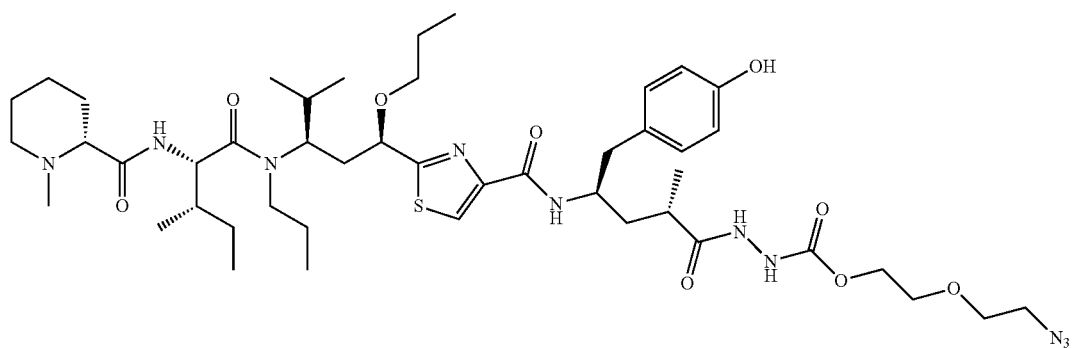
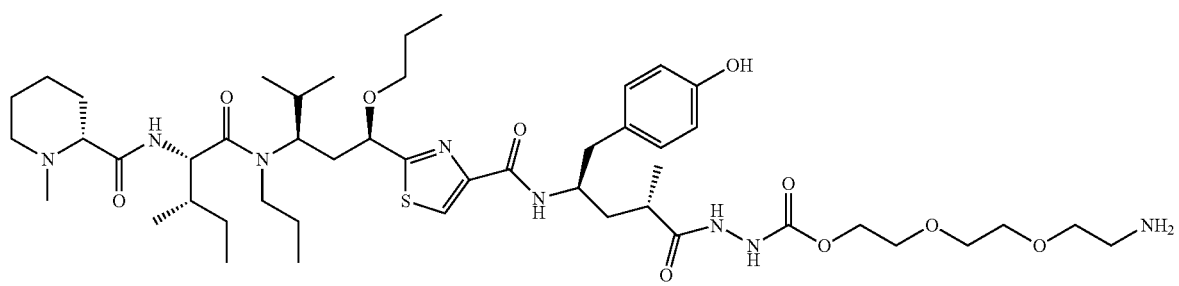 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCOCCN)cs1]
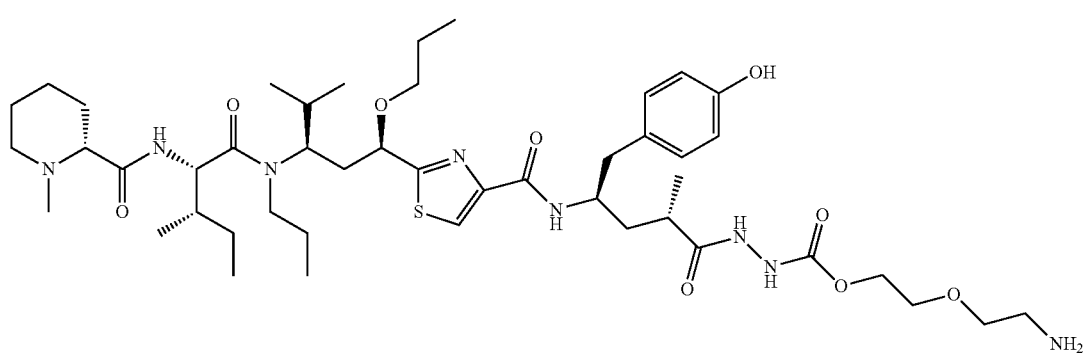 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCN)cs1]
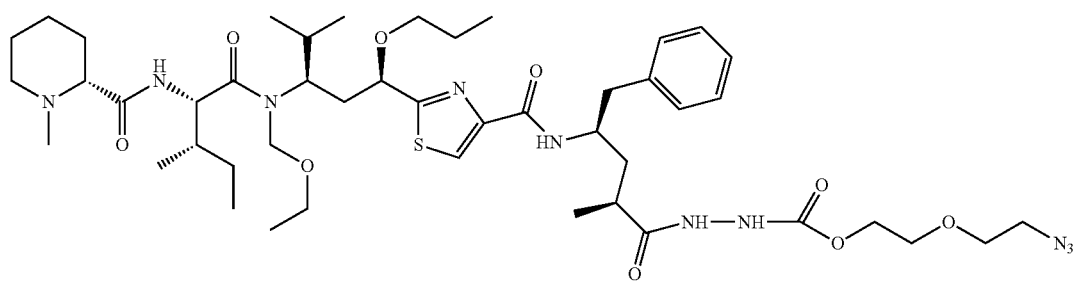

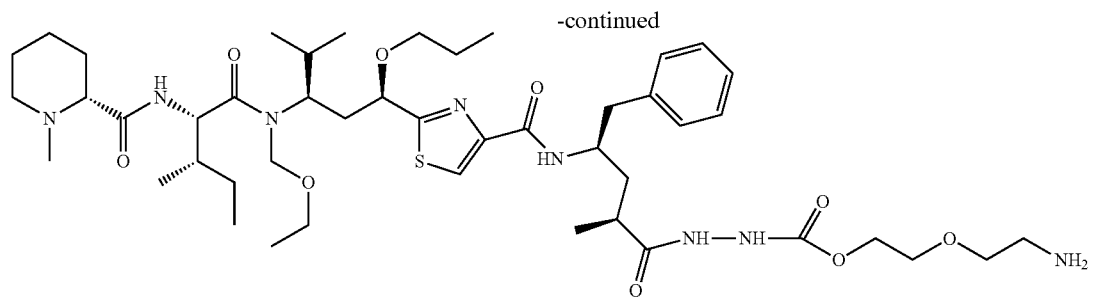
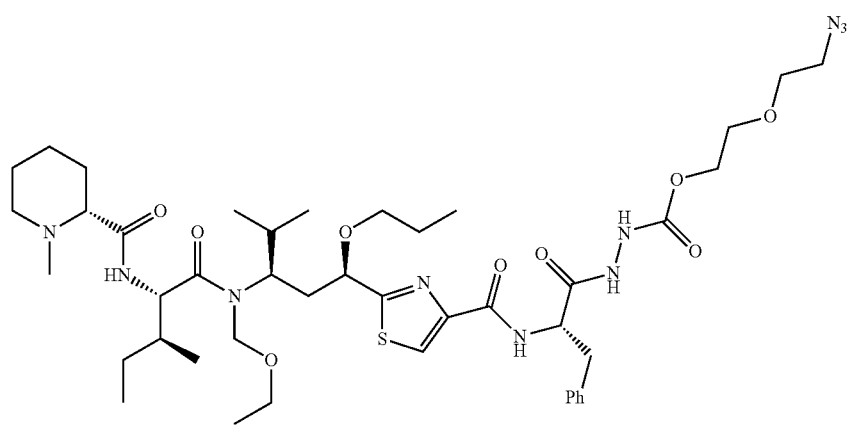
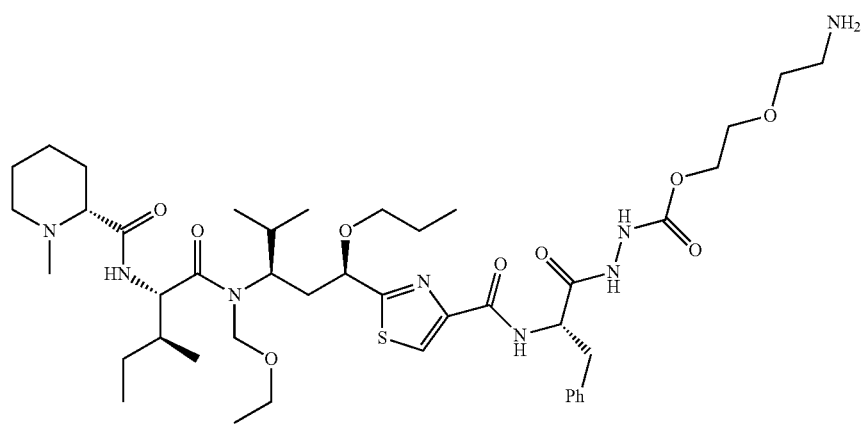
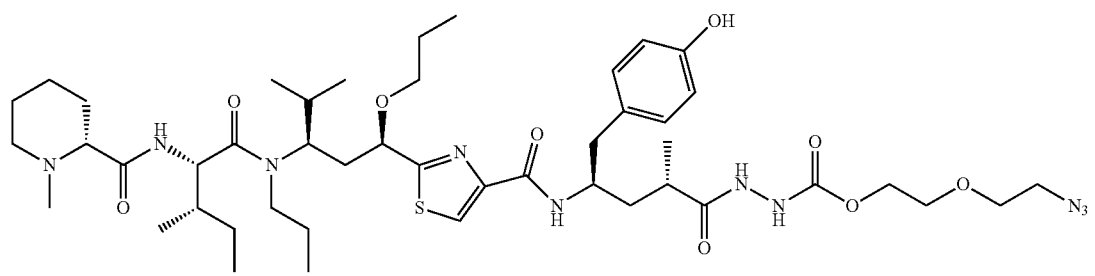
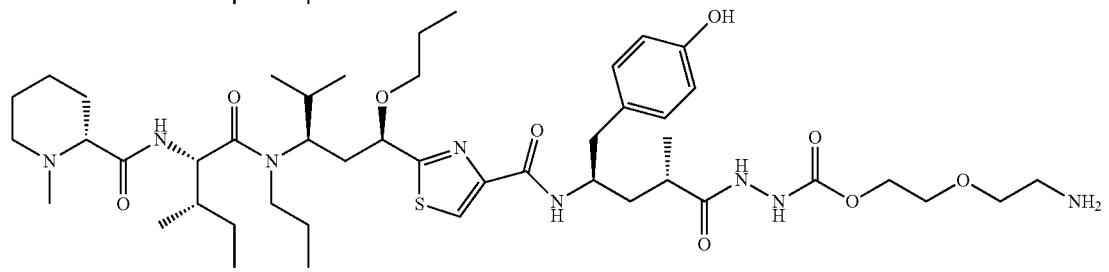

135
-continued
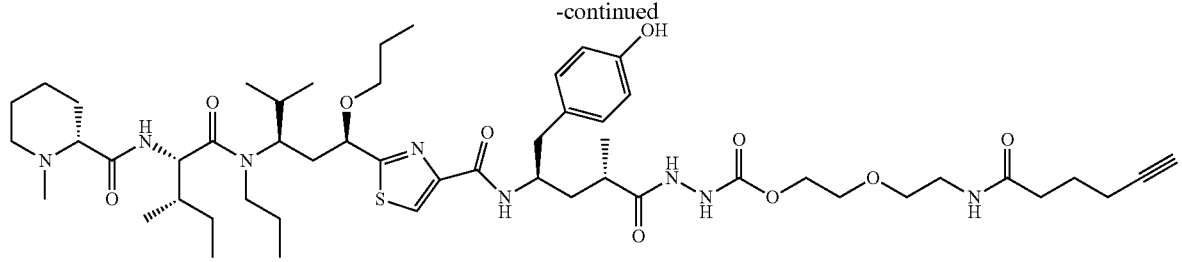
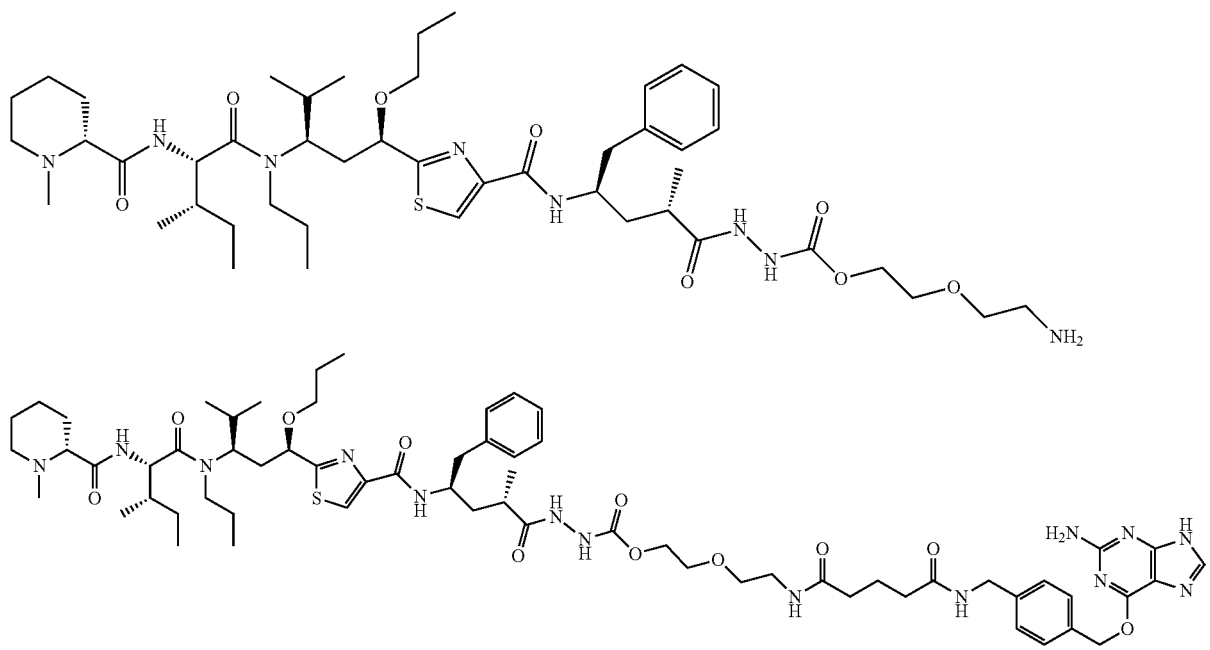
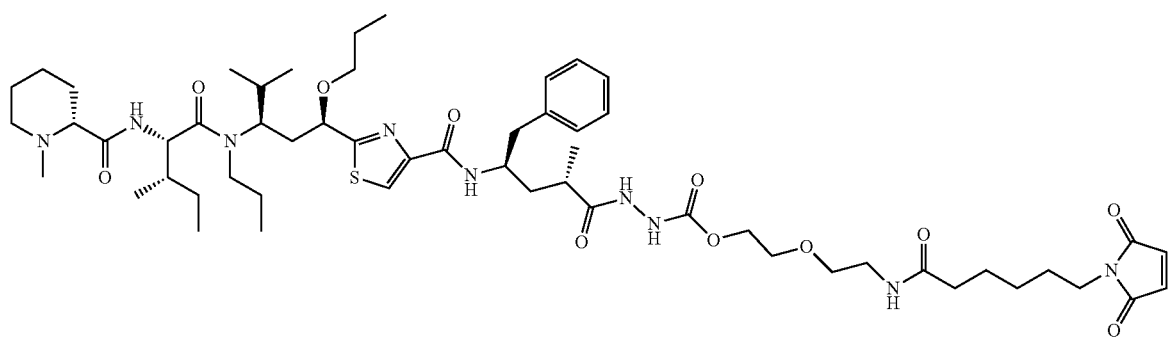
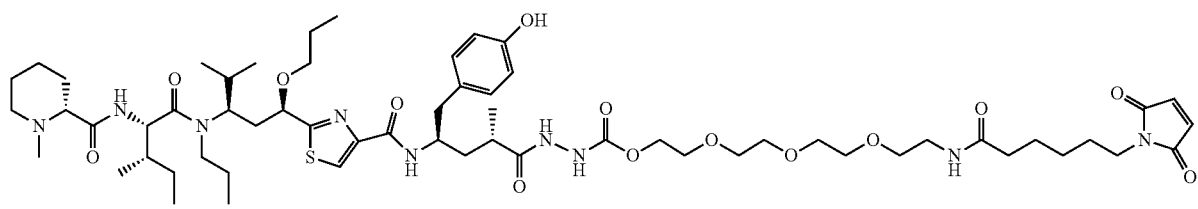
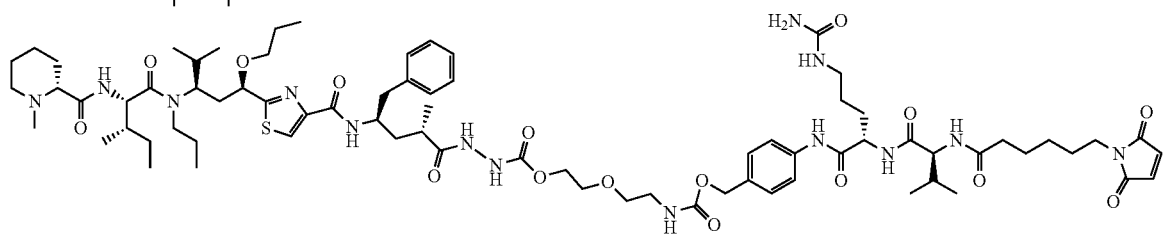
136

-continued
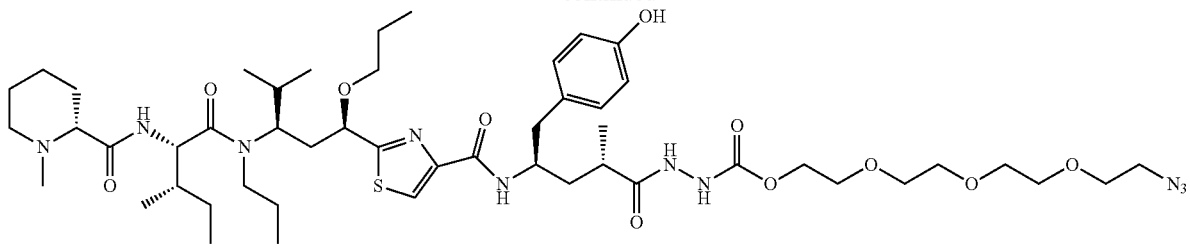
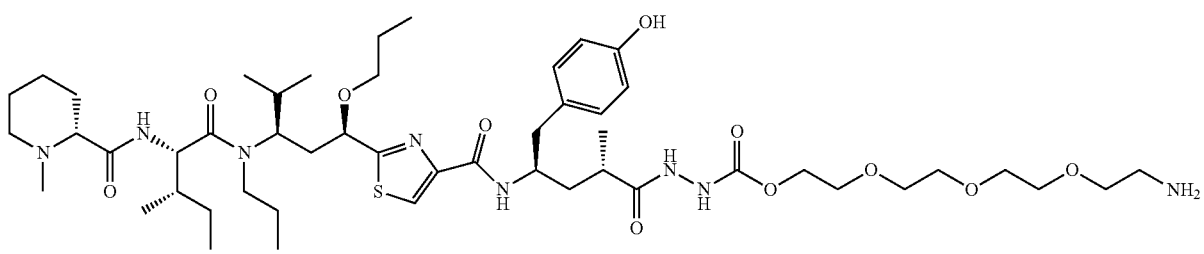
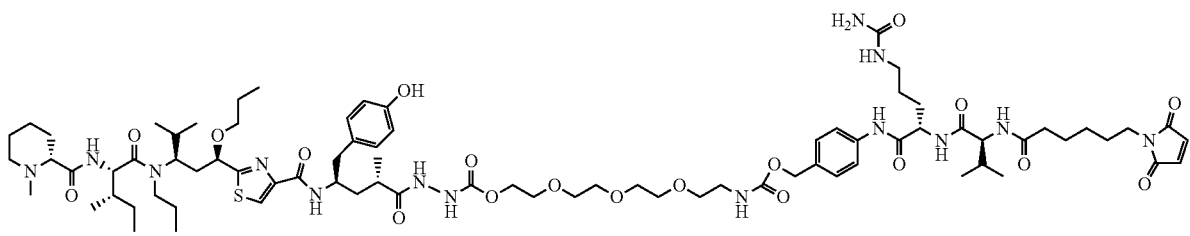
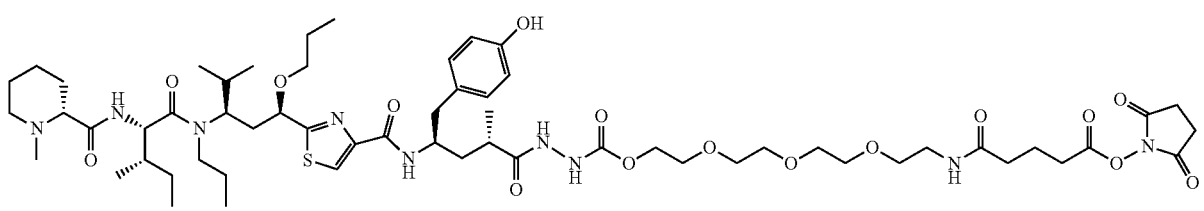 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCOCCOCCNC(=O)CCCC(=O)ON2C(=O)CCC2=O)cs1]
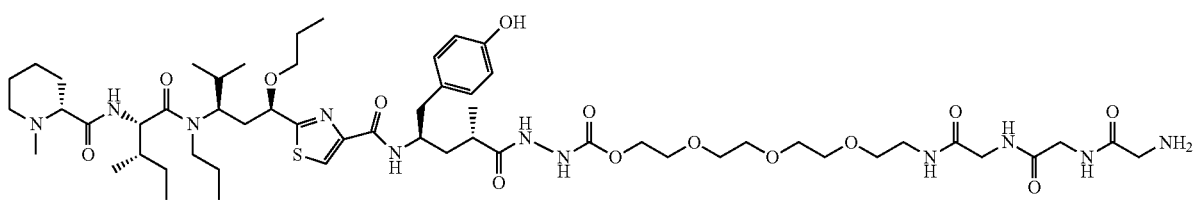 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NNC(=O)OCCOCCOCCOCCNC(=O)CNC(=O)CNC(=O)CN)cs1]
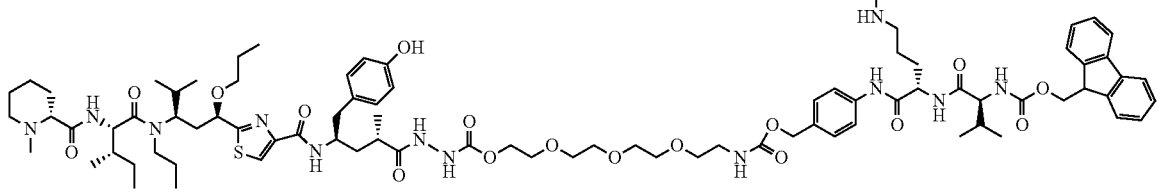
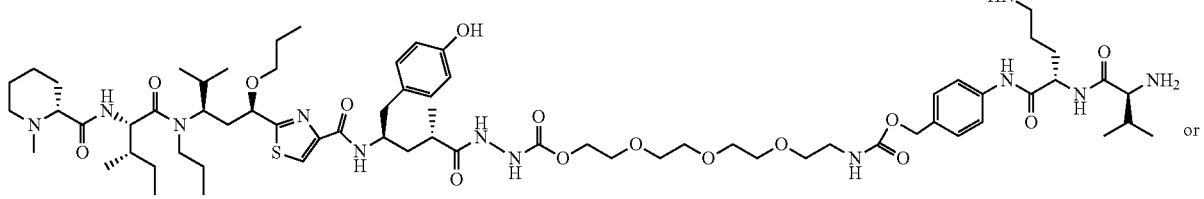
or

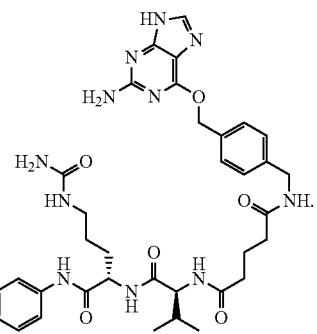
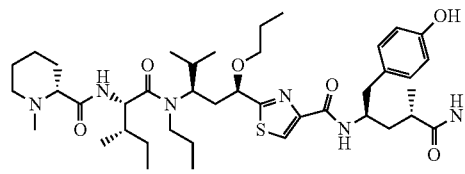
8. A compound of the following formula:
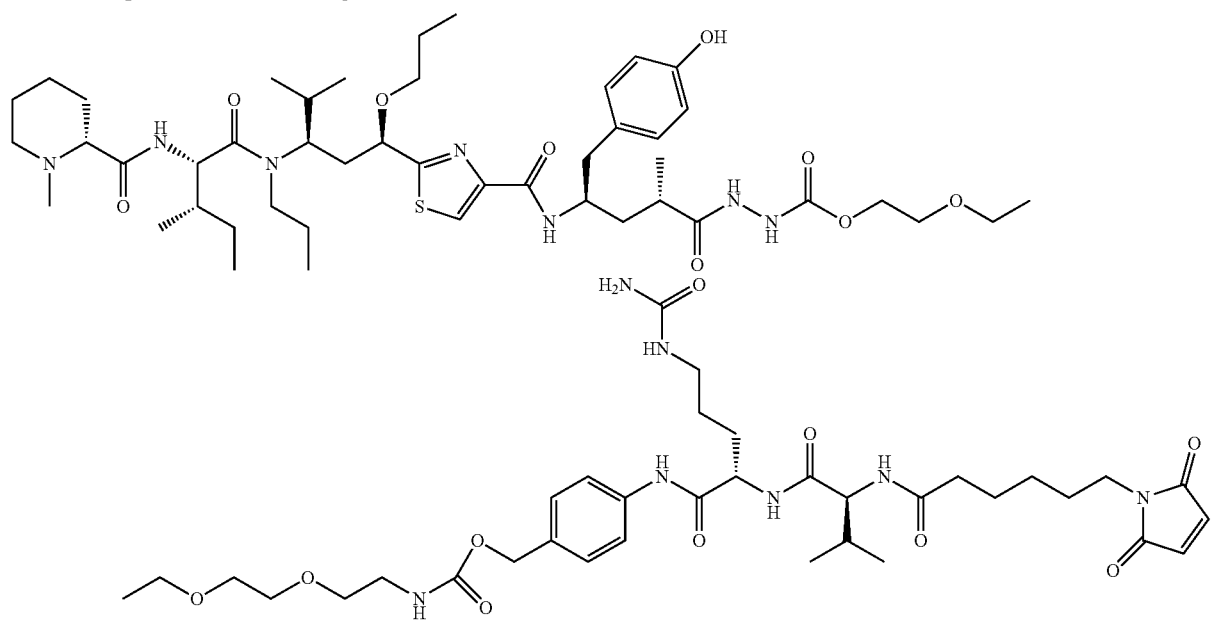
or a pharmacologically acceptable salt thereof.
9. A compound of the following formula:
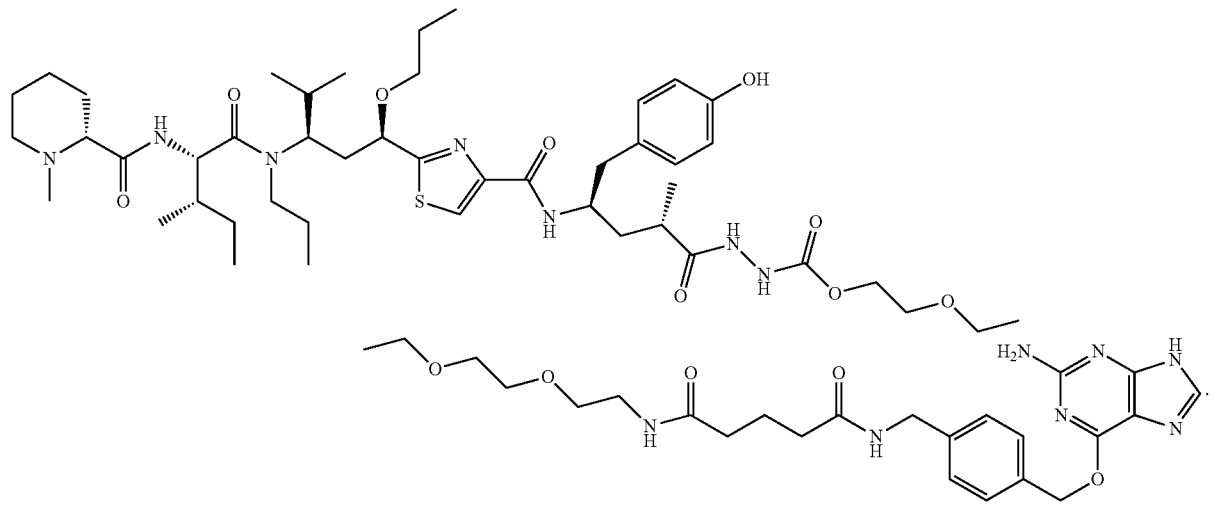
* * * * *